(12) United States Patent
Schraga

(10) Patent No.: US 8,043,318 B2
(45) Date of Patent: Oct. 25, 2011

(54) PUSH-BUTTON LANCE DEVICE AND METHOD

(75) Inventor: Steven Schraga, Surfside, FL (US)

(73) Assignee: Stat Medical Devices, Inc., North Miami, FL (US)

( * ) Notice: Subject to any disclaimer, the term of this patent is extended or adjusted under 35 U.S.C. 154(b) by 77 days.

(21) Appl. No.: 11/672,684

(22) Filed: Feb. 8, 2007

(65) Prior Publication Data

US 2008/0195132 A1    Aug. 14, 2008

(51) Int. Cl.
A61B 17/32    (2006.01)

(52) U.S. Cl. .......................................... 606/182

(58) Field of Classification Search ................ 606/181, 606/182, 183, 184; 600/583
See application file for complete search history.

(56) References Cited

U.S. PATENT DOCUMENTS

| | | | |
|---|---|---|---|
| 676,678 A | 6/1901 | Ellifrits | |
| 1,135,465 A * | 4/1915 | Pollock | 606/182 |
| 2,699,784 A | 2/1953 | Scarifier | |
| 2,848,809 A | 2/1956 | Crowder | |
| 2,823,677 A | 2/1958 | Heinm, Jr. | |
| 3,208,452 A * | 9/1965 | Stern | 606/182 |
| 3,589,213 A | 6/1971 | Gourley | |
| 3,760,809 A | 9/1973 | Campbell, Jr. | |
| 4,064,871 A | 12/1977 | Reno | |
| 4,139,011 A | 2/1979 | Benoit et al. | |
| 4,157,086 A | 6/1979 | Maiorano et al. | |
| 4,203,446 A * | 5/1980 | Hofert et al. | 606/182 |
| 4,257,561 A | 3/1981 | McKinney | |
| 4,388,925 A | 6/1983 | Burns | |
| 4,426,105 A | 1/1984 | Plaquin et al. | |
| 4,438,770 A | 3/1984 | Unger et al. | |
| 4,449,529 A | 5/1984 | Burns et al. | |
| 4,469,110 A | 9/1984 | Slama | |
| 4,517,978 A | 5/1985 | Levin et al. | |
| 4,527,561 A | 7/1985 | Burns | |
| 4,539,988 A | 9/1985 | Shirley et al. | |
| 4,553,541 A | 11/1985 | Burns | |
| 4,628,929 A | 12/1986 | Intengan et al. | |
| 4,643,189 A | 2/1987 | Mintz | |

(Continued)

FOREIGN PATENT DOCUMENTS

CA    523078    3/1956

(Continued)

OTHER PUBLICATIONS

Sutor et al., "Bleeding from Standardized Skin Punctures: Automated Technic for Recording Time, Intensity, and Pattern of Bleeding", *A.J.C.P.*, vol. 55, pp. 541-49 (May 1971).

*Primary Examiner* — Tom Hughes
*Assistant Examiner* — David Eastwood
(74) *Attorney, Agent, or Firm* — Greenblum & Bernstein, P.L.C.

(57) ABSTRACT

Lancet device utilizing a body, a holding member configured to receive a lancet having the lancet needle, a first spring structured and arranged to move the holding member between at least a retracted position and an extended position, and a second spring structured and arranged to move the holding member between at least an intermediate position and the retracted position. The first spring is at least one of smaller in diameter than the second spring and compressible by expansion of the second spring. This Abstract is not intended to define the invention disclosed in the specification, nor intended to limit the scope of the invention in any way.

58 Claims, 42 Drawing Sheets

U.S. PATENT DOCUMENTS

| | | | |
|---|---|---|---|
| 4,785,858 | A | 11/1988 | Valentini et al. |
| RE32,922 | E | 5/1989 | Levin et al. |
| 4,834,667 | A | 5/1989 | Fowler et al. |
| 4,858,607 | A | 8/1989 | Jordan et al. |
| 4,869,249 | A | 9/1989 | Crossman et al. |
| 4,895,147 | A | 1/1990 | Bodicky et al. |
| 4,924,879 | A | 5/1990 | O'Brien |
| 4,976,724 | A | 12/1990 | Nieto et al. |
| 4,990,154 | A | 2/1991 | Brown et al. |
| 5,074,872 | A | 12/1991 | Brown et al. |
| 5,133,730 | A | 7/1992 | Biro et al. |
| 5,147,375 | A | 9/1992 | Sullivan et al. |
| 5,212,879 | A | 5/1993 | Biro et al. |
| 5,269,799 | A | 12/1993 | Daniel |
| 5,282,822 | A | 2/1994 | Macors et al. |
| 5,304,193 | A | 4/1994 | Zhadanov |
| 5,314,441 | A | 5/1994 | Cusack et al. |
| 5,318,584 | A | 6/1994 | Lange et al. |
| 5,324,303 | A | 6/1994 | Strong et al. |
| 5,350,392 | A * | 9/1994 | Purcell et al. .............. 606/182 |
| 5,356,420 | A | 10/1994 | Czernecki et al. |
| 5,366,470 | A | 11/1994 | Ramel |
| 5,395,388 | A | 3/1995 | Schraga |
| 5,423,847 | A | 6/1995 | Strong et al. |
| 5,439,473 | A | 8/1995 | Jorgensen |
| 5,454,828 | A | 10/1995 | Schraga |
| 5,464,418 | A | 11/1995 | Schraga |
| 5,476,101 | A | 12/1995 | Schramm et al. |
| 5,509,345 | A | 4/1996 | Cyktick |
| 5,518,004 | A | 5/1996 | Schraga |
| 5,527,333 | A | 6/1996 | Nikkels et al. |
| 5,527,334 | A | 6/1996 | Kanner et al. |
| 5,529,581 | A | 6/1996 | Cusack |
| 5,545,174 | A | 8/1996 | Schenk et al. |
| 5,554,166 | A | 9/1996 | Lange et al. |
| 5,569,286 | A | 10/1996 | Peckham et al. |
| 5,569,287 | A | 10/1996 | Tezuka et al. |
| 5,571,132 | A | 11/1996 | Mawhirt et al. |
| D376,203 | S | 12/1996 | Schraga |
| 5,613,978 | A | 3/1997 | Harding |
| 5,628,764 | A | 5/1997 | Schraga |
| 5,628,765 | A | 5/1997 | Morita |
| 5,643,306 | A | 7/1997 | Schraga |
| 5,662,672 | A | 9/1997 | Pambianchi et al. |
| 5,730,753 | A | 3/1998 | Morita |
| 5,733,300 | A | 3/1998 | Pambianchi et al. |
| 5,741,288 | A | 4/1998 | Rife |
| RE35,803 | E | 5/1998 | Lange et al. |
| 5,772,677 | A | 6/1998 | Mawhirt et al. |
| 5,797,940 | A | 8/1998 | Mawhirt et al. |
| 5,797,942 | A | 8/1998 | Schraga |
| 5,873,887 | A | 2/1999 | King et al. |
| 5,879,367 | A | 3/1999 | Latterell et al. |
| 5,908,434 | A | 6/1999 | Schraga |
| 5,916,230 | A | 6/1999 | Brenneman et al. |
| 5,984,940 | A | 11/1999 | Davis et al. |
| 6,010,519 | A | 1/2000 | Mawhirt et al. |
| 6,022,366 | A | 2/2000 | Schraga |
| 6,042,595 | A | 3/2000 | Morita |
| 6,045,567 | A | 4/2000 | Taylor et al. |
| 6,056,765 | A | 5/2000 | Bajaj et al. |
| 6,071,294 | A | 6/2000 | Simons et al. |
| D428,150 | S | 7/2000 | Ruf et al. |
| 6,136,013 | A | 10/2000 | Marshall et al. |
| 6,152,942 | A | 11/2000 | Brenneman et al. |
| 6,156,050 | A | 12/2000 | Davis et al. |
| 6,156,051 | A | 12/2000 | Schraga |
| 6,168,606 | B1 | 1/2001 | Levin et al. |
| 6,183,489 | B1 | 2/2001 | Douglas et al. |
| 6,190,398 | B1 | 2/2001 | Schraga |
| 6,192,891 | B1 | 2/2001 | Gravel et al. |
| 6,197,040 | B1 | 3/2001 | Le Vaughn et al. |
| 6,210,420 | B1 | 4/2001 | Mauze et al. |
| 6,221,089 | B1 | 4/2001 | Mawhirt |
| 6,228,100 | B1 | 5/2001 | Schraga |
| 6,258,112 | B1 | 7/2001 | Schraga |
| 6,283,982 | B1 | 9/2001 | Levaughn et al. |
| 6,306,152 | B1 | 10/2001 | Verdonk et al. |
| 6,322,574 | B1 | 11/2001 | Lloyd et al. |
| 6,322,575 | B1 | 11/2001 | Schraga |
| 6,332,871 | B1 | 12/2001 | Douglas et al. |
| 6,346,114 | B1 | 2/2002 | Schraga |
| 6,358,265 | B1 * | 3/2002 | Thorne et al. ............. 606/181 |
| 6,364,889 | B1 | 4/2002 | Kheiri et al. |
| 6,379,317 | B1 | 4/2002 | Kintzig et al. |
| 6,395,495 | B1 | 5/2002 | Montagnier et al. |
| 6,409,740 | B1 | 6/2002 | Kuhr et al. |
| 6,419,661 | B1 | 7/2002 | Kuhr et al. |
| 6,451,040 | B1 | 9/2002 | Purcell |
| 6,464,649 | B1 | 10/2002 | Duchon et al. |
| 6,506,168 | B1 | 1/2003 | Fathallah et al. |
| 6,514,270 | B1 | 2/2003 | Schraga |
| 6,540,762 | B1 | 4/2003 | Bertling |
| 6,730,046 | B1 * | 5/2004 | Hamamoto et al. .......... 600/583 |
| 6,764,496 | B2 | 7/2004 | Schraga |
| 6,811,557 | B2 | 11/2004 | Schraga |
| 6,887,253 | B2 | 5/2005 | Schraga |
| 6,918,918 | B1 | 7/2005 | Schraga |
| 6,949,111 | B2 | 9/2005 | Schraga |
| 6,958,072 | B2 | 10/2005 | Schraga |
| 6,986,777 | B2 * | 1/2006 | Kim .......................... 606/182 |
| 7,105,006 | B2 | 9/2006 | Schraga |
| 7,175,641 | B1 | 2/2007 | Schraga |
| 2001/0027327 | A1 | 10/2001 | Schraga |
| 2002/0077650 | A1 | 6/2002 | Schraga |
| 2003/0038465 | A1 | 2/2003 | Ford |
| 2003/0050656 | A1 | 3/2003 | Schraga |
| 2003/0187470 | A1 * | 10/2003 | Chelak et al. ............. 606/182 |
| 2004/0236251 | A1 | 11/2004 | Roe et al. |
| 2005/0038464 | A1 * | 2/2005 | Shraga ...................... 606/182 |
| 2005/0234495 | A1 | 10/2005 | Schraga |
| 2005/0267505 | A9 | 12/2005 | Schraga |
| 2005/0288699 | A1 | 12/2005 | Schraga |
| 2007/0083222 | A1 | 4/2007 | Schraga |

FOREIGN PATENT DOCUMENTS

| | | |
|---|---|---|
| EP | 0061102 | 9/1982 |
| EP | 0137975 | 4/1985 |
| EP | 0189117 | 7/1986 |
| EP | 0885590 | 12/1998 |
| EP | 0904731 | 3/1999 |
| EP | 1074219 | 2/2001 |
| FR | 1126718 | 11/1956 |

* cited by examiner

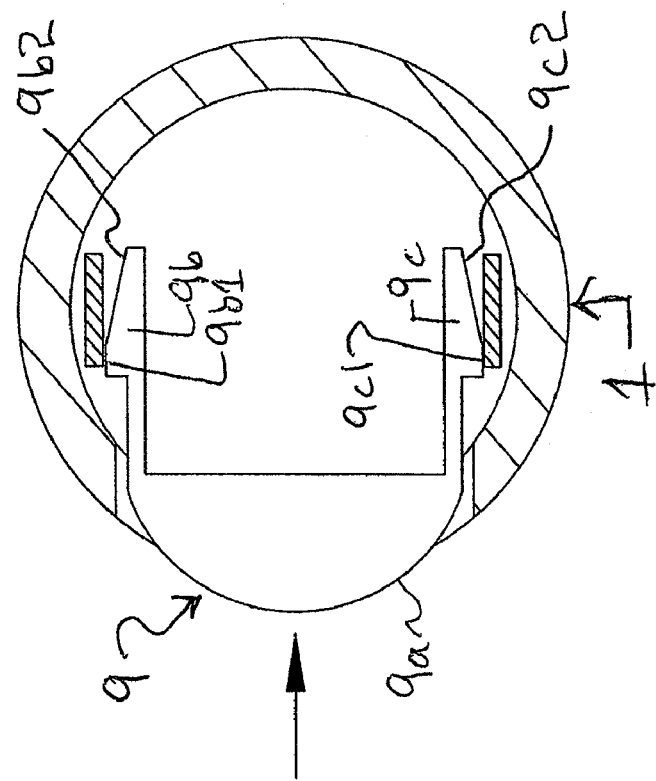
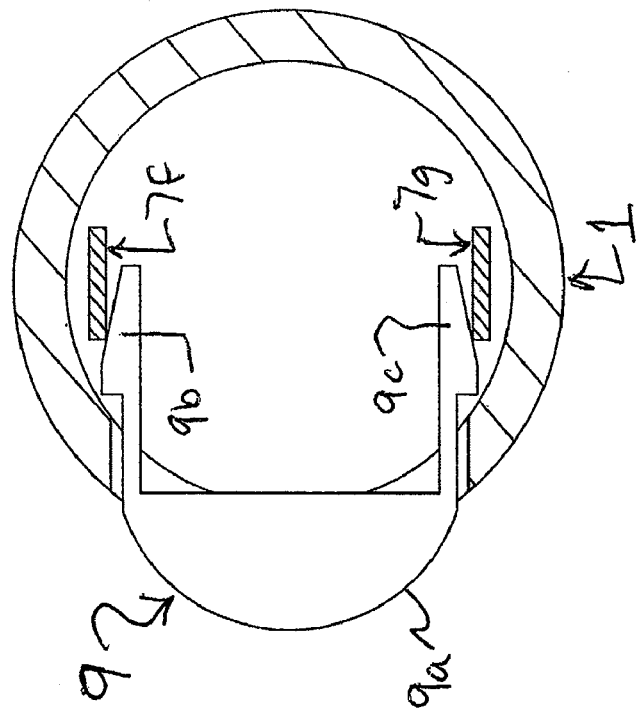

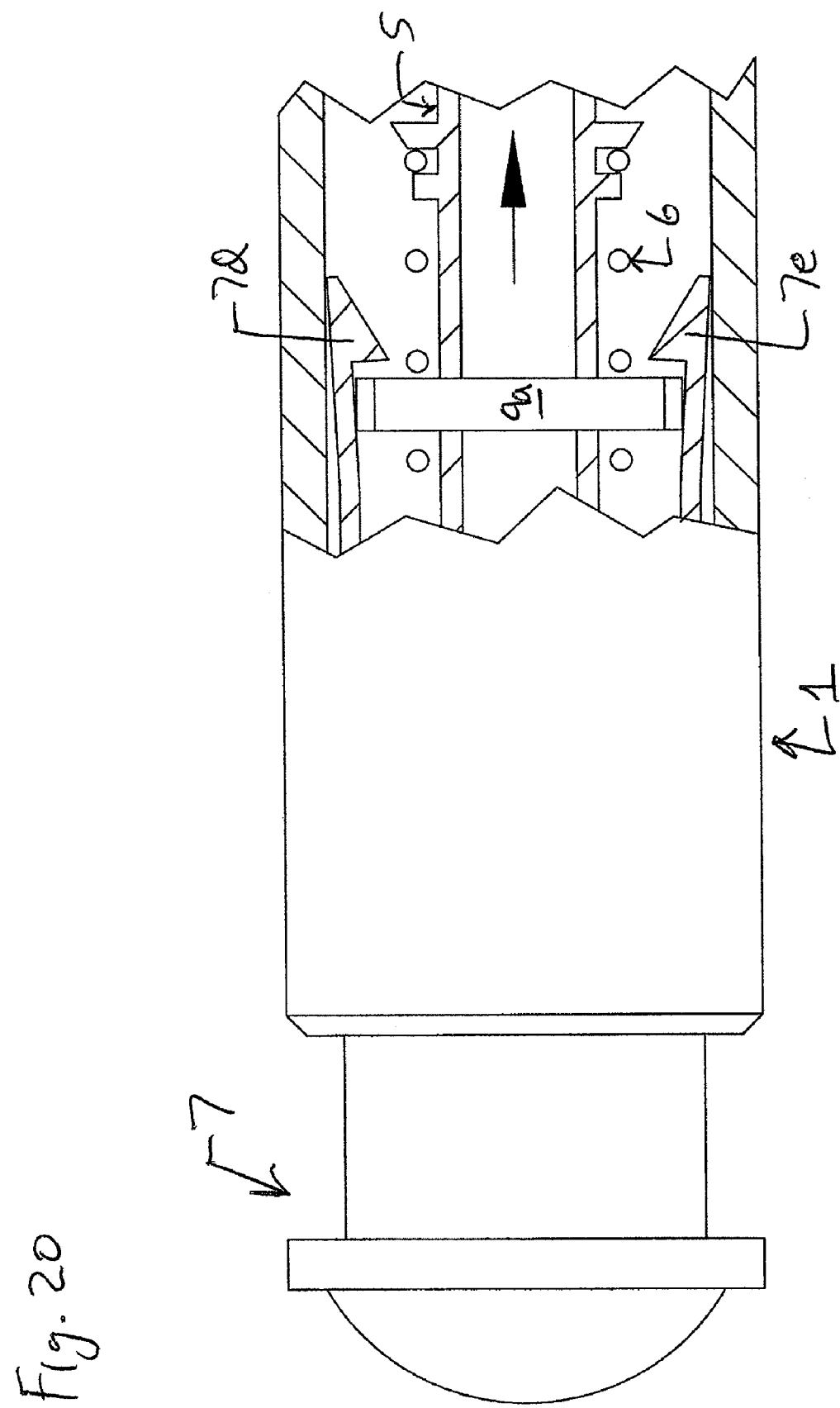

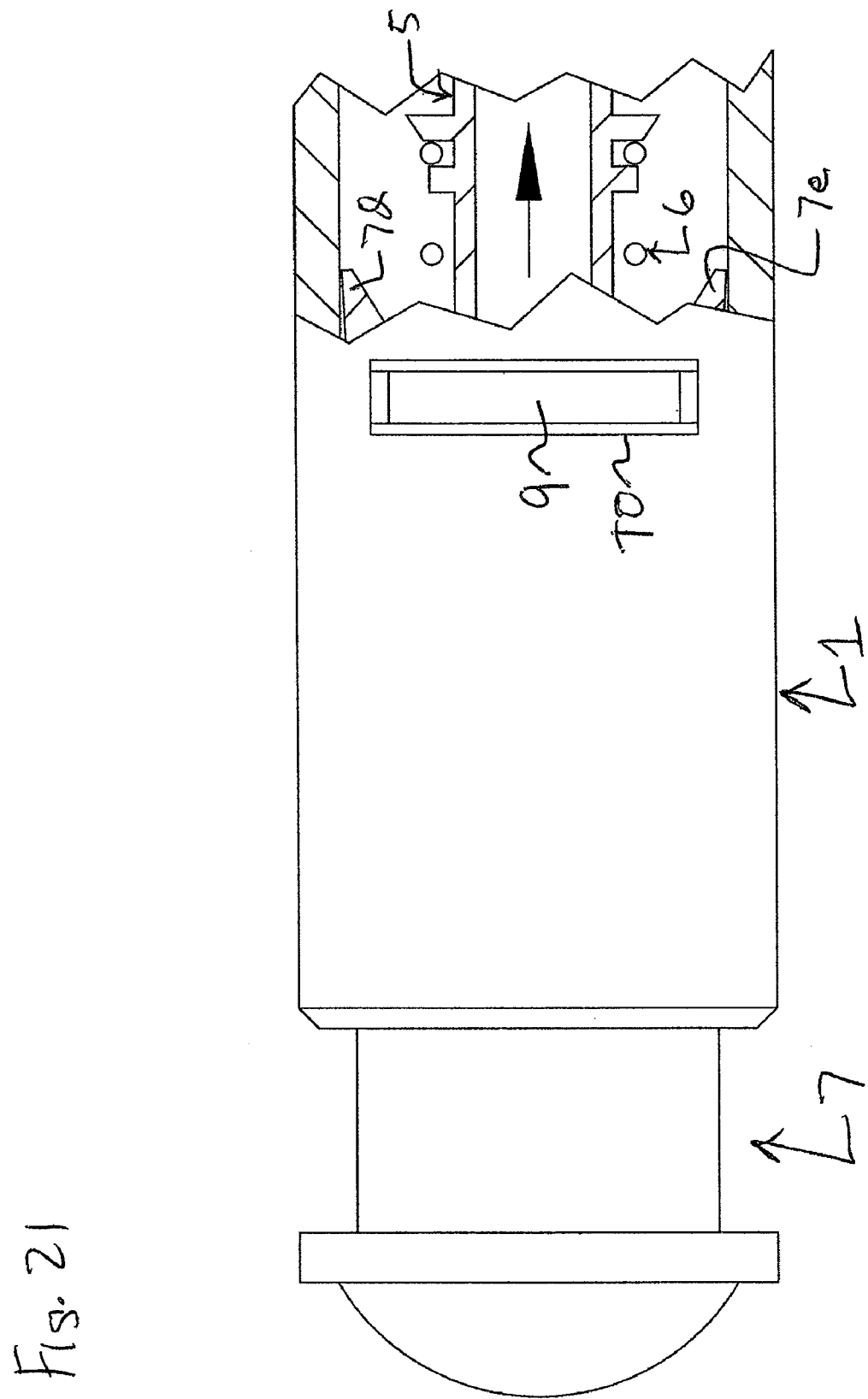

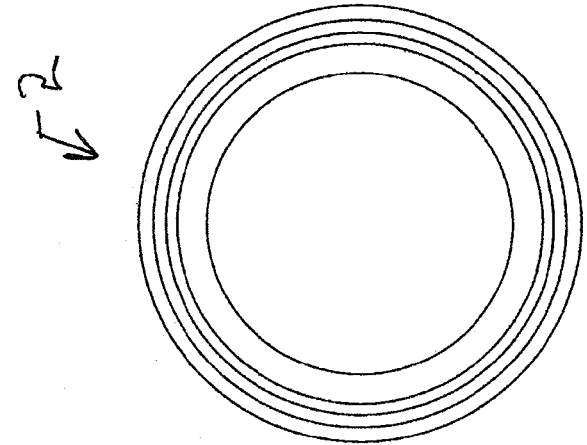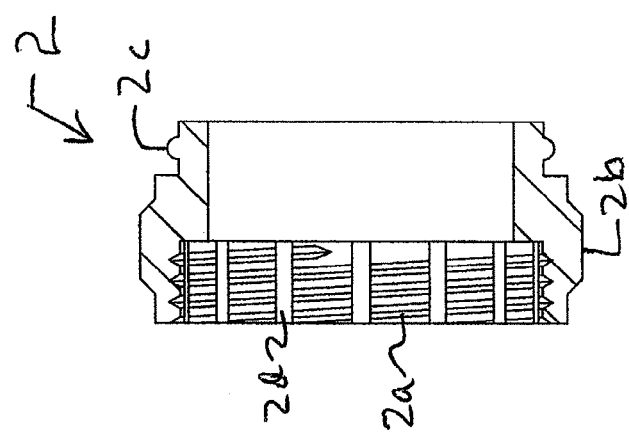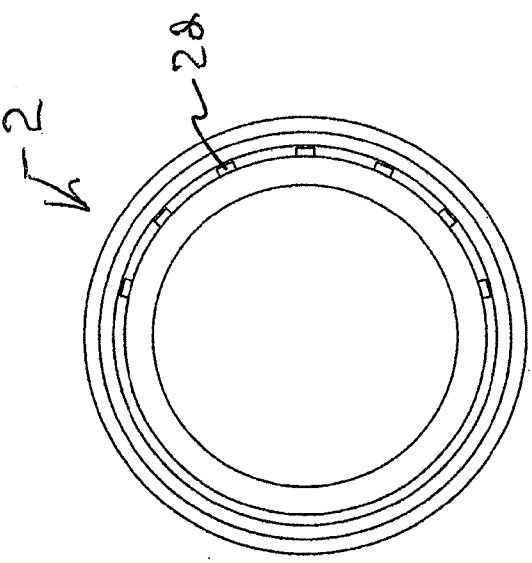

PUSH-BUTTON LANCE DEVICE AND METHOD

BACKGROUND OF THE INVENTION

1. Field of the Invention

The invention relates to a lancet device having a cocking and triggering system. The system may be structured and arranged to automatically cock and trigger the lancet device when activated by a user. The invention also relates to a lancet device which is easier to use and/or more economical and which is more efficient to make. The invention also relates to a lancet device preferably having an adjusting capability, and a method of using a lancet device. In particular, the invention relates to a lancet device which can be used with one hand. The lancet device can also have adjustable depth penetration. The present device also specifically allows the user to cock and trigger the lancet device using only one hand, i.e., one-handed operation.

2. Discussion of Background Information

Lancet devices are used to penetrate and puncture the skin in order to allow the taking of a blood sample for testing. In particular, lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have thicker skin. By adjusting the depth of puncture so that the depth is no greater than necessary for extracting a required amount of blood, any pain experienced by the user may be minimized.

Lancets having an adjustable tip are known perse. For example, U.S. Pat. No. 4,469,110 to SLAMA discloses a mechanism which adjusts the penetration depth by rotating a threaded sleeve relative to a body. The SLAMA device is characterized as a "single bottom" device which employs a threaded design which can be expensive to manufacture. Moreover, such a device may require the user to rotate the threaded sleeve up to 360 degrees and more in order to attain the proper depth setting. Further, such a threaded resign is prone to inadvertent setting changes since there is nothing but frictional engagement between the mating threads to maintain the adjustment setting.

U.S. Pat. No. 4,895,147 to BODICKY et al. functions in a similar manner to the device in SLAMA and therefore suffers from similar disadvantages.

U.S. Pat. Nos. 5,464,418, 5,797,942, 5,908,434, 6,156,051 and 6,530,937 to SCHRAGA also disclose similar lancet devices and are hereby incorporated herein by reference as though set forth in full herein.

As disclosed in U.S. Pat. No. 5,908,434, the lancet device has a body portion which encloses a lancet and a lancet firing mechanism. The lancet typically has a needle extending therefrom and is caused to move towards the tip of the device by a trigger or firing mechanism. The lancet device forces the needle, by virtue of the needle being fixed thereto, out of the device by some distance or depth so that the needle can penetrate the skin of the user. The function of this firing mechanism and the lancet body design is disclosed in each of U.S. Pat. No. 5,797,942 and U.S. Pat. No. 5,908,434. These Patents are incorporated by reference herein in their entirety and are therefore only briefly discussed herein. Similarly, U.S. Pat. No. 6,156,051 discloses a lancet device which utilizes a lancet firing mechanism, a depth adjustment mechanism, and a trigger setting mechanism. This patent is incorporated by reference herein in its entirety.

What is needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices. It is further also desirable to allow the user to cock and trigger the lancet device using only one hand, i.e., one-handed operation.

Thus, while advances have been made, there is a continuing need for a lancet device which provides for convenient, reliable and easy adjustment of penetration depth.

SUMMARY OF THE INVENTION

According to one aspect of the invention there is provided a lancet device that includes a body. A front cover includes a skin engaging end that includes a lancet opening through which a lancet needle extends. A holding member is movably mounted within the body and comprises a front end and a rear end. The front end is configured to receive a lancet. A first spring is structured and arranged to move the holding member between at least a retracted position and an extended position. A second spring is structured and arranged to move the holding member between at least an intermediate position and the retracted position.

The lancet device may have an adjustable depth of penetration arrangement. The adjustable depth of penetration arrangement may comprise an intermediate member that is at least one of axially adjustably connected to the body and threadably connected to the body. The intermediate member may be non-removably connected to the body and wherein the front cover is movably and removably connected to the intermediate member. Movement of the intermediate member may adjust a depth of penetration of the lancet needle. The front cover may be non-rotatably mounted to the intermediate member. The front cover may be devoid of moving parts. The front cover may comprise a one-piece plastic or synthetic resin member. Movement of the intermediate member may change an overall length of the lancet device and the intermediate member may be spaced from the front cover.

Axial expansion of the second spring may cause axial compression of the first spring. The second spring may be sized and/or configured to resist greater compression forces than the first spring. The second spring may be larger in diameter than the first spring. The second spring may be made from a wire having a larger diameter than a wire of the first spring. Each of the first and second springs may comprise a helical compression spring. The first spring may have one end coupled to a portion of the body and another end coupled to a portion of the holding member. The second spring may bias a rear push-button member towards an extended position.

The lancet device may be structured and arranged to allow for replacement of the lancet and for multiple use. The lancet may be removably connected to the front end of the holding member.

The lancet device may further comprise an arrangement for moving the holding member to a retracted or trigger-set position. The holding member may comprise a generally cylindrical cross-section. The holding member may comprise a generally polygonal cross-section.

The lancet device may further comprise a locking member structured and arranged to releasably lock with the holding member and thereby retain the holding member in the retracted position. The lancet device may further comprise a deflecting member coupled to the holding member, wherein the deflecting member is engagable with a trigger. The lancet device may further comprise a trigger movably mounted to the body. The lancet device may further comprise a fixed stop surface that is contacted by a movable stop surface when the holding member moves to an extended position.

The front cover may be removably and non-threadably mounted to a front portion of the body and further comprising an intermediate member non-removably mounted to a rear portion of the body. The lancet device may further comprise a mechanism for at least temporarily maintaining a depth setting position. The holding member may comprise an integrally formed deflecting member that engages a surface of the body. The front end of the holding member may comprise an opening that is configured to removably receive the lancet.

The lancet device may further comprise at least one deflectable member configured to be deflected by a trigger thereby causing movement of the holding member to the extended position. The at least one deflectable member may be coupled to a push-button. The at least one deflectable member may be integrally formed with a push-button.

The lancet device may further comprise indicia arranged on at least one of an intermediate member and the body. The indicia may be arranged on an outer circumferential surface of the body. The indicia may be arranged on an outer circumferential surface of the intermediate member. The front cover may rotate about an axis that runs through the lancet opening and the holding member without changing an overall length of the lancet device. The second spring may be disposed between a trigger and a back cap or push-button. The body may comprise a two-piece body. The lancet device may further comprise a back cap movably mounted to the body and biased towards an extended position by the second spring. The body may comprise an ergonomic shape. The body may comprise a plastic material. The lancet device may further comprise an intermediate member that comprises at least one of an external high-friction gripping surface and gripping protrusions. The lancet device may further comprise threads connecting an intermediate member to the body.

The invention also provides for a method of puncturing a surface of skin using the lancet device of the type described above or below, wherein the method comprises adjusting a set depth of penetration by rotating the intermediate member to a desired set position, disposing the skin engaging end against a user's skin, and compressing the second spring and thereafter allowing the second spring to automatically expand thereby causing compression of the first spring.

The invention also provides for a method of puncturing a surface of skin using the lancet device of the type described above or below, wherein the method comprises adjusting a set depth of penetration by rotating the intermediate member to a desired set position, disposing the skin engaging end against a user's skin, and compressing the second spring while the first spring remains in an unstressed state and thereafter allowing the second spring to expand thereby causing compression of the first spring.

The invention also provides for a method of puncturing a surface of skin using the lancet device of the type described above or below, wherein the method comprises disposing the skin engaging end against a user's skin and compressing the second spring while the first spring remains in an unstressed state and thereafter allowing the second spring to expand thereby automatically causing compression of the first spring.

The invention also provides for an adjustable depth of penetration lancet device, wherein the lancet device comprises a body, a front cover comprising a skin engaging end that includes a lancet opening through which a lancet needle may extend, a holding member movably mounted within the body and comprising a front end and a rear end, the front end being configured to receive a lancet having the lancet needle, a first spring structured and arranged to move the holding member between at least a retracted position and an extended position, a second spring structured and arranged to at least one of move the holding member between at least an intermediate position and the retracted position and cause compression of the first spring, and a push-button member structured and arranged to at least one of cause compression of the second spring and move the holding member to the retracted position.

The invention also provides for a lancet device comprising a body, a front cover comprising a skin engaging end that includes a lancet opening through which a lancet needle may extend, a holding member movably mounted within the body and comprising a front end and a rear end, the front end being configured to receive a lancet having the lancet needle, a first spring structured and arranged to move the holding member between at least a retracted position and an extended position, a second spring structured and arranged to move the holding member between at least an intermediate position and the retracted position and to cause compression of the first spring, and at least one of a push-button member structured and arranged to cause compression of the second spring and to move the holding member to the retracted position, and a triggering arrangement structured and arranged to releasably engage with the holding member.

The invention also provides for a lancet device, wherein the lancet device comprises a body, a holding member movably mounted within the body and comprising a front end and a rear end, the front end being configured to receive a lancet having the lancet needle, a first spring structured and arranged to move the holding member between at least a retracted position and an extended position, and a second spring structured and arranged to move the holding member between at least an intermediate position and the retracted position. The first spring is at least one of smaller in diameter than the second spring and compressible by axial expansion of the second spring. The lancet device may further comprise an automatic triggering system structured and arranged to be activated when the second spring expands and compresses the first spring.

The invention also provides for a lancet device comprising a body, a movable lancet holding member, and a cocking and triggering system structured and arranged to automatically cock and trigger the lancet device when activated by a user.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 18 shows an end cross-section view of the lancet device shown in FIG. 1 and further utilizing a trigger. The trigger is not shown in cross-section. The internal portion of the body, the springs and the holding member are not illustrated. The trigger is shown in an initial position prior to causing firing of the lancet device;

FIG. 19 shows another end cross-section view of the lancet device shown in FIG. 18. The trigger is shown in a triggering position causing firing of the lancet device and the arrow indicated inward movement of the trigger;

FIG. 20 shows a partial cross-section view of the lancet device shown in FIG. 19 with the internal features not shown in FIG. 19 being illustrated;

FIG. 21 shows a partial cross-section view of the lancet device shown in FIG. 20 and illustrates the trigger opening in the body which receives the trigger;

FIG. 36 shows a rear end view of the intermediate member used in the lancet device shown in FIG. 30;

FIG. 37 shows a side cross-section view of the intermediate member shown in FIG. 36;

FIG. 38 shows a front end view of the intermediate member shown in FIG. 36;

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 13:
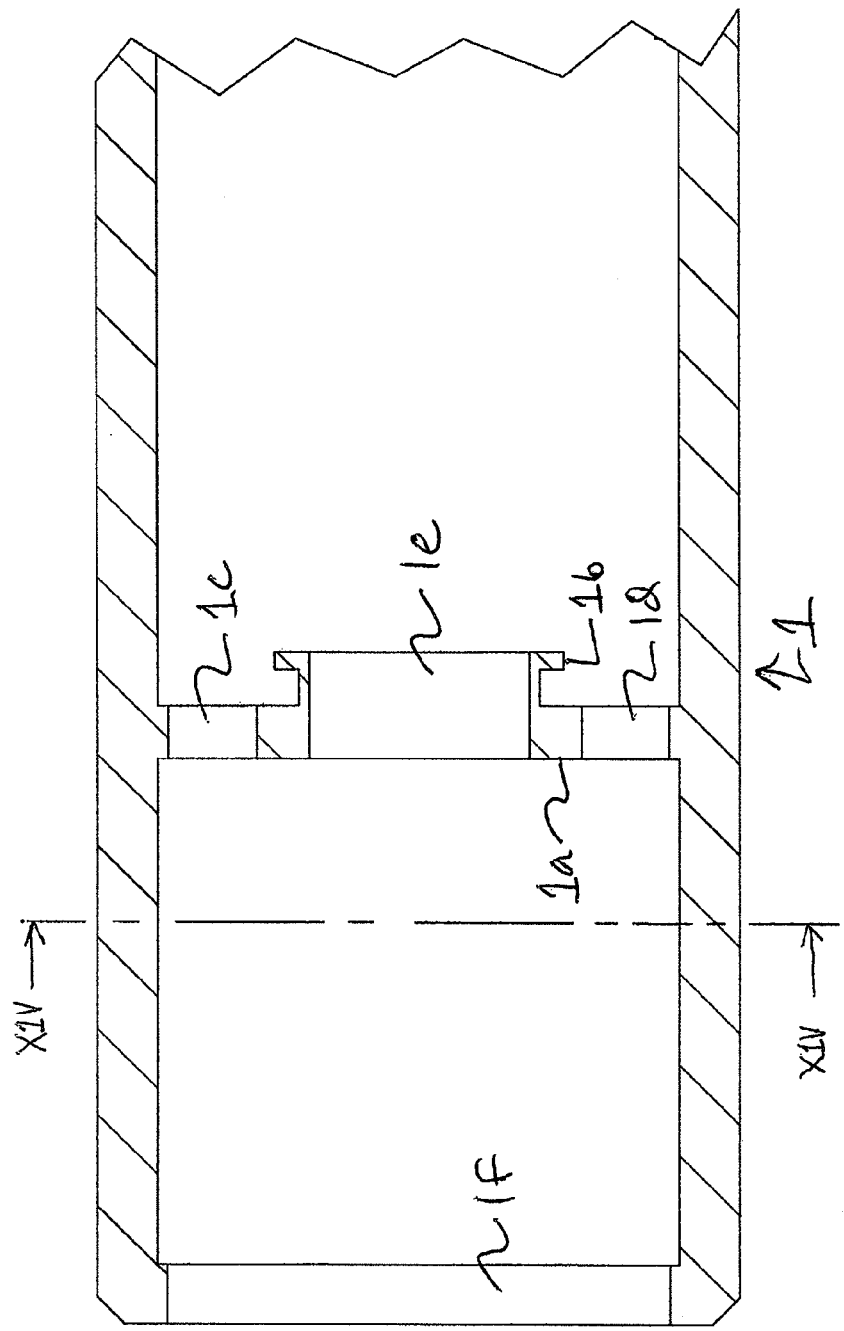
FIG. 13 shows a side cross-section view of the body used in the embodiment shown in FIG. 1.
Figure 14:
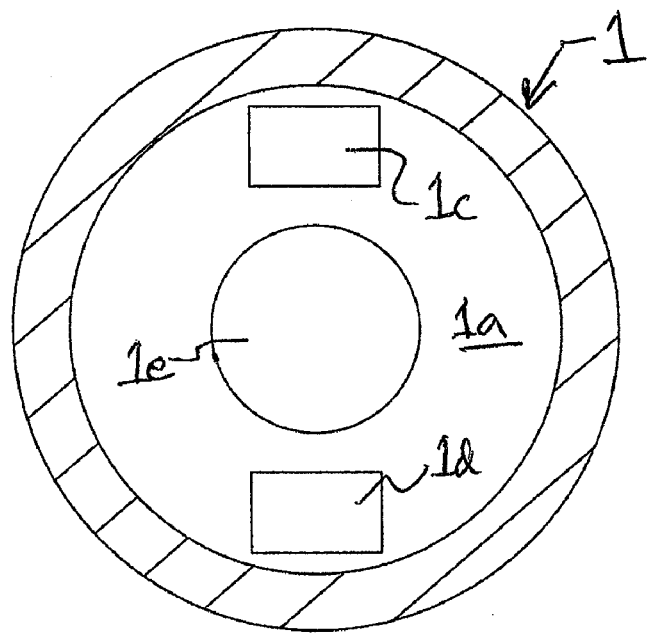
FIG. 14 shows an end cross-section view of the body shown in FIG. 13.
Figure 15:
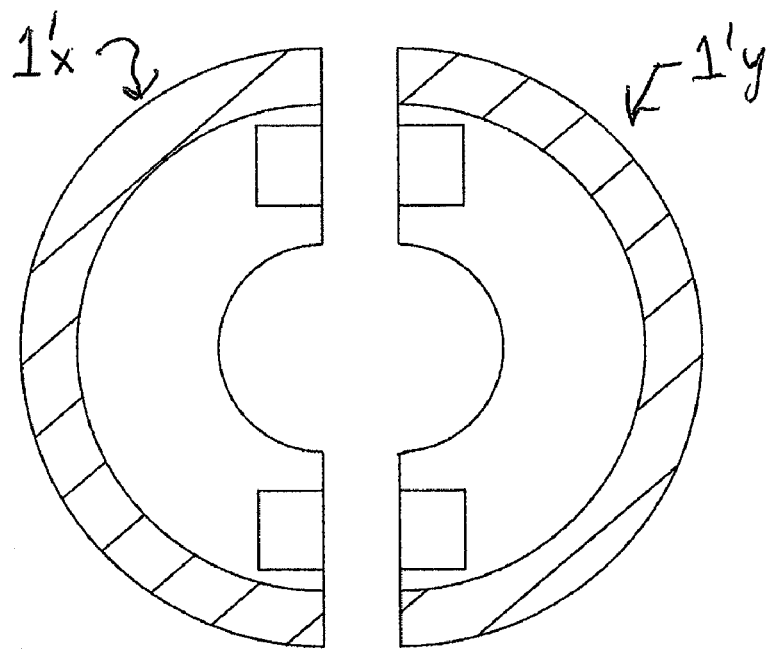
FIG. 15 shows an end cross-section view of an optional two-piece body of the type shown in FIG. 13.
Figure 33:
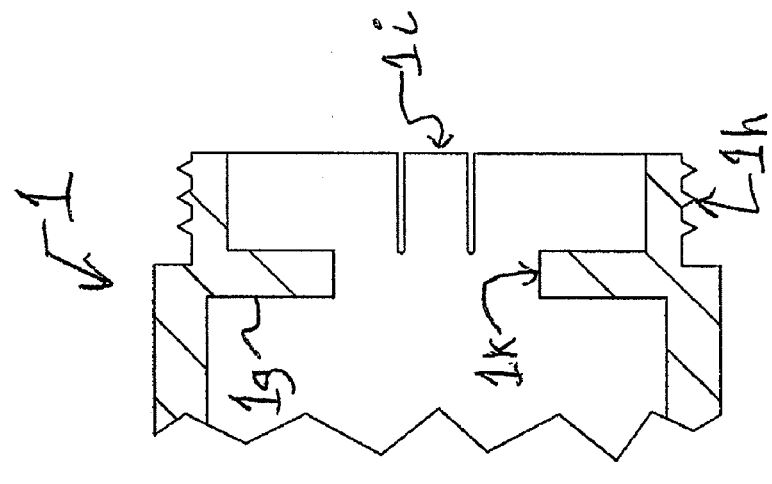
FIG. 33 shows a partial cross-section view of a front portion of the body used in the lancet device shown in FIG. 30.
Figure 32:
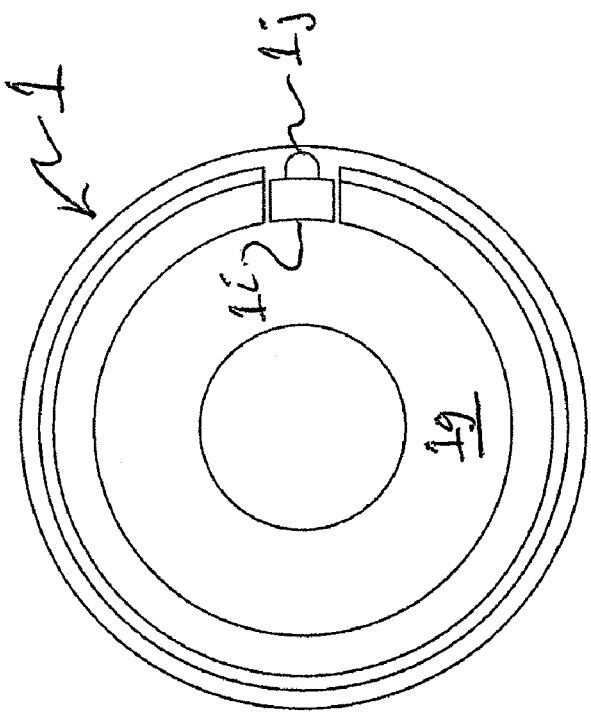
FIG. 32 shows a front end view of the body used in the lancet device shown in FIG. 30.
Figure 35:
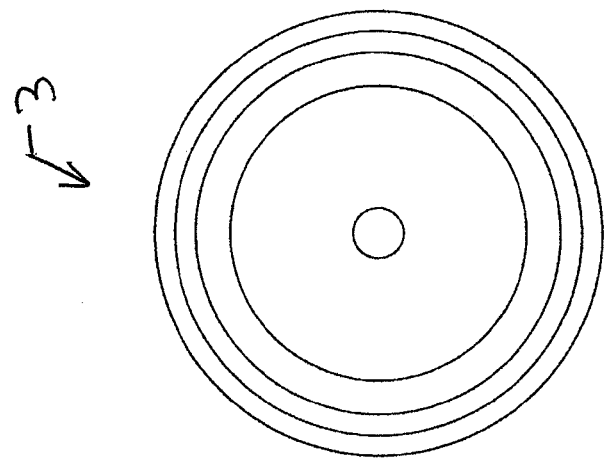
FIG. 35 shows a rear end view of the front cap shown in FIG. 34.
Figure 34:
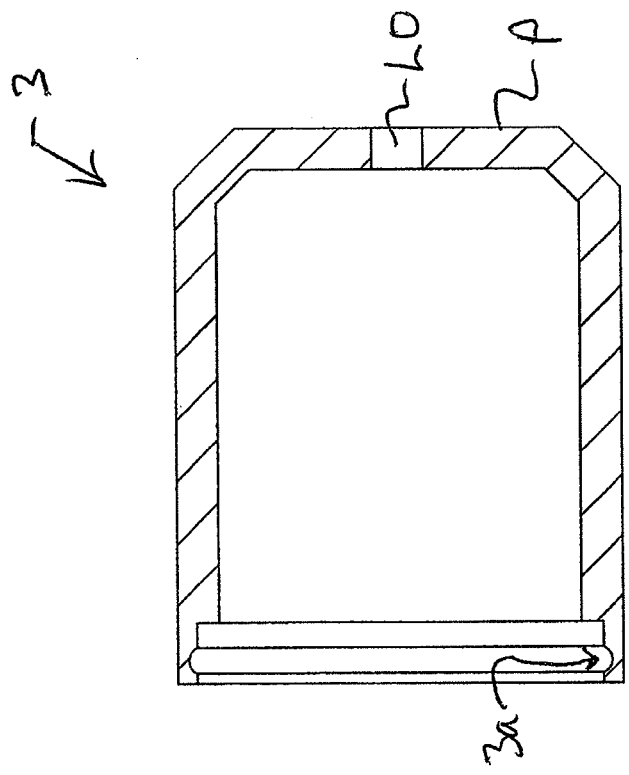
FIG. 34 shows a side cross-section view of the front cap used in the lancet device shown in FIG. 30.

FIGS. 1-38 show a first set of non-limiting embodiments of lancet device. Lancet device LD has a lancet body 1 which can be made as a one-piece member as is shown in FIGS. 13 and 14, as a two-piece body as shown in FIG. 15 or alternatively FIG. 16. Such body parts can, of course, be connected, e.g., using adhesives and/or fasteners and/or welding and/or snap-together holding mechanisms (not shown) to each other when the lancet device LD is initially assembled. A holding member 5 is movably disposed within the body 1. Also, a front cover 3 (see FIG. 30) is removably connected or attached to an intermediate and/or an adjustable section 2. The adjustable section or intermediate member 2 is threadably mounted to a front portion of the body 1. By removing the front cover 3, a user can gain access to the lancet L. The lancet L can thus be removed and replaced with a new lancet L, as needed, once the front cover 3 is removed. As in known lancet devices, the lancet device LD defines a plane P which is configured to contact (i.e., be positioned against) a user's skin. Although not shown, the instant embodiment may also utilize an inwardly curved and/or an outwardly curved surface plane P beyond which the lancet need can extend. The lancet holder 5 has a rear portion and a front portion 4 that can be accessed by a user upon removal of the front cover 3 in order to all for replacement of the lancet L. The holding member 5 slides within the body 1 and more specifically slides within openings 1e (see FIG. 13) and 1k (see FIG. 33). As will be described in more detail later on, movement of the holding member 5 rearwardly, causes the holding member 5 to retract until it reaches a spring loaded position shown in FIG. 4. The lancet L, itself is conventional and includes a needle. It can be removed and replaced with a new one, as is the case in many lancet devices. To ensure that lancet L is securely (yet removably) retained within the lancet device LD, the front portion 4 of the holding member 5 includes a lancet holding opening 5a which receives the lancet L therein.

Figure 26:
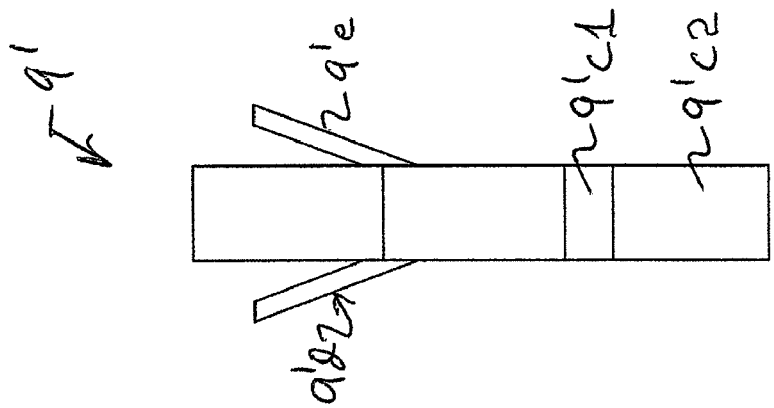
FIG. 26 shows a side view of the trigger shown in FIG. 24.
Figure 25:
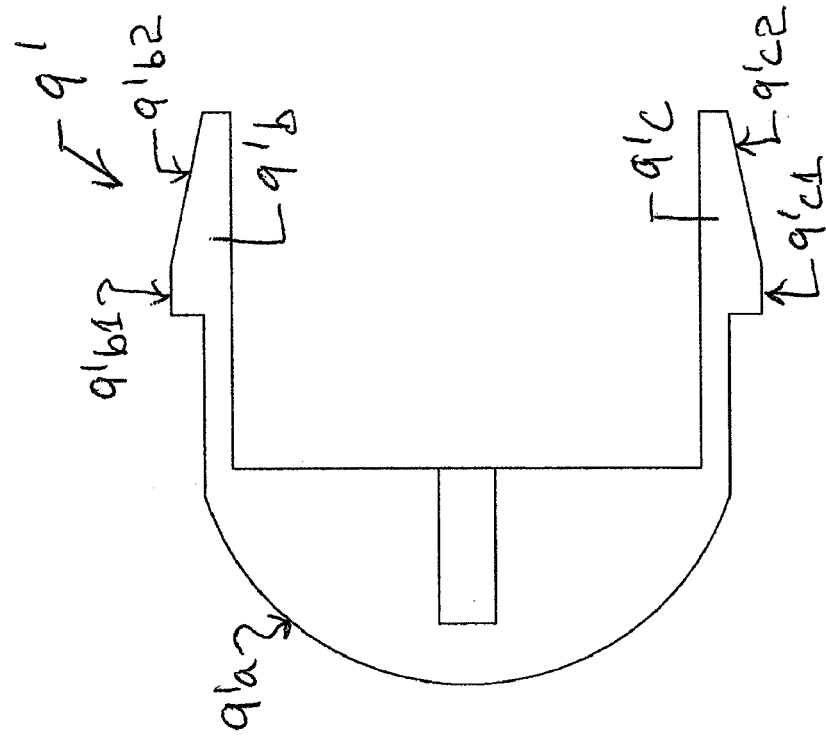
FIG. 25 shows an end view of the trigger shown in FIG. 24.
Figure 24:
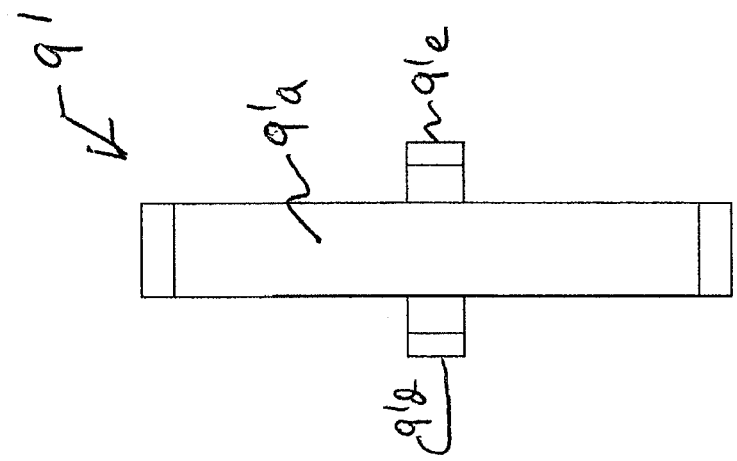
FIG. 24 shows a top view of an optional trigger which used in another embodiment of the lancet device.
Figure 27:
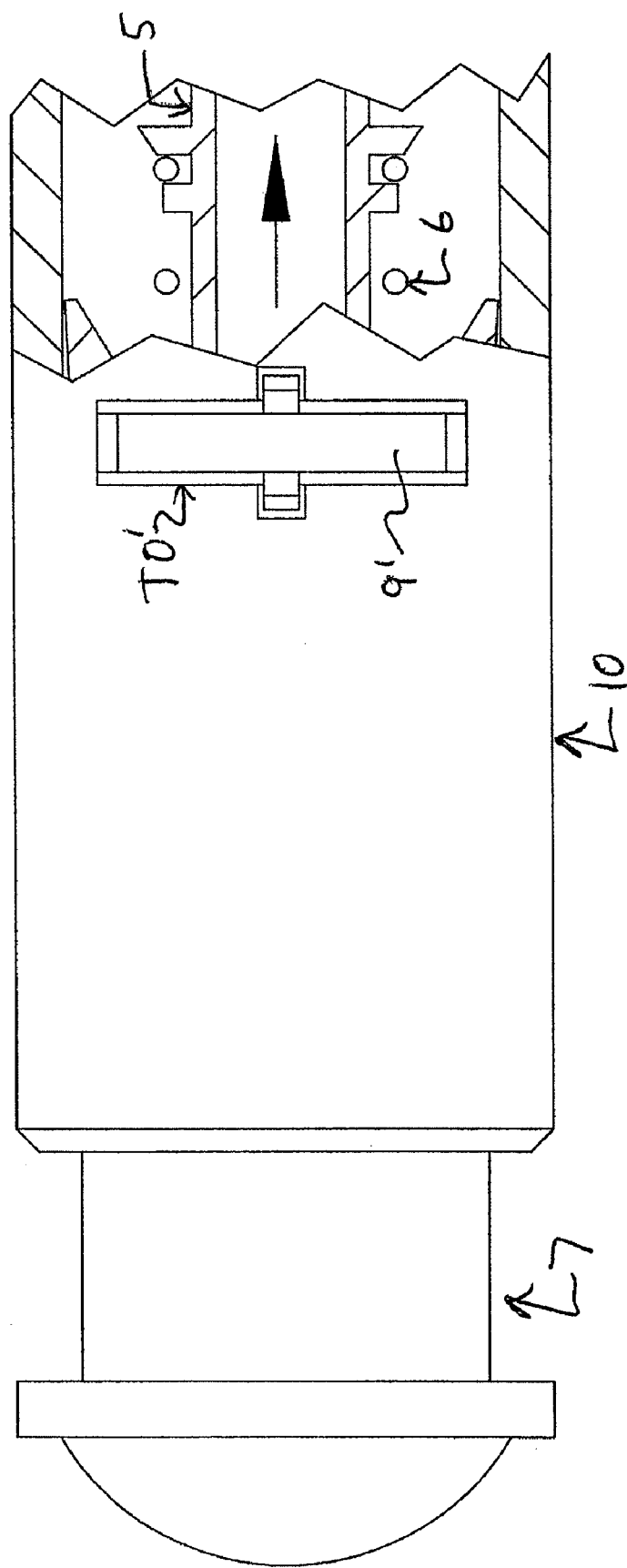
FIG. 27 shows a partial cross-section view of a lancet device embodiment of the type shown in FIG. 21 utilizing the trigger shown in FIGS. 24-26.
Figure 28:
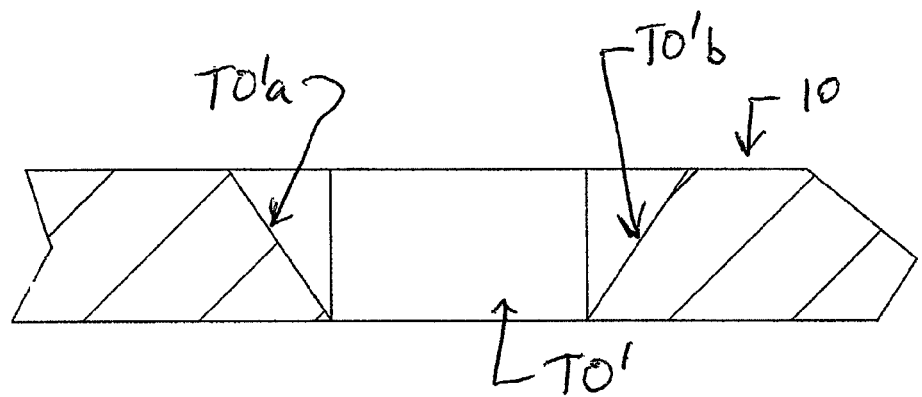
FIG. 28 shows a partial cross-section view of the body used in the lancet device shown in FIG. 27 and illustrates the trigger opening.
Figure 29:
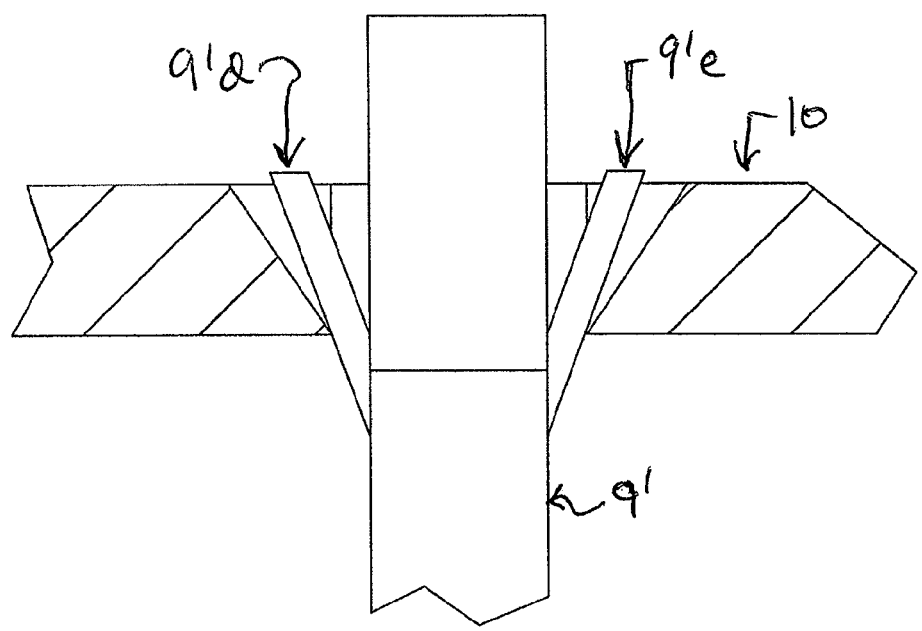
FIG. 29 shows a partial cross-section view of the body used in the lancet device shown in FIG. 27 and partially illustrates the trigger, which is not shown in cross-section, positioned in an initial position in the trigger opening.

As can be seen in FIGS. 1-6, the holding member 5 preferably has a spring 6 mounted thereto. In this regard, the spring 6, which can be made of spring steel, is arranged to surround the holding member 5, just behind a tapered circumferential projection 5d. By way of one non-limiting example, the spring 6 may have a diameter of between approximately 5 mm and approximately 15 mm, a freelength of between approximately 10 mm and approximately 40 mm, and a wire size of between approximately 0.5 mm and 2 mm. This first spring 6 causes (and/or biases) the holding member 5 to move towards an extended position once a trigger (which will be described in detail later on) is activated (causing the movement indicated by arrows in FIG. 5). FIGS. 18 and 19 illustrate one non-limiting embodiment of the trigger 9 which includes a portion that extends into the body 1 and that engages with the deflecting members 7f and 7g, and is movably mounted to a side wall of the body 1. The trigger 9 also has a finger engaging (e.g. push button) portion 9a that can be pushed and/or deflected into the lancet device LD. An alternative embodiment of the trigger is shown in FIGS. 24-26 which utilizes spring members 9'd and 9'e to provide natural elastic biasing properties to bias the trigger 9' towards the position shown in, e.g., FIG. 18. In operation, when force is applied to the finger engaging portion 9a of the trigger 9, the inner portion 9b/9c moves into contact with deflecting members 7f and 7g of the push-button 7 (see e.g., FIGS. 18 and 19).

This causes the deflecting members 7f and 7g to disengage from the projection 5d (see FIG. 5) of the member 5, which allows the holding member 5 to move towards plane P under the action of the spring 6.

Figure 6:
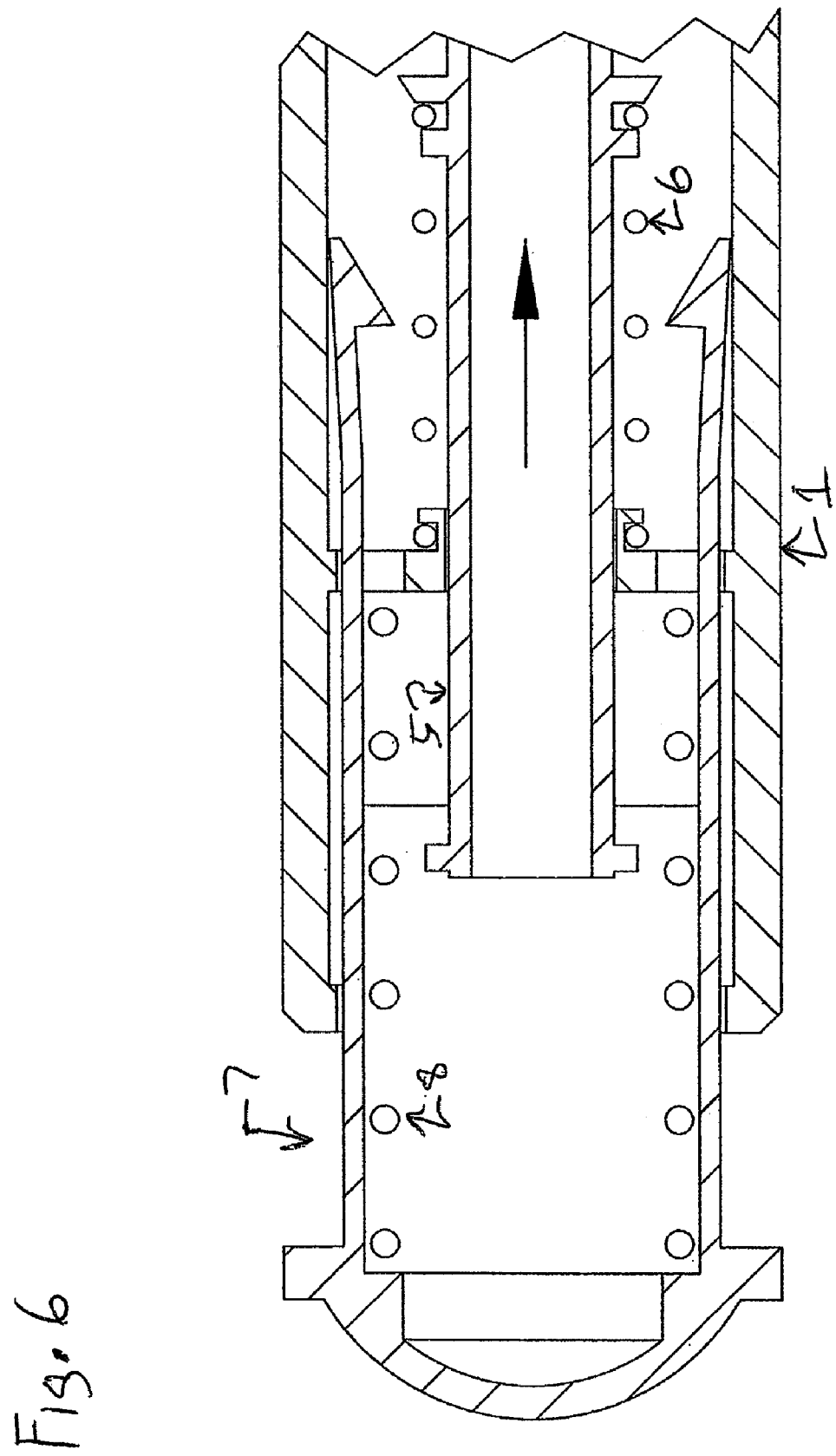
FIG. 6 shows another side cross-section view of the embodiment shown in FIG. 1. The arrow indicates movement of the holding member towards the fully ended and/or puncturing position when the lancet device is fired or triggered.

As discussed above, the spring 6 causes (and/or biases) the holding member 5 to move towards an extended position (see FIG. 6). Another spring 8 is utilized to bias a push-button 7 towards an extended or rearward position. The spring 8 is also sized and configured to cause compression of the first spring 6 when the push-button 7 becomes locked to the holding member 5 (see FIG. 4).

The operation of the lance device shown in FIG. 1-6 will now be described. When a user wishes to use the lancet device LD, the user will typically pick up the lancet device LD in the position shown in FIG. 1. Then, the user will remove the front cover 3 and install a new lancet L. The user will then depress the push-button 7 (see FIG. 2) with, e.g., the user's thumb. As is shown in FIG. 2, this movement of the push-button 7 causes tapered end portions 7d and 7e (and more specifically tapered surfaces 7d1 and 7e1) to contact and be deflected outwardly by the tapered surface 5d1 of the projection 5d. The tapered end portions 7d and 7e then move past the projection 5d and deflect inwardly to an original or relaxed position (see FIG. 3). Of course, the movement shown in FIGS. 2 and 3 will tend to cause the holding member 5 to move a small amount towards the plane P. The spring 6, however, ensures that this movement is kept to a minimum. Once the push-button 7 is fully depressed (see FIG. 3), the user can release the push-button 7. This allows the spring 8 to automatically expand rearwards, and the expansion causes the push-button 7 to move rearwards whereby the portions 7d and 7e become locked to and/or engaged with the projection 5d of the holding member 5 (see FIG. 4). This, in turn, causes the holding member 5 to move to the fully retracted position shown in FIG. 4, and such movement causes the spring 6, which will provide the energy required to move the holding member 5 to the fully extended and/or puncturing position, to be substantially fully compressed. Thus, FIG. 4 shows the lancet device LD in a trigger set and/or cocked position. However, when the user triggers the lancet device LD, i.e., by causing the deflecting members 7d and 7e to move out of engagement with the shoulder/flange/projection 5d (see arrows in FIG. 5), the spring 6 automatically causes the holding member 5 to move to a fully extended position (see FIG. 6). The spring 6 also then causes the holding member 5 to automatically retract axially back within the body 1 to the position shown in FIG. 1. This occurs because the spring 6 has one end, i.e., the right end, coupled to, via two generally circumferential shoulders 5e and 5d, the holding member 5 and another end, i.e., the left end, coupled to and/or fixed between two internal generally circumferential shoulders 1a and 1b of the body 1. The spring 6 can, of course, be connected to these parts in any desired manner. In this way, the lancet needle only momentarily projects past the plane P in the extended position before it is caused to automatically retract back in the lancet device by the spring 6. As a result, the lancet needle only projects past or beyond the plane P for a very brief time (i.e., a fraction of a second when the lancet device LD is triggered) and is otherwise not exposed to a user while the front cover 3 is installed thereon. Accordingly, a user or other innocent bystanders can be protected from being injured unintentionally by an exposed needle.

Figure 7:
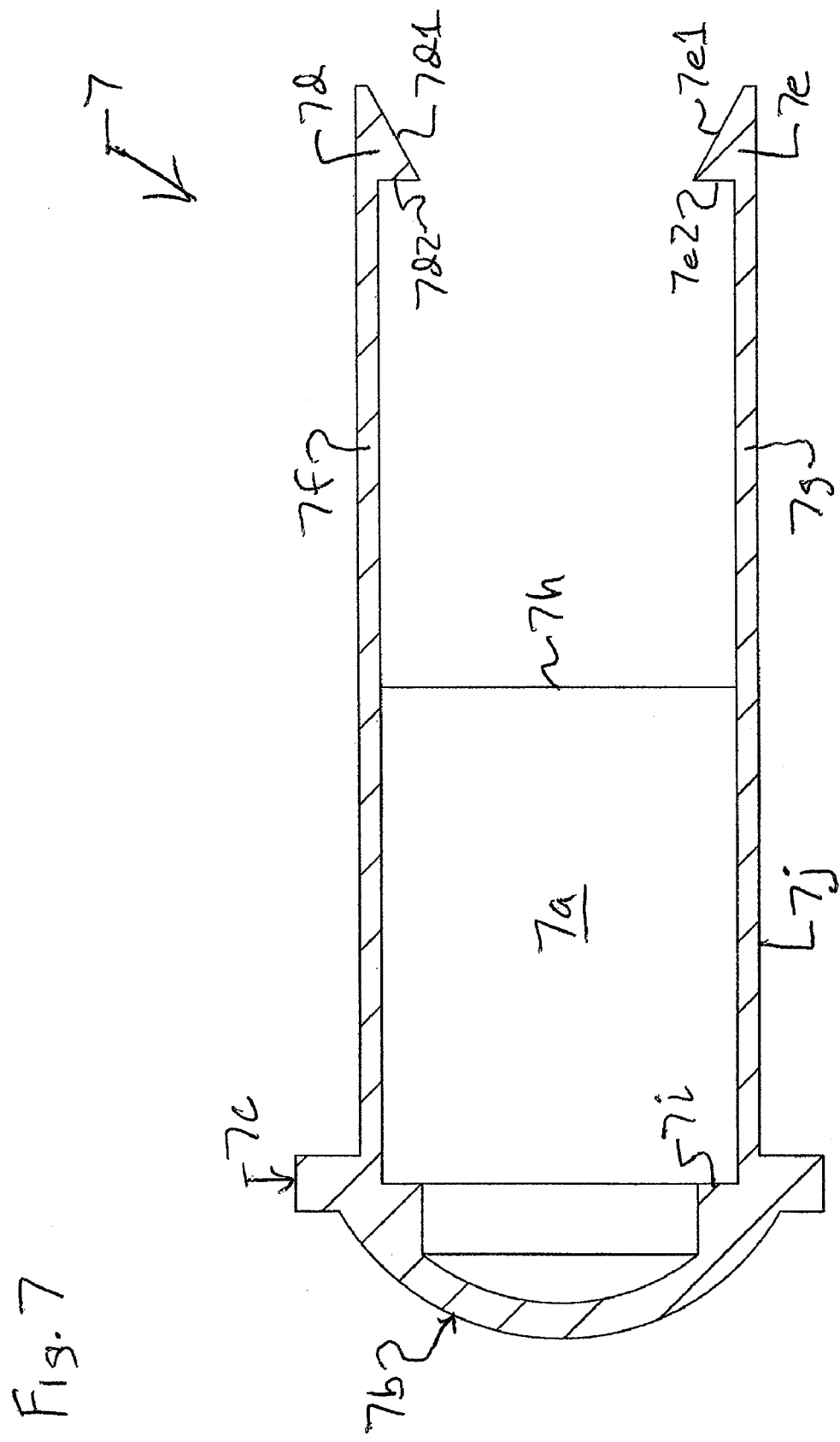
FIG. 7 shows a side cross-section view of the push-button utilized in the embodiment shown in FIG. 1.
Figure 8:
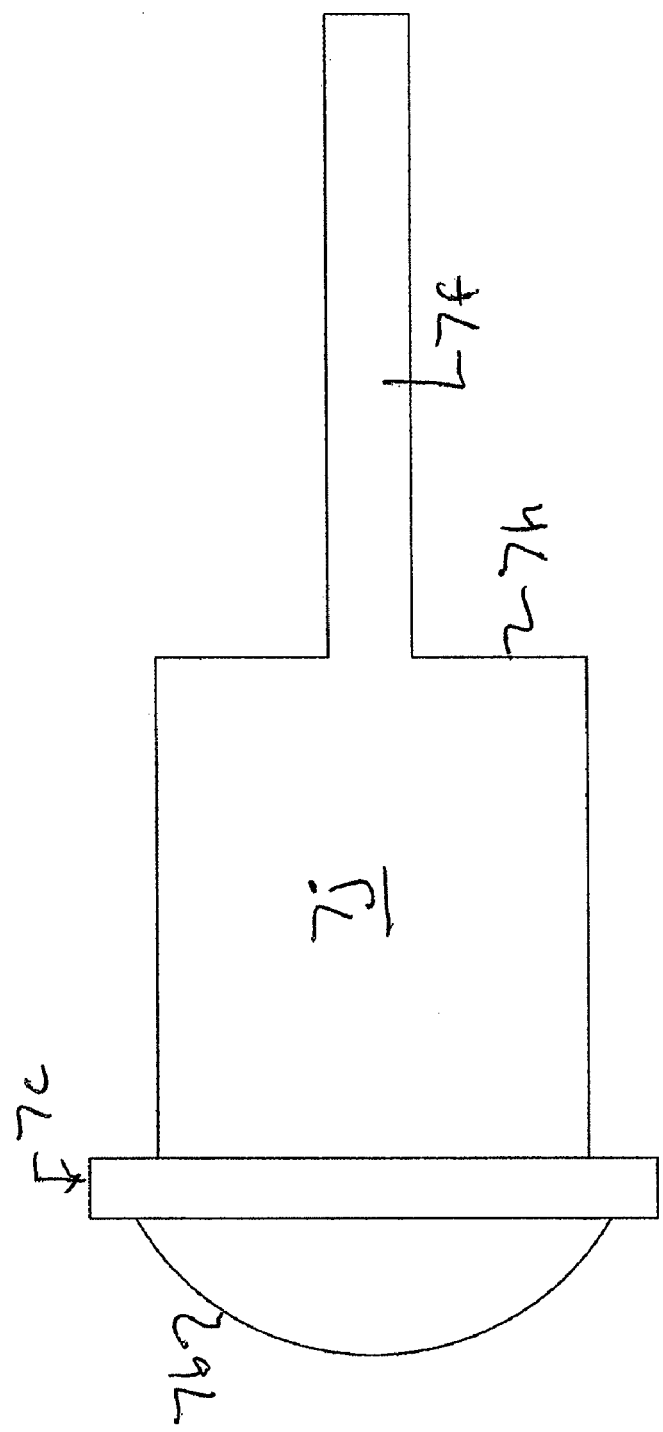
FIG. 8 shows a top view of the push-button shown in FIG. 7.
Figure 9:
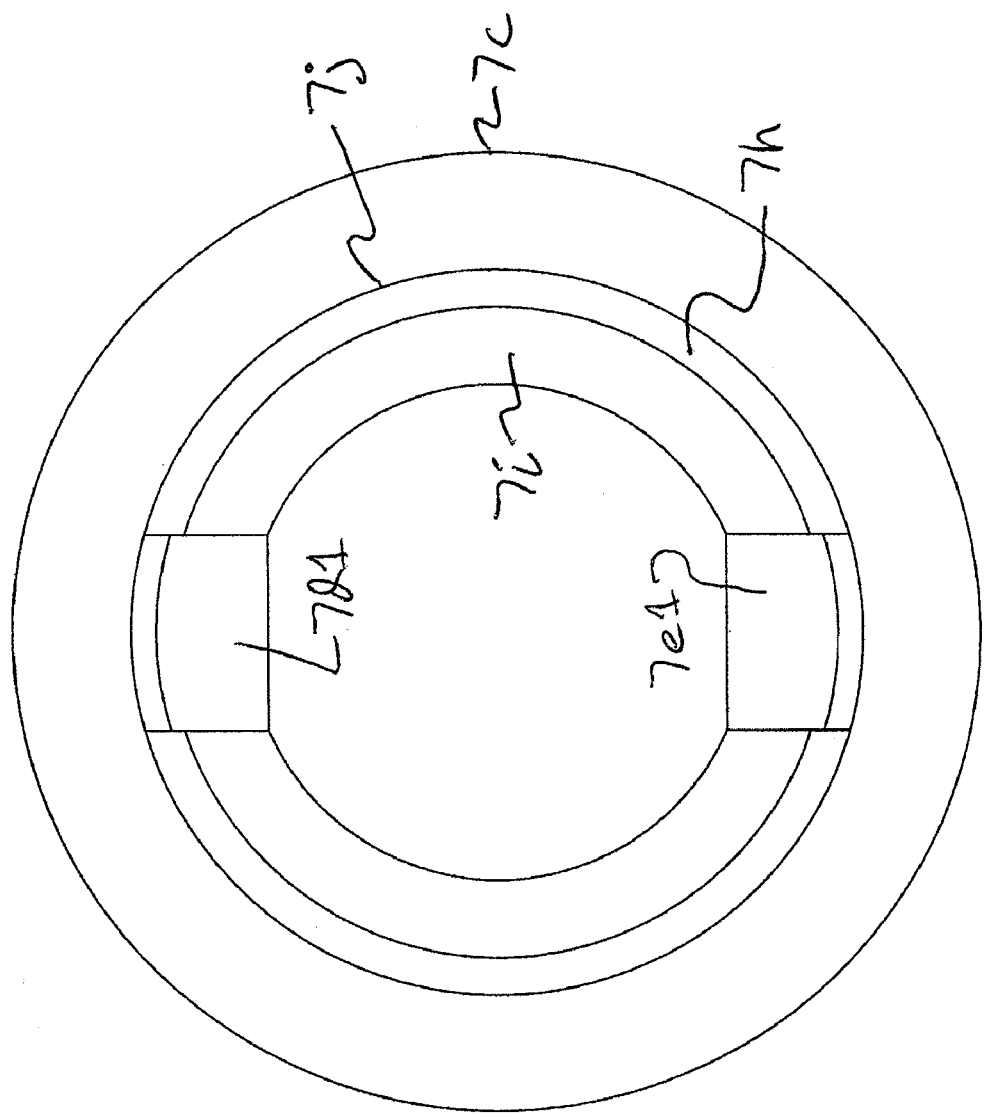
FIG. 9 shows a front end view of the push-button shown in FIGS. 7 and 8.

FIGS. 7-9 show a non-limiting embodiment of the push-button 7 which is utilized on the lancet device LD shown in FIGS. 1-6. The push-button 7 has a cylindrical outer surface 7j which is sized to slide within and/or slidably engage with opening 1f of the body 1, and has a main open area 7a which is sized to house and receive therein the spring 8. An internal shoulder 7i is arranged within the opening 7a and is configured to contact one end of the spring 8. An external shoulder 7c is configured to contact a rear end of the body 1. The push-button 7 also utilizes button portion 7b which is configured to be engaged by a user. The push-button 7 also utilizes two oppositely arranged deflecting/locking portions 7f and 7g which extend beyond an axial edge 7h. Deflecting/locking portion 7f has an engaging/locking portion 7d arranged at a free end thereof. The engaging/locking portion 7d includes a tapered surface 7d1 which is configured to slidably engage with the tapered surface 5d1 and a locking shoulder 7d2 which is configured to engage with and/or lock with the projection 5d. Deflecting/locking portion 7g has an engaging/locking portion 7e arranged at a free end thereof. The engaging/locking portion 7e similarly includes a tapered surface 7e1 which is configured to slidably engage with the tapered surface 5d1 and a locking shoulder 7e2 which is configured to engage with and/or lock with the projection 5d.

Figure 1:
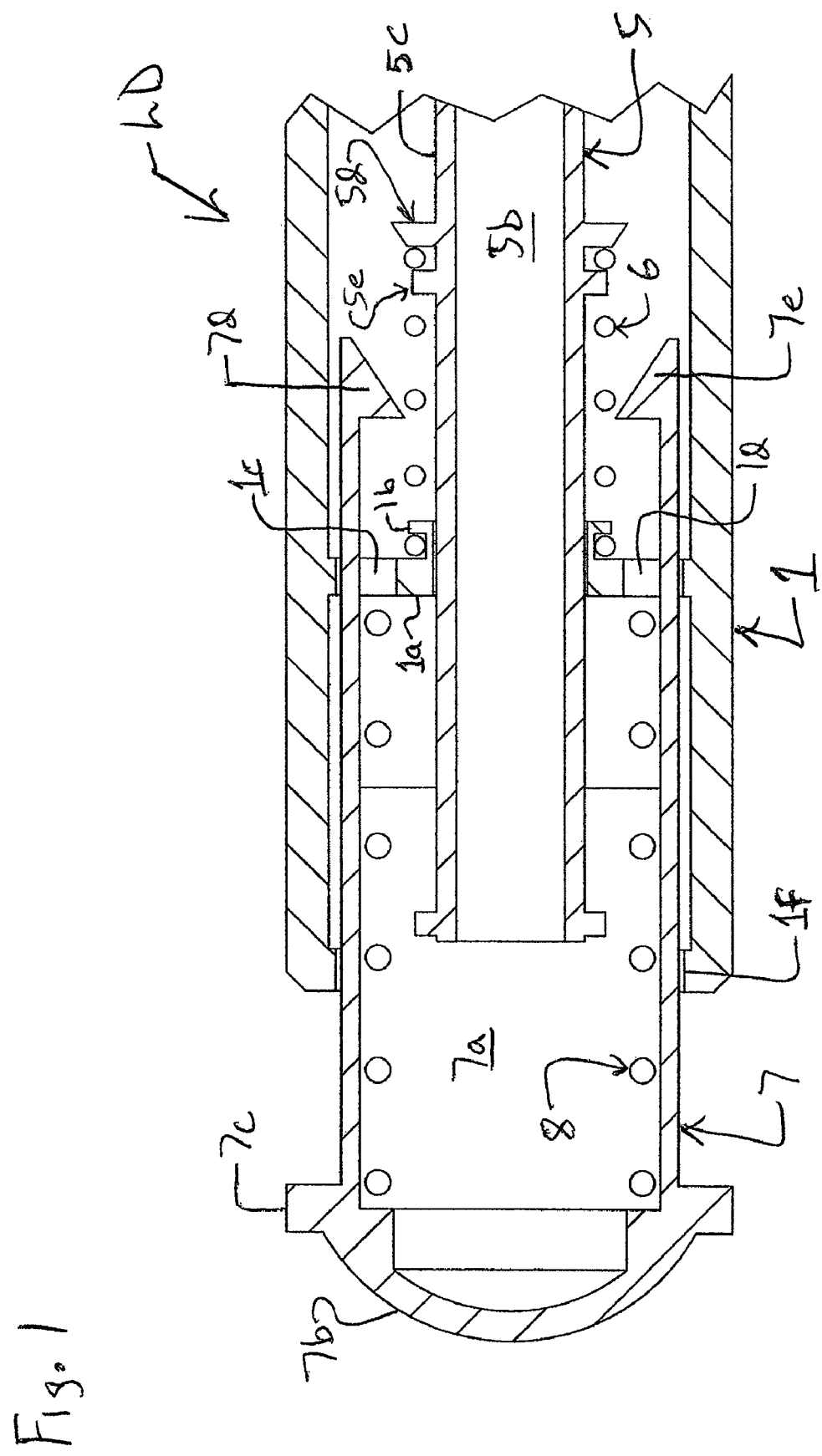
FIG. 1 shows a partial side cross-section view of a first embodiment of the lancet device. This embodiment utilizes a push-button trigger setting and/or cocking system. The front portion of the lancet device is not shown.
Figure 2:
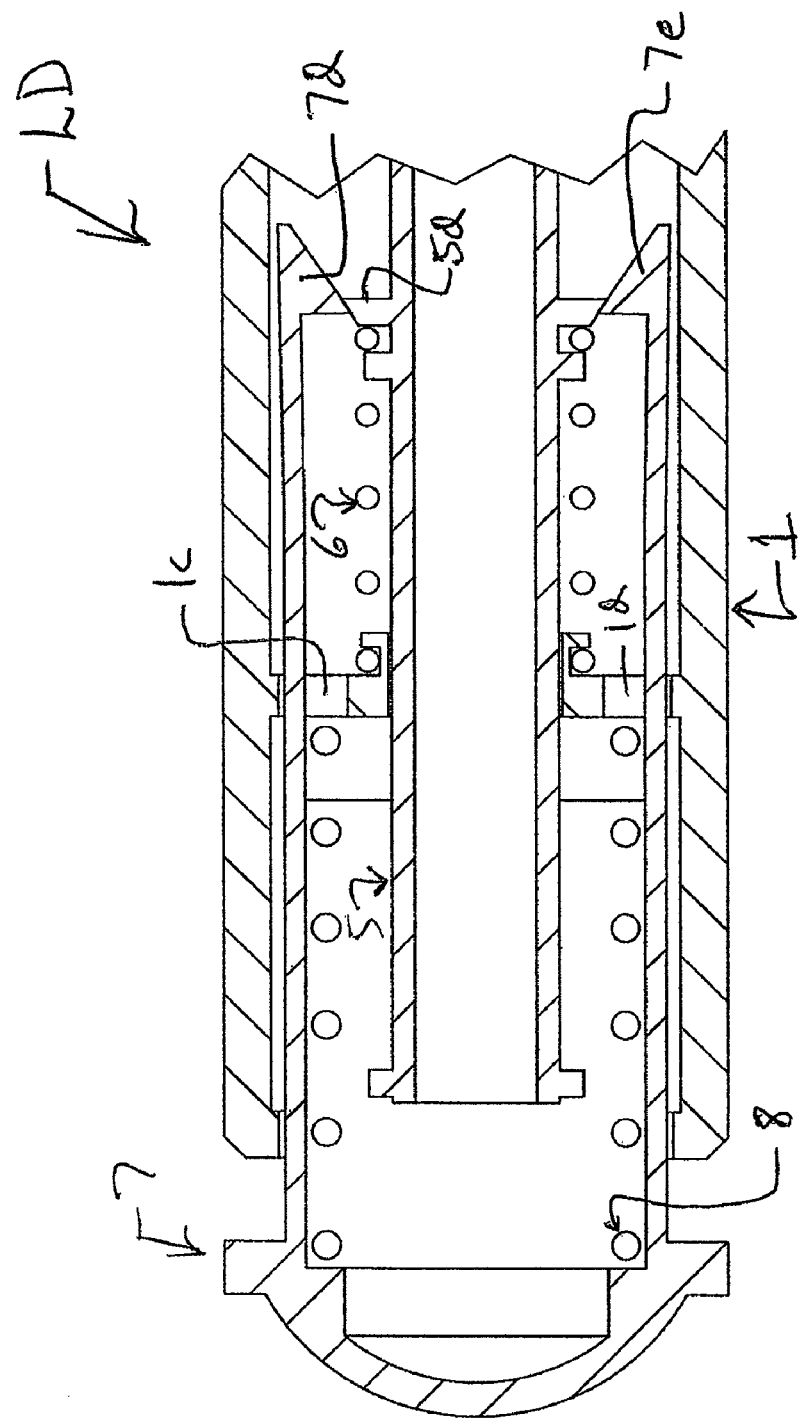
FIG. 2 shows another side cross-section view of the embodiment shown in FIG. 1. The push-button has been depressed and is shown in a position prior to becoming locked to the holding member.
Figure 10:
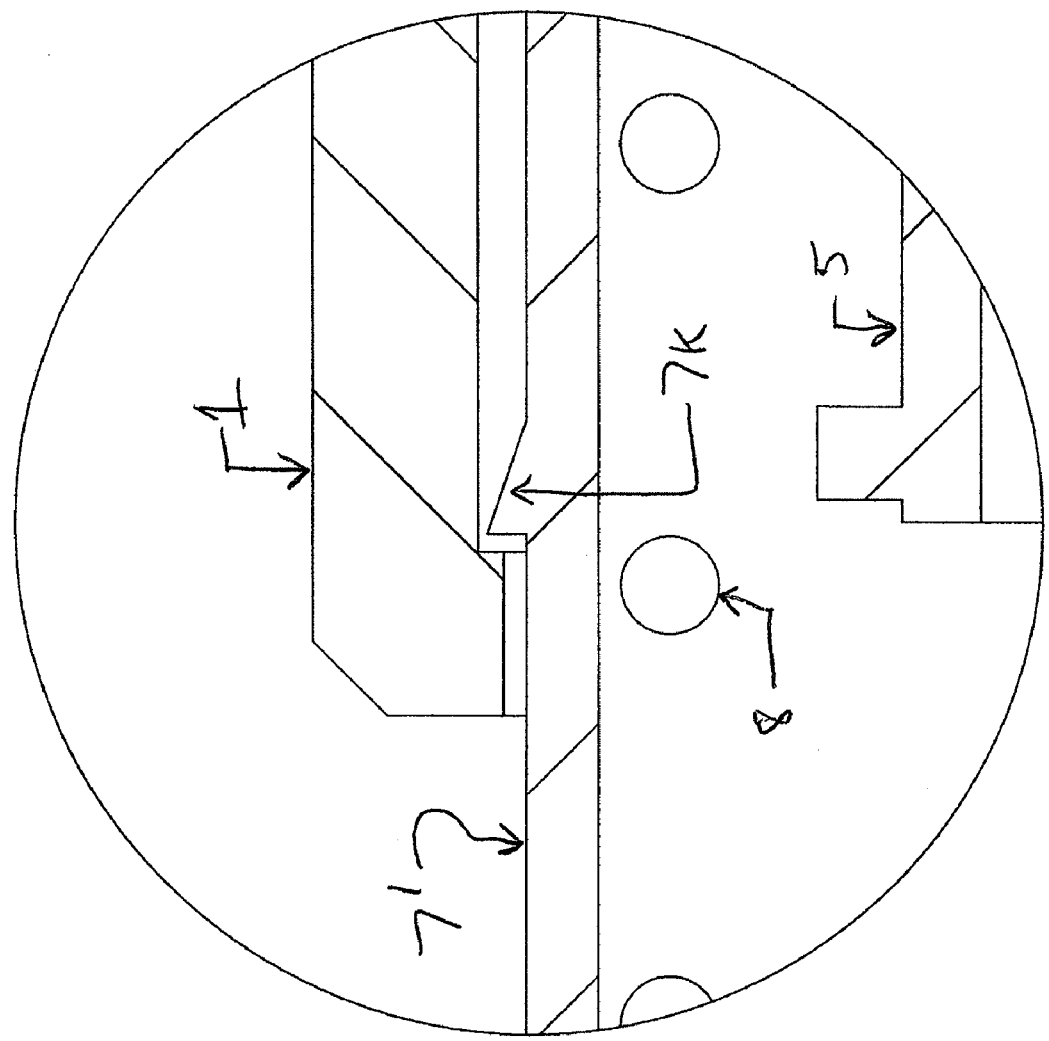
FIG. 10 shows a partial enlarged view of the lancet device of FIG. 1 utilizing an optional push-button configuration which includes a tapered circumferential projection which allows the push-button to be slid into the lancet device from a back end, which also prevents its removal once inserted, and which functions to limit rearward movement of the push-button.

FIG. 10 shows a partial enlarged view of the lancet device LD of FIG. 1 utilizing an optional push-button 7' configuration which substantially similar to push-button 7 but also includes a tapered circumferential projection 7k which allows the push-button 7' to be slid into the opening 1f lancet device LD from a back end, which also prevents its removal once inserted, and which functions to limit rearward movement of the push-button 7'. Of course, the projection 7k need not be a single projection which extends completely around the circumference of surface 7j and can instead be a plurality of spaced-apart projections.

Figure 11:
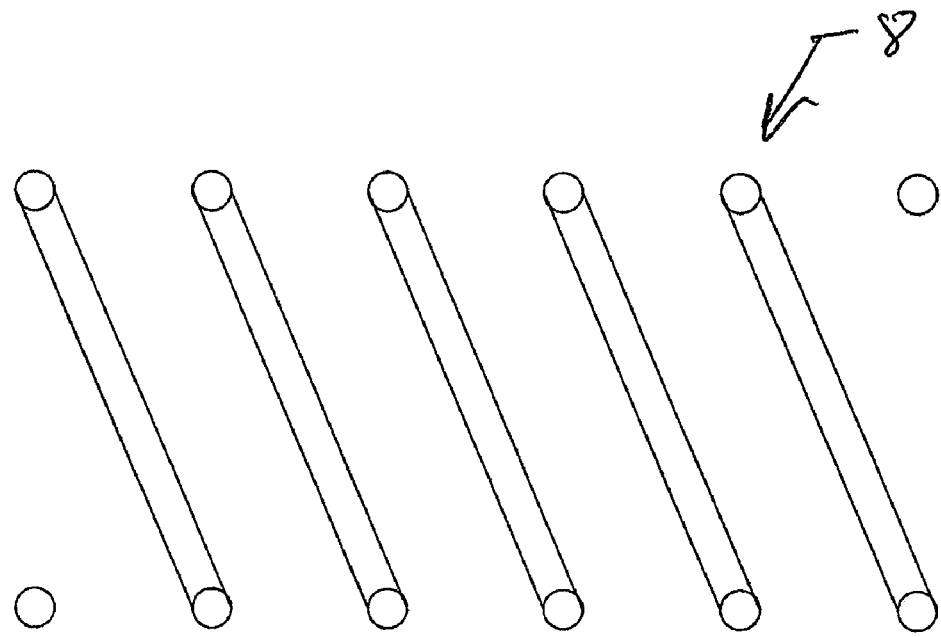
FIG. 11 shows a side cross-section view of the push-button spring used in the embodiment shown in FIG. 1.

FIG. 11 shows a side cross-section view of the push-button spring 8 which is utilized in the lancet device LD of FIG. 1. The spring 8 is preferably a helical compression spring which, when expanded, is capable of causing full compression of the holding member spring 6.

Figure 12:
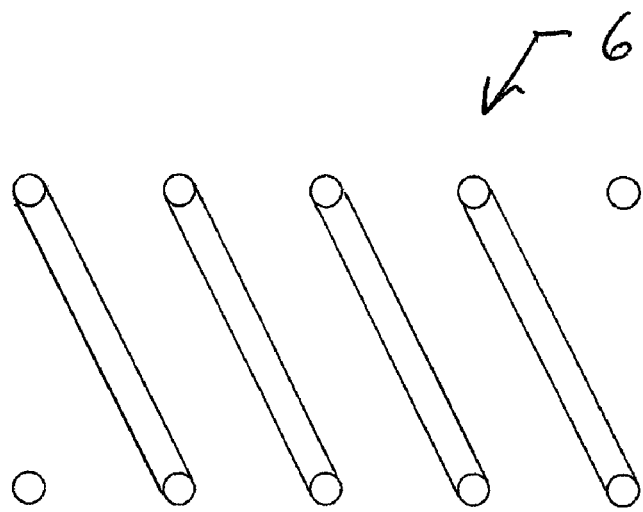
FIG. 12 shows a side cross-section view of the holding member spring used in the embodiment shown in FIG. 1.

FIG. 12 shows a side cross-section view of the holding member spring 6 which is utilized in the lancet device LD of FIG. 1. The spring 6 is preferably a helical compression spring which is capable of the holding member 5 to move to the fully retracted position and to also retract the holding member 5 thereafter.

FIGS. 13-14 show various views of the body 1 which is utilized in the lancet device LD of FIG. 1. The body 1 has a rear opening 1f which is sized and shaped to receive therein the push-button 7. The body 1 includes a rear flange support 1a whose central through opening 1e is sized and configured to receive therein and/or slidably support the rear end of the holding member 5. The rear facing annular surface of the support 1a serves a contact surface for the forward end of the spring 8 while the forward facing annular surface the support 1a serves a contact surface for the rear end of the spring 6. A circumferential retaining flange/projection 1b is coupled to the support 1a and serves to secure and/or fix the rear end of the spring 6 to the body 1. The body 1 also has two generally rectangular openings 1c and 1d which are respectively sized and configured to receive therein the deflecting portions 7f and 7g of the push-button 7.

FIG. 15 shows an end cross-section view of a preferred two-piece body 1'. The body 1' can be identical to the body 1 shown in FIG. 13 except that it comprises a two-piece construction made up of parts 1'x and 1'y whose seam extends through the openings 1c and 1d.

Figure 16:
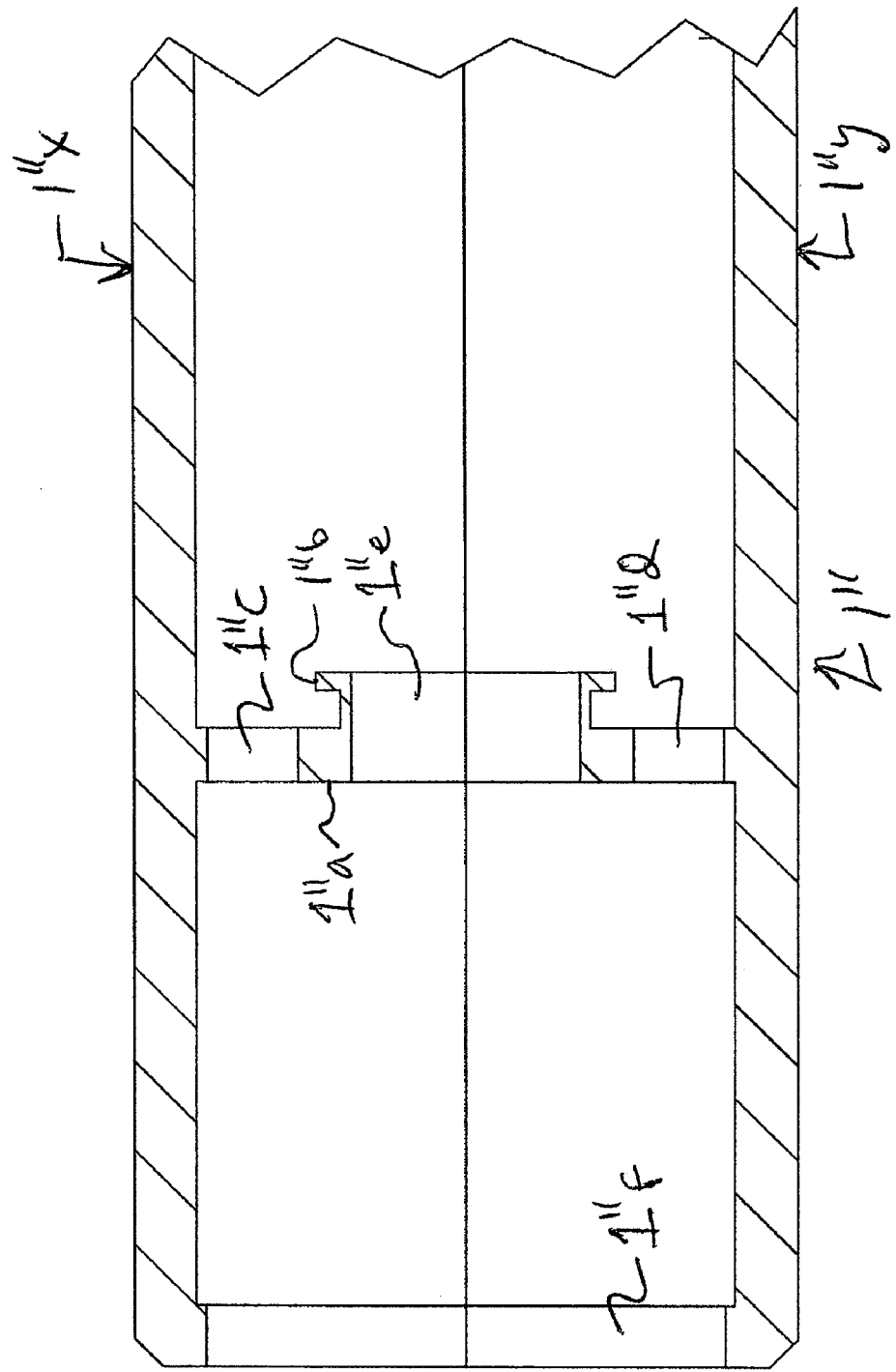
FIG. 16 shows a side cross-section view of an optional two-piece body which can be used in the embodiment shown in FIG. 1.

FIG. 16 shows a side cross-section view of an optional two-piece body 1''. The body 1'' can be identical to the body 1 shown in FIG. 13 except that it comprises a two-piece construction made up of parts 1''x and 1''y whose seam extends perpendicular to the openings 1c and 1d. The body 1'' has a rear opening 1"*f* which is sized and shaped to receive therein the push-button 7. The body 1 includes a rear flange support 1"*a* whose central through opening 1"*e* is sized and configured to receive therein and/or slidably support the rear end of the holding member 5. The rear facing annular surface of the support 1"*a* serves a contact surface for the forward end of the spring 8 while the forward facing annular surface the support 1"*a* serves a contact surface for the rear end of the spring 6. A circumferential retaining flange/projection 1"*b* is coupled to the support 1*a* and serves to secure and/or fix the rear end of the spring 6 to the body 1". The body 1" also has two generally rectangular openings 1"*c* and 1"*d* which are respectively sized and configured to receive therein the deflecting portions 7*f* and 7*g* of the push-button 7.

Figure 17:
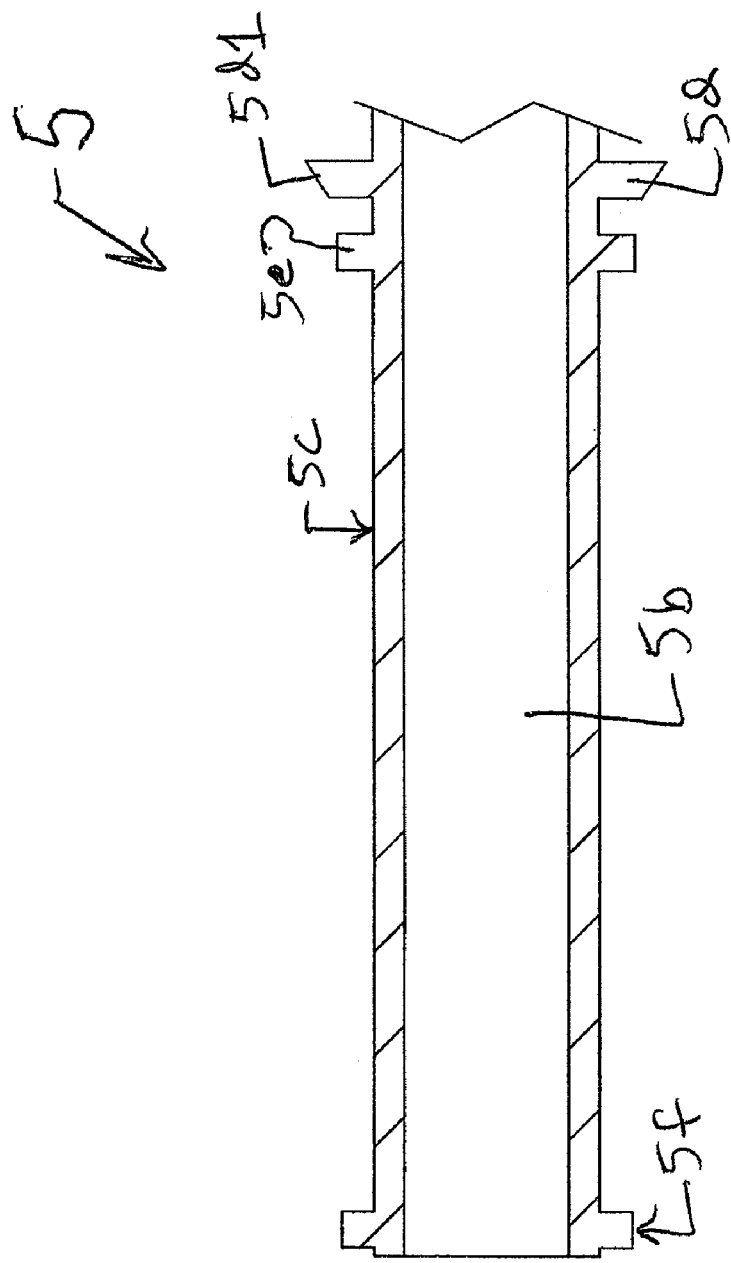
FIG. 17 shows a side cross-section view of the holding member used in the embodiment shown in FIG. 1.
Figure 23:
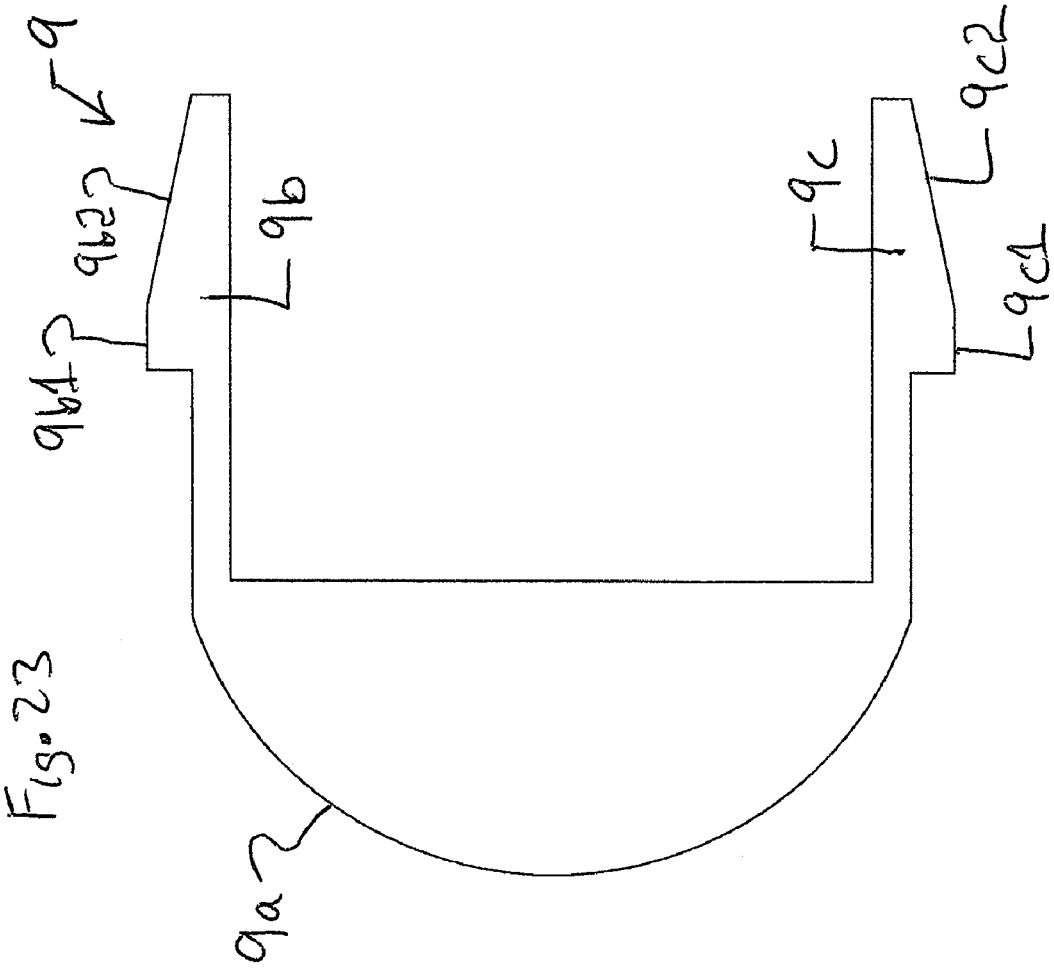
FIG. 23 shows an end view of the trigger shown in FIG. 22.
Figure 22:
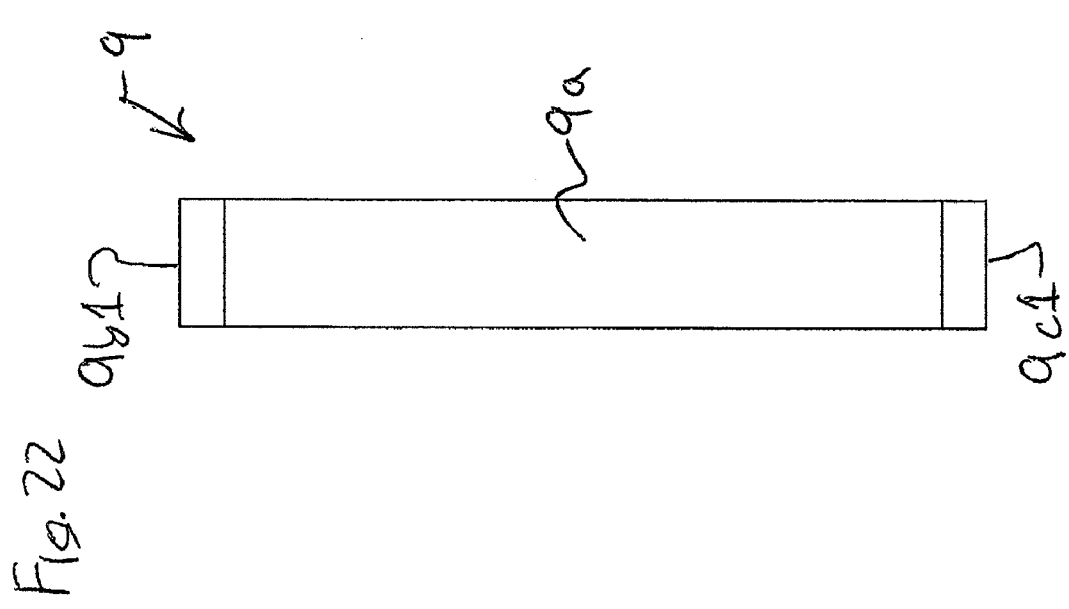
FIG. 22 shows a top view of the trigger used in the embodiment shown in FIGS. 18-22.

FIG. 17 shows a side cross-section view of the rear portion of the holding member 5 used in the embodiment shown in FIGS. 1-6. The holding member 5 is a generally cylindrical tubular integral or one-piece member which utilizes a front opening 5*a* (see FIG. 31), a rear opening 5*b*, and an optional rear projection 5*f* to limit axial movement of the holding member 5 in the direction of the plane P. The member 5 also has a generally cylindrical outer surface 5*c* which is sized and configured to slidably engage with the openings 1*e* and 1*k*. Two cylindrical projections/flanges/shoulders 5*e* and 5*d* are arranged between the front and rear ends of the member 6. These projections/flanges/shoulders 5*e* and 5*d* are spaced apart and configured to fixedly secure the front end of spring 6 to the holding member 5. The projection/flange/shoulder 5*d* also includes a tapered surface 5*d*1 which is configured to be contacted by the tapered surfaces 7*d*1 and 7*e*1 of the push-button 7. As explained above, this contact causes the portions 7*d* and 7*e* to be deflected outwards and allows them to move axially past the projection 5*d* when the push-button is depressed. The front portion (not shown in FIG. 17) of the holding member 5 can be similar to conventional lancet devices. Preferably, the front portion of the holding member 5 has a configuration similar to that shown in FIG. 31. Of course, the member 5 need not be a one-piece integral member and instead constitute one or more members.

FIGS. 18-23 show one non-limiting way in which the deflecting members 7*f* and 79 of the push-button 7 can be deflected and/or unlocked from the holding member 5. A trigger 9, which includes a portion that extends into the body 1 and that engages with the deflecting members 7*f* and 7*g*, is movably mounted to a side wall of the body 1. A trigger opening TO (see FIG. 21) is arranged in the side wall of the body 1 and is sized and configured to receive the trigger 9. The trigger 9 also has a finger engaging (e.g. push button) portion 9*a* that can be pushed and/or deflected into the lancet device LD. Two portions 9*b* and 9*c* extend inwardly from the button portion 9*a*. Portion 9*b* includes a tapered surface 9*b*2 which slidably engages with an inner surface of portion 7*f* to cause its outward deflection and a planar surface 9*b*1 which maintains the deflection of member 7*f* upon further inward movement of the trigger 9. Portion 9*c* similarly includes a tapered surface 9*c*2 which slidably engages with an inner surface of portion 7*g* to cause its outward deflection and a planar surface 9*c*1 which maintains the deflection of member 7*g* upon further inward movement of the trigger 9. It is preferable, however, that the surfaces 9*b*1 and 9*c*1 not come into engagement with the inner surfaces of the members 7*f* and 7*g* so that the trigger 9 will be biased away from inward movement due to the horizontal force component created by engagement between the surfaces 9*b*2 and 9*c*2 and the inner surfaces of members 7*f* and 7*g*. Alternatively, one or more springs can be utilized to bias the trigger 9 towards the position shown in FIG. 18. If the spring(s) is utilized, the surfaces 9*b*1 and 9*c*1 can come into engagement with the inner surfaces of the members 7*f* and 7*g*.

FIGS. 24-29 show another non-limiting way in which the deflecting members 7*f* and 7*g* of the push-button 7 can be deflected and/or unlocked from the holding member 5. An alternative trigger 9', which includes a portion that extends into the body 1 and that engages with the deflecting members 7*f* and 7*g*, is movably mounted to a side wall of the body 1. A trigger opening TO' (see FIG. 27) is arranged in the side wall of the body 1 and is sized and configured to receive the trigger 9'. The alternative embodiment of the trigger 9' is shown in detail FIGS. 24-26. The trigger 9', like trigger 9, is an integrally formed and/or one-piece member and utilizes spring members 9'*d* and 9'*e* to provide natural elastic biasing properties to bias the trigger 9' towards the position shown in, e.g., FIG. 18. In operation, when force is applied to the finger engaging portion 9'*a* of the trigger 9', the inner portion 9'*b*/9'*c* moves into contact with deflecting members 7*f* and 7*g* of the push-button 7 (see e.g., FIGS. 18 and 19). This causes the deflecting members 7*f* and 7*g* to disengage from the projection 5*d* (see FIG. 5) of the body 1, which allows the holding member 5 to move towards plane P under the action of the spring 6. As was the case with trigger 9, portions 9'*b* and 9'*c* extend inwardly from the button portion 9'*a*. Portion 9'*b* includes a tapered surface 9'*b*2 which slidably engages with an inner surface of portion 7*f* to cause its outward deflection and a planar surface 9'*b*1 which maintains the deflection of member 7*f* upon further inward movement of the trigger 9'. Portion 9'*c* similarly includes a tapered surface 9'*c*2 which slidably engages with an inner surface of portion 7*g* to cause its outward deflection and a planar surface 9'*c*1 which maintains the deflection of member 7*g* upon further inward movement of the trigger 9'. As can be send in FIGS. 28-29, the trigger 9' is biased towards the position shown in FIG. 18 (i.e., a non-triggered or original position) by engagement between deflectable spring members 9'*d* and 9'*e* and tapered surfaces TO'*a* and TO'*b* of the body 1.

FIGS. 30-38 show one non-limiting preferred embodiment of the lancet device LD which utilizes a number of features shown in FIGS. 1-29. Although the invention contemplates using the features shown in FIGS. 1-29 on a lancet device which merely utilizes a front cap which may or may not have depth adjustment, the invention preferably utilizes a depth adjustment system. FIGS. 20-38 show one such non-limiting arrangement. In this embodiment, a body 1 has a front end on which is removably mounted a front cap 3 and a rear end on which is movably mounted a back cap or push-button 7. An intermediate member 2 is movably mounted to the front end of the body 1 and is disposed between the front cap 3 and the body 1. The member 2 provides for lancet needle depth adjustment. In this regard, the intermediate member 2 is preferably mounted to the body 1 so as to at least partially rotate in each of two directions. Of course, the intermediate member 2 can be mounted to the body 1 in any desired manner (i.e., with or without threads) provided it functions properly in the intended manner, i.e., provided it moves axially forwards and backwards to provide depth adjustment. To ensure that the intermediate member 2 is axially retained to the body 1, yet allowed to rotate with respect to the lancet device body 1, the intermediate member 2 has internal threads 2*a* which engage external threads 1*h* of the body 1. The threads of the body 1 and the intermediate member 2 can be of any conventionally known type. The intermediate member 2 also includes a chamfered section having raised projections or a knurl 2*b* which allows a user to more securely grip (i.e., by providing a high friction gripping surface) the intermediate member 2.

The intermediate member 2 additionally also has an external generally circumferential projection 2c that can releasably engage with an internal circumferential recess 3a of the front cap 3.

Figure 30:
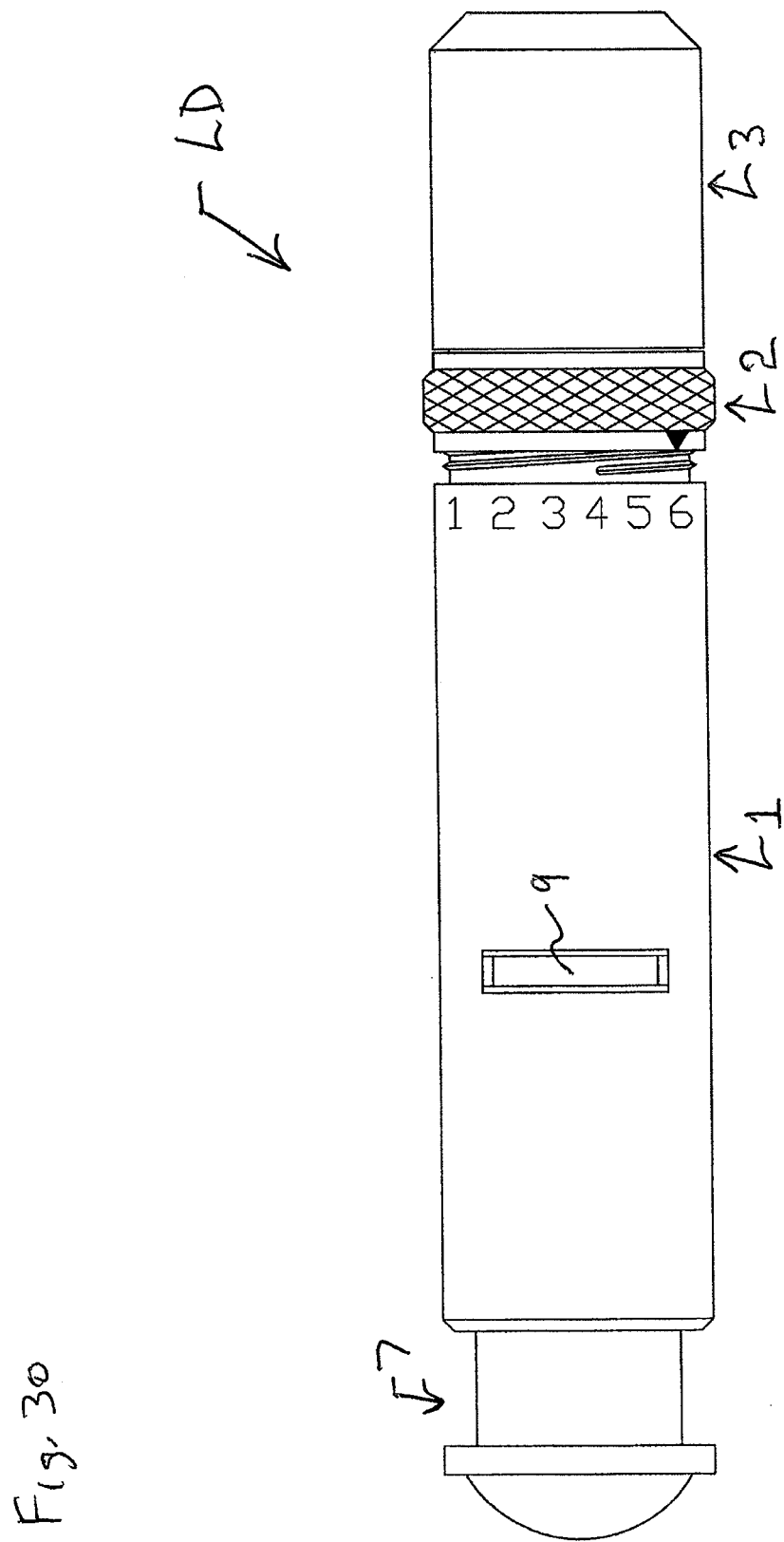
FIG. 30 shows a side view of a complete lancet device utilizing the features shown in FIGS. 1-23.
Figure 31:
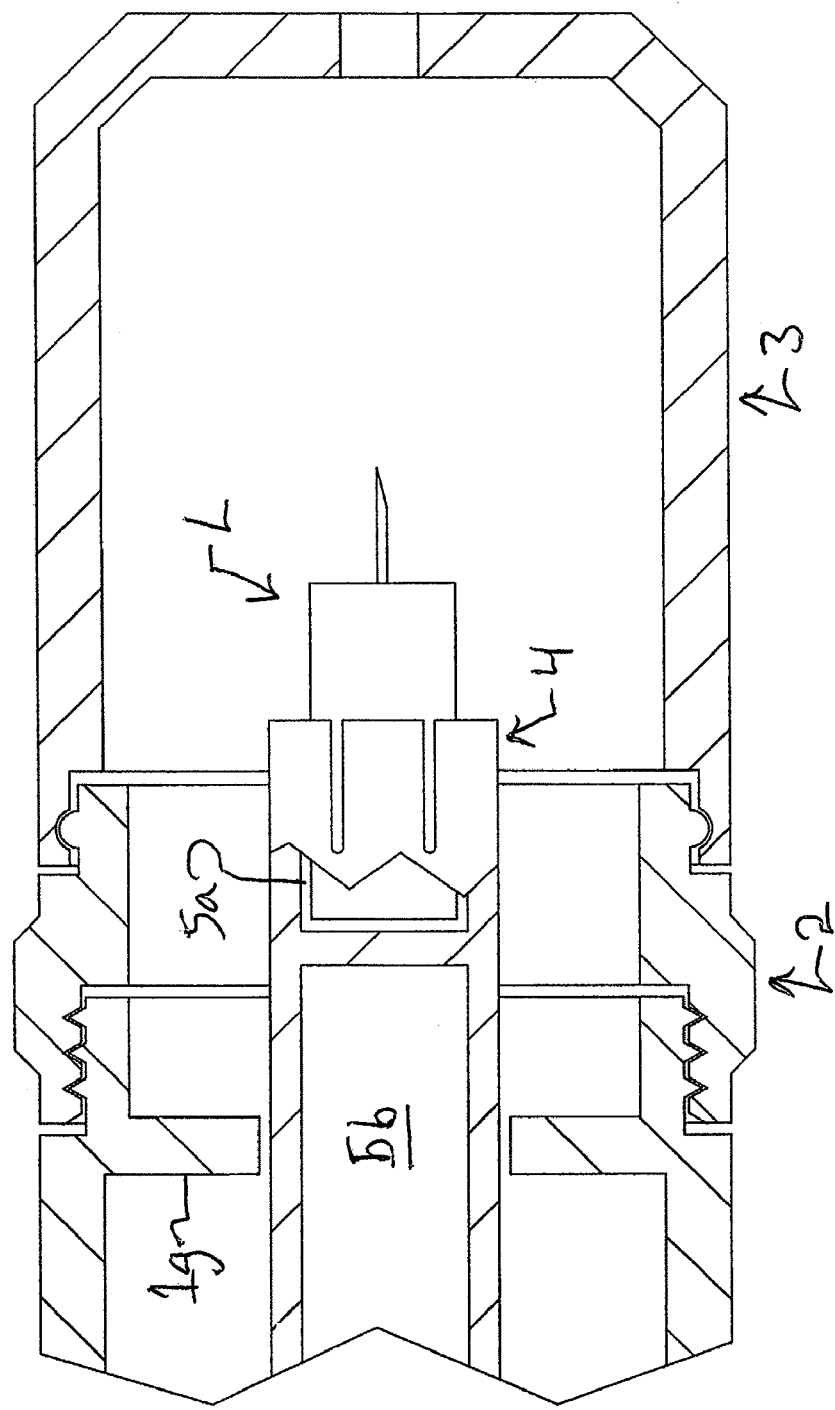
FIG. 31 shows a partial cross-section view of a front portion of the lancet device shown in FIG. 30. The front portion of the holding member and the lancet are not shown in cross-section.

The operation of the lance device LD shown in FIG. 30 will now be described. When a user wishes to use the lancet device LD, the user will typically pick up the lancet device LD in the position shown in FIGS. 1 and 30. Then, the user will remove the front cover 3 and install a new lancet L. The user will then adjust the depth of penetration by rotating member 2 relative to the body 1 in order to align the arrow indicator of member 2 with one of the setting indicia of the body 1. FIG. 30 shows the arrow of member 2 aligned with indicia "6" of the body 1 which results in a in a lowed depth of penetration than indicia "1" which results in the deepest depth of penetration of the lancet needle. The user will then depress the push-button 7 with the user's thumb while gripping the body 1 with the user's palm. FIG. 2 shows such inward movement of the push-button 7. As is shown in FIG. 2, this movement of the push-button 7 causes tapered end portions 7d and 7e (and more specifically tapered surfaces 7d1 and 7e1) to contact and be deflected outwardly by the tapered surface 5d1 of the projection 5d. The tapered end portions 7d and 7e then move past the projection 5d and deflect inwardly to an original position (see FIG. 3). Of course, the movement shown in FIGS. 2 and 3 will tend to cause the holding member 5 to move a small amount towards the plane P. The spring 6, however, ensures that this movement is kept to a minimum. Once the push-button 7 is fully depressed (see FIG. 3), the user can release the push-button 7. This allows the spring 8 to automatically expand rearwards. This axial expansion causes the push-button 7 to move rearwards whereby the portions 7d and 7e to become locked to and/or engaged with the projection 5d of the holding member 5. This expansion of the spring 8 while the push-button 7 is locked to the holding member 5, in turn, causes the holding member 5 to move to the fully retracted position shown in FIG. 4. This, in turn, causes the spring 6, which will provide the energy required to move the holding member 6 to the fully extended and/or puncturing position, to be substantially fully compressed. Thus, FIG. 4 shows the lancet device LD is a trigger set and/or cocked position. However, when the user triggers the lancet device LD, i.e., by depressing trigger 9 (which causes the deflecting members 7d and 7e to move out of engagement with the shoulder/flange/projection 5d (see FIG. 5)), the spring 6 automatically causes the holding member 5 to move to a fully extended position (see FIG. 6). In this regard, the fully extended position can either by contact between projection 5f and shoulder 1a, or alternatively by contact between the lancet L and the inner surface of the front cap 3 (as in known in prior art devices), or by contact between a movable stop surface and a fixed stop surface 1g. Non-limiting examples of this latter configuration are disclosed in e.g., U.S. Pat. No. 2005/0038465 to SCHRAGA and/or U.S. Pat. No. 2005/0234495 to SCHRAGA, the disclosures of each of these documents are hereby expressly incorporated by reference in their entireties. The spring 6 also causes the holding member 5 to automatically retract axially back within the body 1 to the position shown in FIG. 1. This occurs because the spring 6 has one end, i.e., the right end, coupled to, via two generally circumferential shoulders 5e and 5d, the holding member 5 and another end, i.e., the left end, coupled to and/or fixed between two internal generally circumferential shoulders 1a and 1b of the body 1. The spring 6 can, of course, be connected to these parts in any desired manner. In this way, the lancet needle only momentarily projects past the plane P in the extended position before it is caused to automatically retract back in the lancet device by the spring 6. As a result, the lancet needle only projects past or beyond the plane P for a very brief time (i.e., a fraction of a second when the lancet device LD is triggered) and is otherwise not exposed to a user while the front cover 3 is installed thereon. Accordingly, a user or other innocent bystanders can be protected from being injured unintentionally by an exposed needle.

As can be seen in FIGS. 32, 33 and 36-38, the body 1 has external threads 1h and a deflecting member 1i that includes a projection 1j. As explained above, the threads 1h are configured to engage internal threads 2a of the intermediate member 2. The intermediate member 2 also includes internal recesses 2d which receive therein the projection 1j depending on the particular rotational position of the intermediate member 2. In this way, as the intermediate member 2 rotates or threadably engages with the body 1a clicking sound will result as the projection 1j selectively sequentially engages with each of the recesses d. Furthermore, engagement between the projection 1j and a particular recess 2d results in a different overall length for the lancet device LD and also a different depth setting position. Moreover, engagement between the projection 1j and a particular recess 2d results in a depth set position that is locked or temporarily set until the intermediate member 2 is rotated to another position determined by engagement between the projection 1j and another recess 2d. In order to ensure that the projection 1j can releasably engage with each of the recesses 2d, the member 1i is made deflectable by its integral connection (i.e., a living hinge connection provided for by the natural elasticity of the material of the body and two slots separating the sides of the member 1i) with the body 1. Of course, the invention also contemplates using the projection on the intermediate member 2 and the recesses on the body 1. As with many of the previously described embodiments, the lancet L can be securely and axially retained within opening 5a of the holding member 5 via, e.g., projections (not shown) which have sharp ends for gripping the lancet L. Slots formed in the front portion 4 allow the opening 5a to expand and contract upon insertion and removal of the lancet L and allow the end 4 to act as spring fingers.

Figure 39:
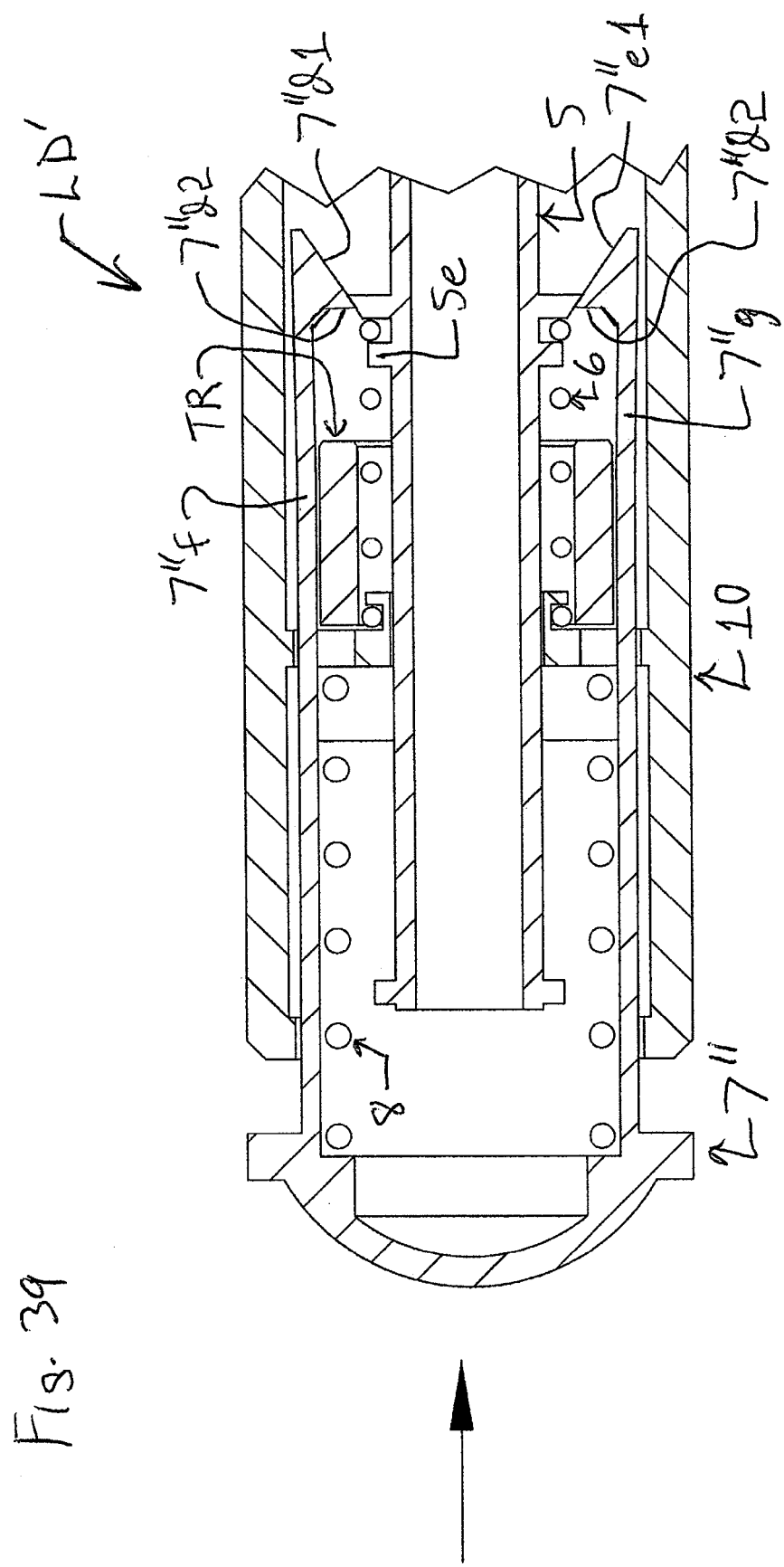
FIG. 39 shows a partial side cross-section view of a second embodiment of the lancet device. This embodiment utilizes a push-button trigger setting and/or cocking system and a trigger release member which automatically triggers or fires the lancet device after the user depresses the push-button. The front portion of the lancet device is not shown. The push-button is shown partially depressed position and prior to becoming locked with the holding member.
Figure 40:
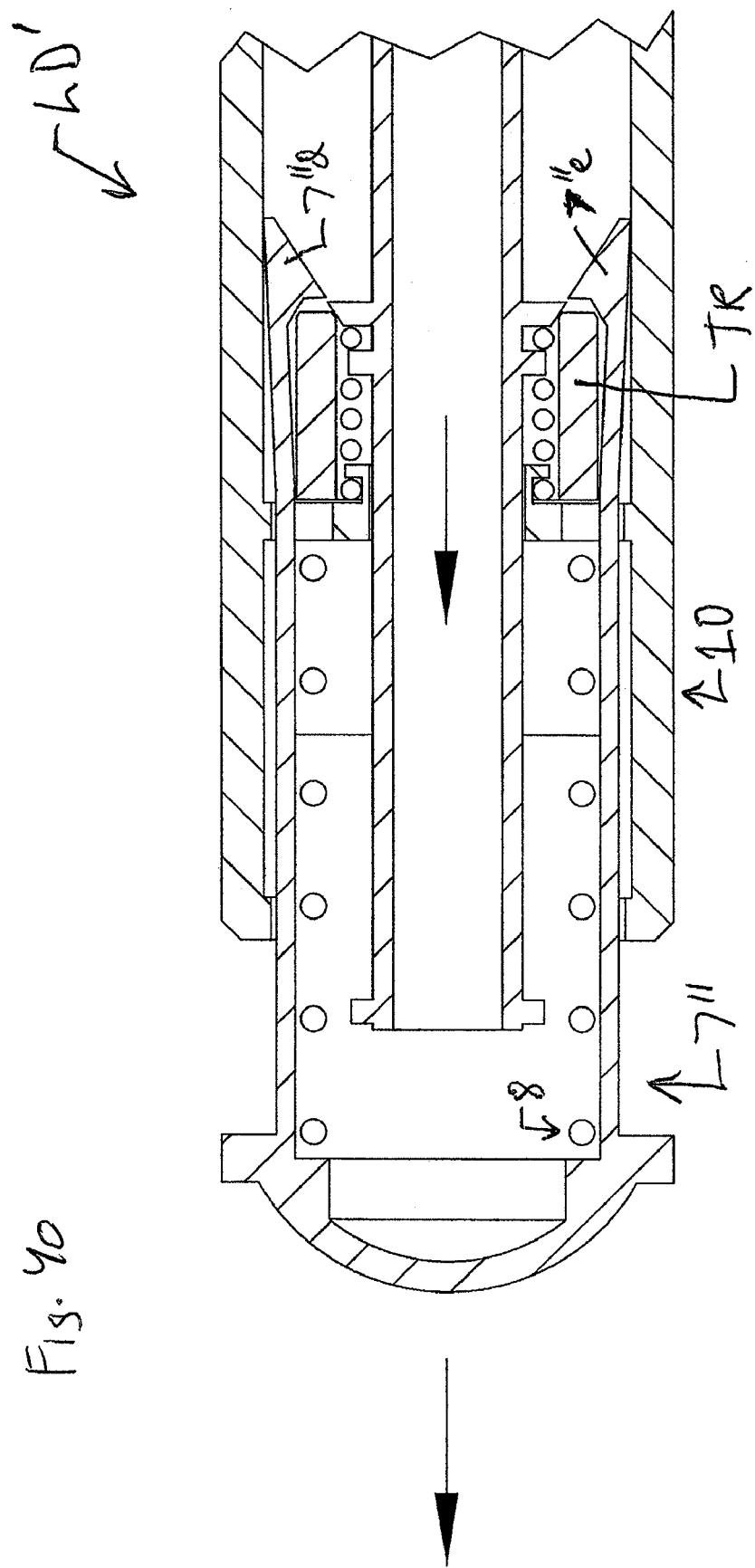
FIG. 40 shows another partial side cross-section view of FIG. 39. The push-button is shown in an axial cocked position and the trigger release member is shown causing the push-button to become unlocked with the holding member.
Figure 41:
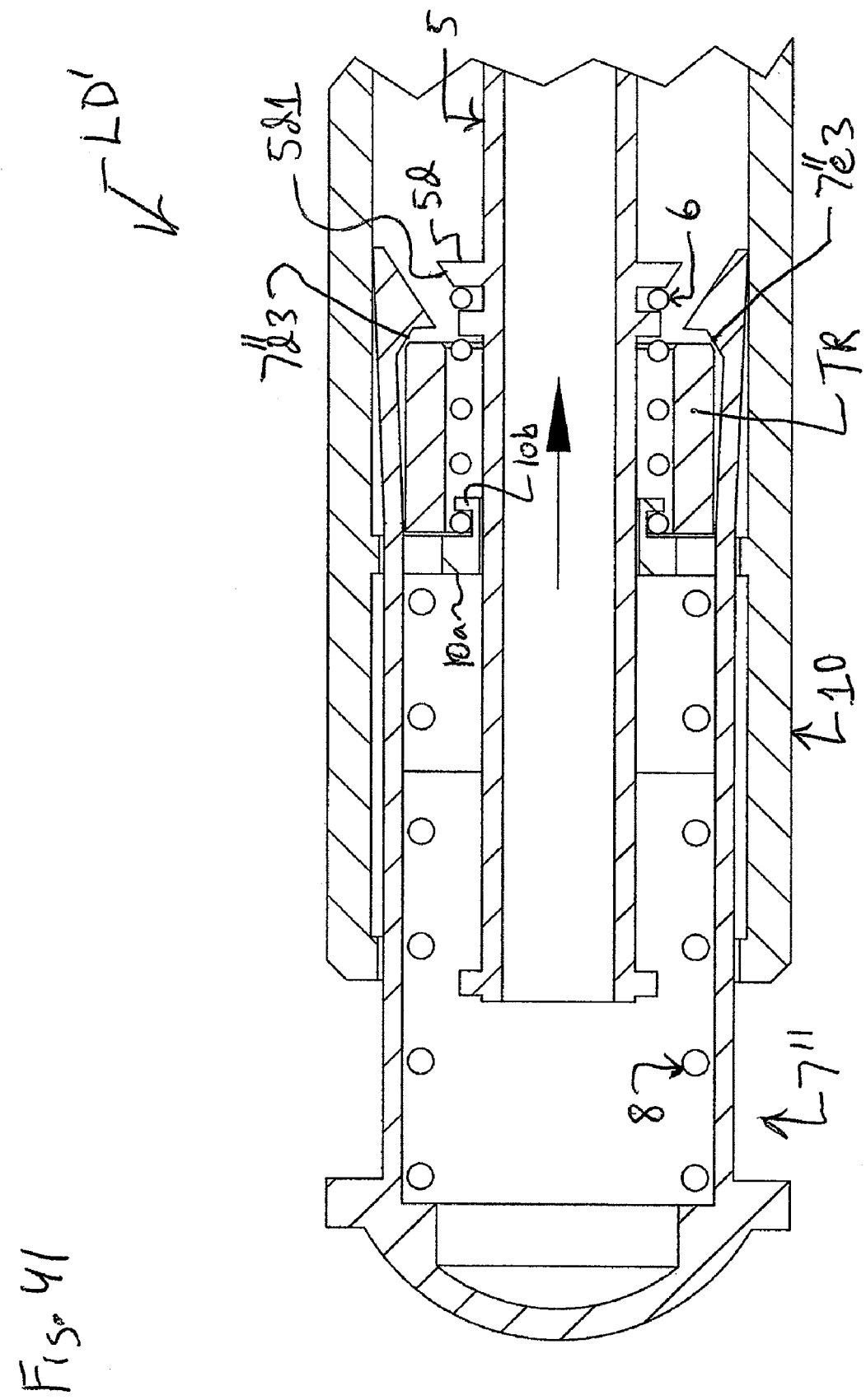
FIG. 41 shows another partial side cross-section view of FIG. 39. The holding member is shown by the arrow to be moving to the fully extended or puncturing position.

FIGS. 39-41 show another non-limiting embodiment of the lancet device. Lancet device LD' has a lancet body 10 which can be made as a one-piece member as is shown in FIGS. 13 and 14, as a two-piece body as shown in FIG. 15 or alternatively FIG. 16. Such body parts can, of course, be connected, e.g., using adhesives and/or fasteners and/or welding and/or snap-together holding mechanisms (not shown) to each other when the lancet device LD' is initially assembled. A holding member 5 is movably disposed within the body 10. Also, a front cover 3 (see e.g., FIG. 30) is removably connected or attached to an intermediate and/or an adjustable section 2. The adjustable section or intermediate member 2 is threadably mounted to a front portion of the body 10. By removing the front cover 3, a user can gain access to the lancet L. The lancet L can thus be removed and replaced with a new lancet L, as needed, once the front cover 3 is removed. As in known lancet devices, the lancet device LD defines a plane P which is configured to contact (i.e., be positioned against) a user's skin. Although not shown, the instant embodiment may also utilize an inwardly curved and/or an outwardly curved surface plane P beyond which the lancet need can extend. The lancet holder 5 has a rear portion and a front portion 4 that can be accessed by a user upon removal of the front cover 3 in order to all for replacement of the lancet L. The holding member 5 slides within the body 10 and more specifically slides within openings (similar to openings 1e and 1k in FIGS. 13 and 39) of the body 10. As will be described in more detail later on, movement of the holding member 5 rearwardly, causes the holding member 5 to retract until it reaches a spring loaded position shown in FIG. 40. The lancet L, itself is conventional and includes a needle. It can be removed and replaced with a new one, as is the case in many lancet devices. To ensure that lancet L is securely (yet removably) retained within the lancet device LD, the front portion 4 of the holding member 5 includes a lancet holding opening 5a which receives the lancet L therein.

Figure 3:
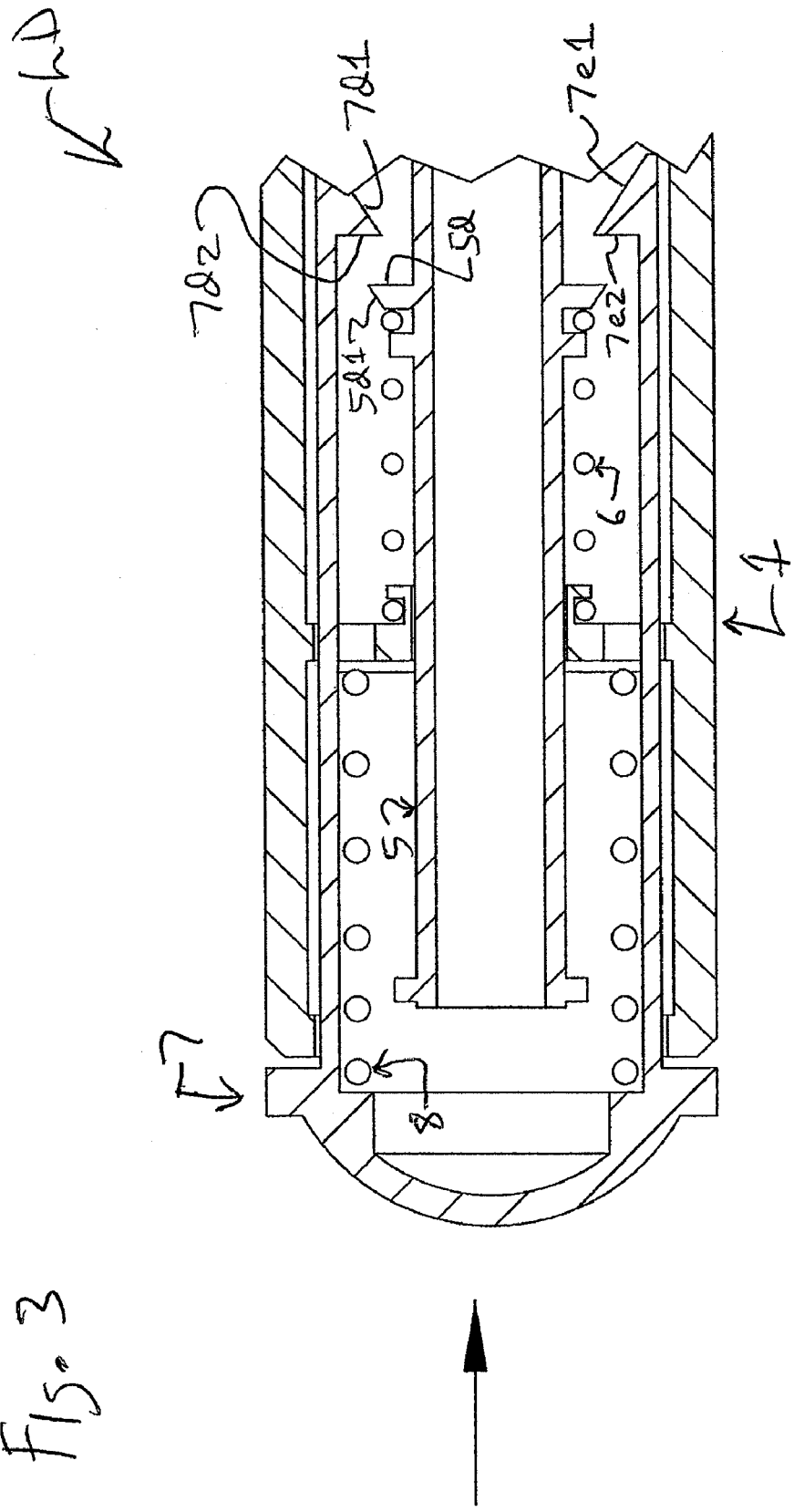
FIG. 3 shows another side cross-section view of the embodiment shown in FIG. 1. The push-button has been depressed further and is shown in a fully depressed position prior to causing retraction of the holding member.
Figure 4:
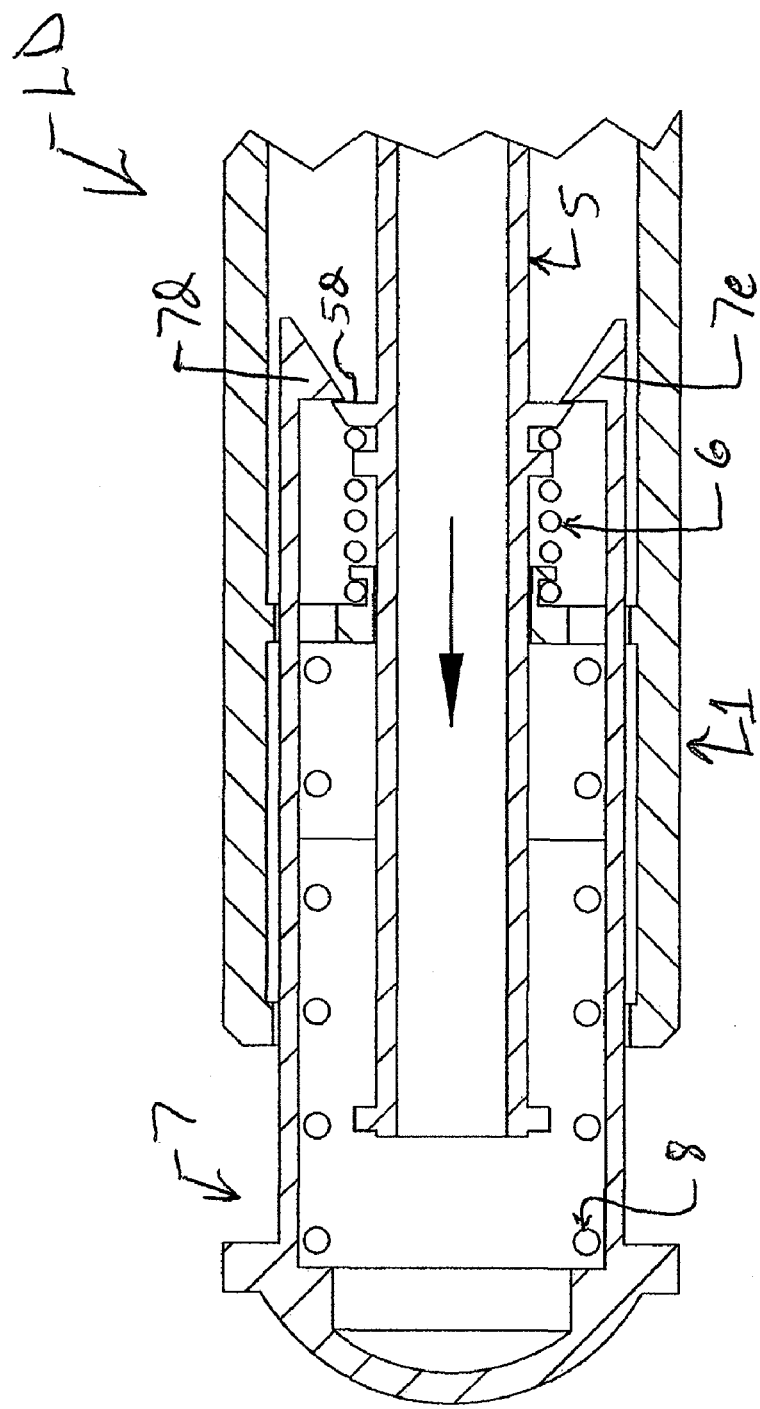
FIG. 4 shows another side cross-section view of the embodiment shown in FIG. 1. The push-button has been released, has become locked to the holding member, and has moved rearward to cause retraction of the holding member. In this position, the lancet device is said to be cocked and ready to fire.
Figure 5:
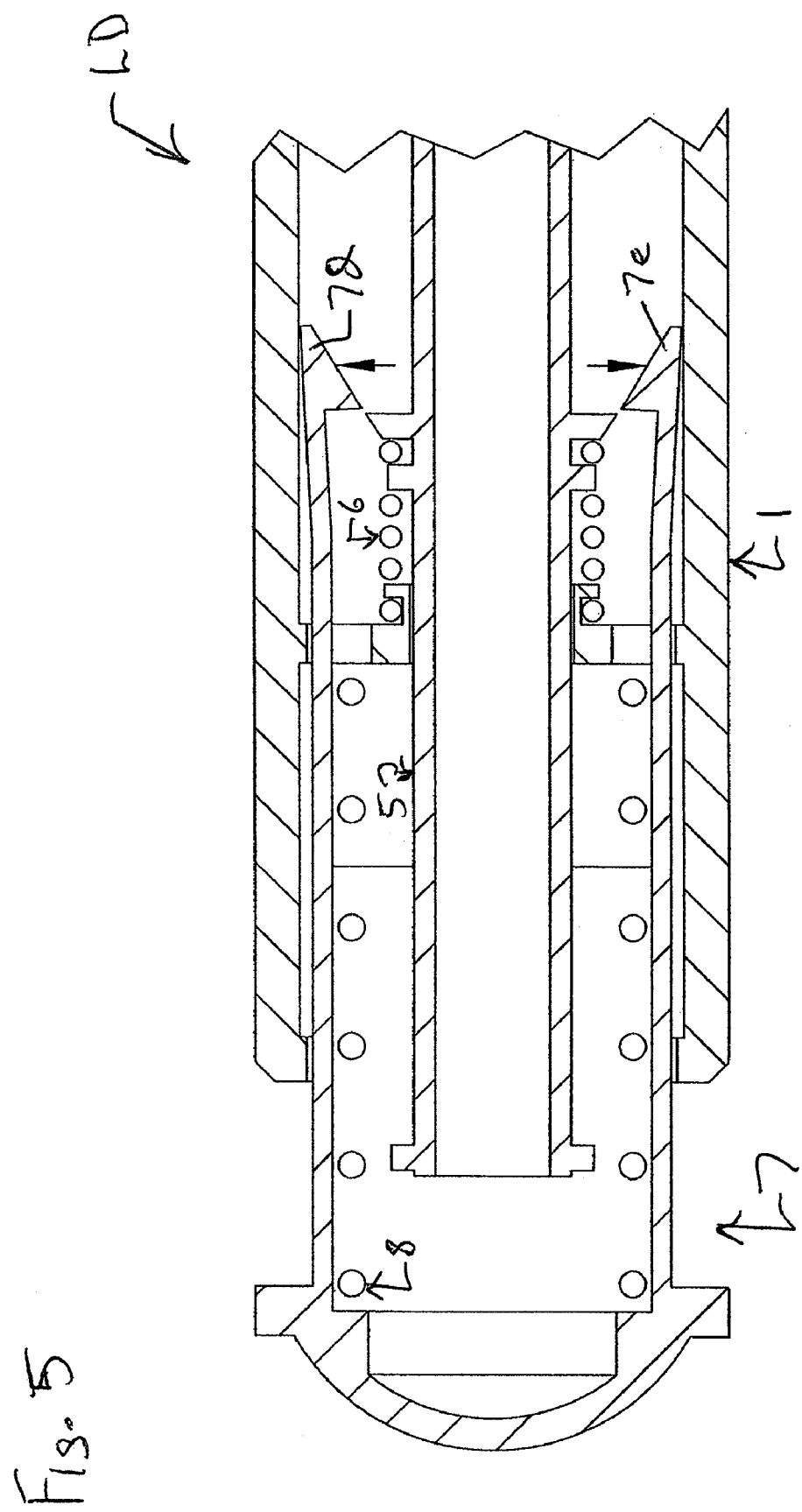
FIG. 5 shows another side cross-section view of the embodiment shown in FIG. 1. The arrows indicate where forces can be applied to release or unlock the push-button from the holding member and thereby cause the lancet device to fire.

As in the embodiment shown in FIGS. 1-6, the embodiment shown in FIGS. 39-41 utilizes a holding member 5 that preferably has a spring 6 mounted thereto. In this regard, the spring 6, which can be made of spring steel, is arranged to surround the holding member 5, just behind a tapered circumferential projection 5d. By way of one non-limiting example, the spring 6 may have a diameter of between approximately 5 mm and approximately 15 mm, a freelength of between approximately 10 mm and approximately 40 mm, and a wire size of between approximately 0.5 mm and 2 mm. This first spring 6 causes (and/or biases) the holding member 5 to move towards an extended position once an automatic triggering system is activated. FIG. 40 shows the activation of the automatic triggering system which utilizes a trigger ring TR to cause the movement of members 7"f and 7"g indicated by arrows in FIG. 5. In operation, when the push-button 7" is depressed (see FIG. 39), the deflecting members 7"f and 7"g of the push-button 7" are caused to deflect outwards by engagement between surfaces 7"d1 and 7"e1. This allows the deflecting members 7f and 7g to move past the projection 5d of the member 5 (in the same way as is shown in FIG. 3). When the user then releases the push-button 7", the spring 8 automatically expands and causes the push-button 7" to move rearwards. However, because the shoulder surfaces 7"d2 and 7"e2 contact the projection 5d, the holding member 5 is cause to move rearwards which, in turn, compresses the spring 6 (see FIG. 40). However, when the holding member 5 moves to the position shown in FIG. 40, the trigger ring TR contacts the tapered surface 5d1 and the tapered surfaces 7"d3 and 7"e3 which causes deflection of the members 7"f and 7"g and disengagement of the surfaces 7"d2 and 7"e2 from the projection 5d (see FIG. 40). This, in turn, allows the holding member 5 to move towards plane P under the action of the spring 6 (see FIG. 41). Thus, no trigger is required to be depressed to activate the lancet device LD'. All that is required to cause puncturing of the user's skin is for the user to place the plane P against the user's skin and then depress the push-button 7" and release the same. Once the push-button 7" is released, the lancet device LD' will be cocked and triggered automatically. Alternatively, all that is required to cause puncturing of the user's skin is for the user to initially set the lancet device LD' to a desired depth setting, then place the plane P against the user's skin, and then depress the push-button 7" and release the same. Once the push-button 7" is released, the lancet device LD' will be cocked and triggered automatically.

As discussed above, the spring 6 causes (and/or biases) the holding member 5 to move towards an extended position (see FIG. 41). The other spring 8 is utilized to bias a push-button 7" towards an extended or rearward position. As was the case in the previous embodiments, the spring 8 is also sized and configured to cause compression of the first spring 6 when the push-button 7" becomes locked to the holding member 5 and is released (see FIG. 40).

The operation of the lance device shown in FIGS. 39-41 will now be described. When a user wishes to use the lancet device LD', the user will typically pick up the lancet device LD' and grip in the user's hand. Then, the user will remove the front cover 3 and install a new lancet L. The user will then depress the push-button 71' with, e.g., the user's thumb. As is shown in FIG. 39, this movement of the push-button 7" causes tapered end portions 7"d and 7"e (and more specifically tapered surfaces 7"d1 and 7"e1) to contact and be deflected outwardly by the tapered surface 5d1 of the projection 5d. The tapered end portions 7"d and 7"e then move past the projection 6d and deflect inwardly to an original or relaxed position (similar to that shown in FIG. 3). Of course, the movement shown in FIG. 39 will tend to cause the holding member 5 to move a small amount towards the plane P. The spring 6, however, ensures that this movement is kept to a minimum. Once the push-button 7" is fully depressed (similar to that shown in FIG. 3), the user can release the push-button 7". This allows the spring 8 to automatically expand rearwards, and the expansion causes the push-button 7" to move rearwards whereby the portions 7"d and 7"e become locked to the projection 5d of the holding member 5 (similar to that shown in FIG. 4). This, in turn, causes the holding member 5 to move to the fully retracted position shown in FIG. 40 which causes the spring 6, which will provide the energy required to move the holding member 5 to the fully extended and/or puncturing position, to be fully compressed. However, upon reaching this position, as is shown in FIG. 4, the trigger ring TR engages with tapered surfaces 5d1 and 7"d3 and 7"e3 and causes the deflecting members 7"d and 7"e to move out of engagement with the shoulder/flange/projection 5d (see FIG. 40). Then, the spring 6 automatically causes the holding member 5 to move to a fully extended position (see FIG. 41). The spring 6 also causes the holding member 5 to automatically retract axially back within the body 10 to an original position (similar to that shown in FIG. 1). This occurs because the spring 6 has one end, i.e., the right end, coupled to, via two generally circumferential shoulders 5e and 6d, the holding member 5 and another end, i.e., the left end, coupled to and/or fixed between two internal generally circumferential shoulders 10a and 10b of the body 10. The spring 6 can, of course, be connected to these parts in any desired manner. In this way, the lancet needle only momentarily projects past the plane P in the extended position before it is caused to automatically retract back in the lancet device by the spring 6. As a result, the lancet needle only projects past or beyond the plane P for a very brief time (i.e., a fraction of a second when the lancet device LD is triggered) and is otherwise not exposed to a user while the front cover 3 is installed thereon. Accordingly, a user or other innocent bystanders can be protected from being injured unintentionally by an exposed needle.

Figure 42:
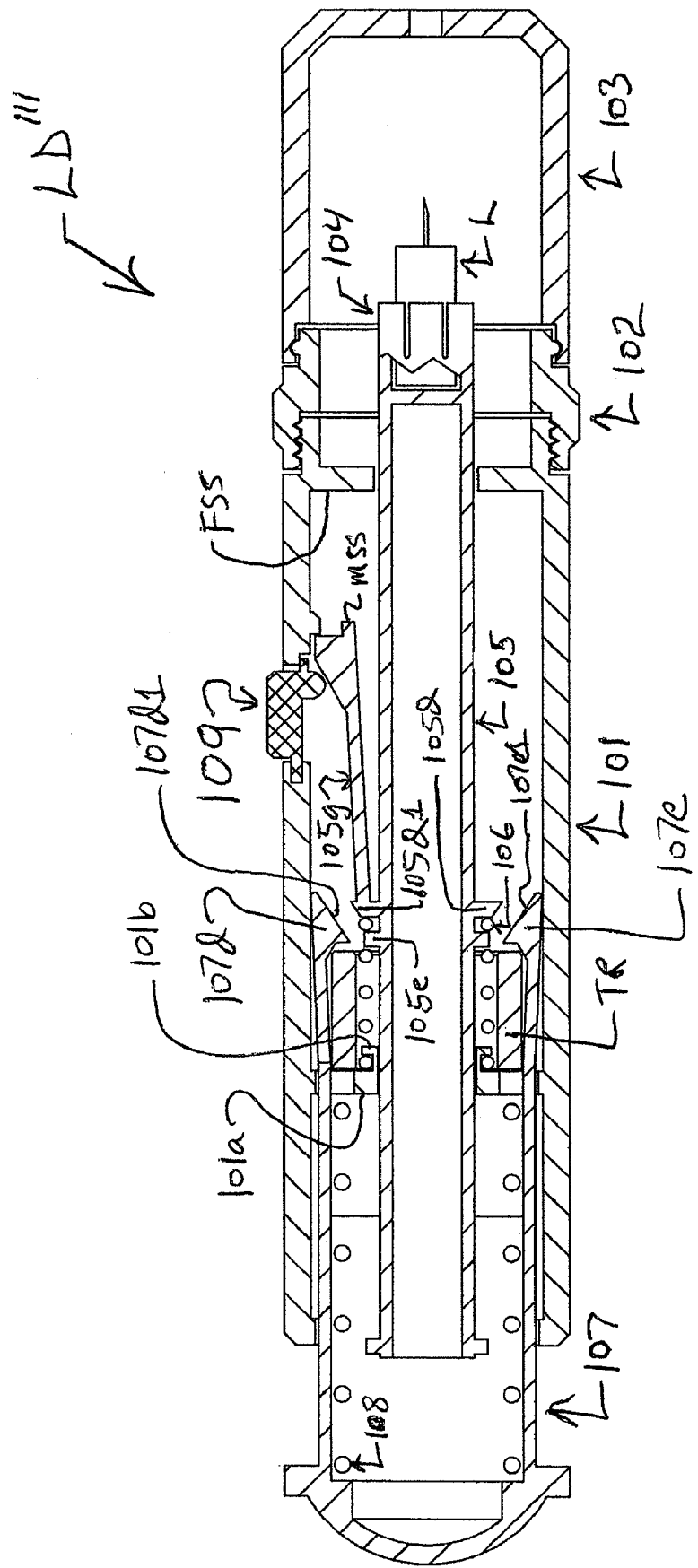
FIG. 42 shows a side cross-section view of still another embodiment of the lancet device. The lancet device utilizes the features shown in FIGS. 39-41 and further utilizes a triggering system. This embodiment utilizes a push-button trigger setting and/or cocking system and a trigger system which can be activated by the user to trigger or fire the lancet device after the user depresses the push-button.

FIG. 42 shows a side cross-section view of still another embodiment of the lancet device. The lancet device LD" utilizes the features shown in FIGS. 39-41 and further utilizes a manually activated triggering system. In particular, this embodiment utilizes a push-button trigger setting and/or cocking system shown in FIGS. 38-41 and a trigger system of the type disclosed in U.S. Pat. No. 2005/0234495 to SCHRAGA which includes a trigger 109 which can be activated by the user and a deflectable member 105g to trigger or fire the lancet device LD" after the user depresses the push-button 107.

The operation of the lance device shown in FIG. 42 will now be described. When a user wishes to use the lancet device $LD^{III}$, the user will typically pick up the lancet device $LD^{III}$ and grip in the user's hand. Then, the user will remove the front cover 3 and install a new lancet L. The user will then depress the push-button 107 with, e.g., the user's thumb. In the same as was shown in FIG. 39, this movement of the push-button 107 causes tapered end portions 107d and 107e (and more specifically tapered surfaces 107d1 and 107e1) to contact and be deflected outwardly by the tapered surface 105d1 of the projection 105d. The tapered end portions 107d and 107e then move past the projection 105d and deflect inwardly to an original or relaxed position (similar to that shown in FIG. 3). Of course, the movement shown in FIG. 39 will tend to cause the holding member 105 to move a small amount towards the plane P. The spring 106, however, ensures that this movement is kept to a minimum. Once the push-button 107 is fully depressed (similar to that shown in FIG. 3), the user can release the push-button 107. This allows the spring 108 to automatically expand rearwards, and the expansion causes the push-button 107 to move rearwards whereby the portions 107d and 107e become locked to the projection 105d of the holding member 105 (similar to that shown in FIG. 4). This, in turn, causes the holding member 105 to move to the fully retracted position (see FIG. 40) which causes the spring 106, which will provide the energy required to move the holding member 105 to the fully extended and/or puncturing position, to be fully compressed. However, upon reaching this position (see FIG. 40), the trigger ring TR engages with tapered surfaces 105d1 and 107d3 and 107e3 and causes the deflecting members 107d and 107e to move out of engagement with the shoulder/flange/projection 105d (see FIG. 40). Then, the spring 106 automatically causes the holding member 105 to move towards the plane P until the deflecting member 105g engages with a shoulder of the body 101 (see FIG. 42). The lancet device $LD^{III}$ is now in a trigger set or cocked position and ready to be triggered for puncturing. When the user desires to cause puncturing of the skin, the user need only depress the trigger 109 to cause the deflecting member 105g to disengage from a shoulder of the body 101 in the same as is disclosed in U.S. Pat. No. 2005/0234495 to SCHRAGA. This, in turn, causes the holding member 105 to move to a fully extended position defined by contact between the movable stop surface MSS and the fixed stop surface FSS. The spring 106 also causes the holding member 105 to automatically retract axially back within the body 101 to an original position (similar to that shown in FIG. 1). This occurs because the spring 106 has one end, i.e., the right end, coupled to, via two generally circumferential shoulders 10e and 10d, the holding member 105 and another end, i.e., the left end, coupled to and/or fixed between two internal generally circumferential shoulders 101a and 101b of the body 101. The spring 106 can, of course, be connected to these parts in any desired manner. In this way, the lancet needle only momentarily projects past the plane P in the extended position before it is caused to automatically retract back in the lancet device by the spring 106. As a result, the lancet needle only projects past or beyond the plane P for a very brief time (i.e., a fraction of a second when the lancet device $LD^{III}$, is triggered) and is otherwise not exposed to a user while the front cover 3 is installed thereon. Accordingly, a user or other innocent bystanders can be protected from being injured unintentionally by an exposed needle.

FIGS. 43-48 show another non-limiting embodiment of the lancet device. The lancet device $LD^{IV}$ utilizes, like the embodiment shown in FIG. 42, a manually activated triggering system. In particular, this embodiment utilizes a push-button trigger setting and/or cocking system and a trigger system which includes a trigger 1109 which can be activated by the user to trigger or fire the lancet device $LD^{IV}$ after the user depresses the push-button 1107.

Figure 43:
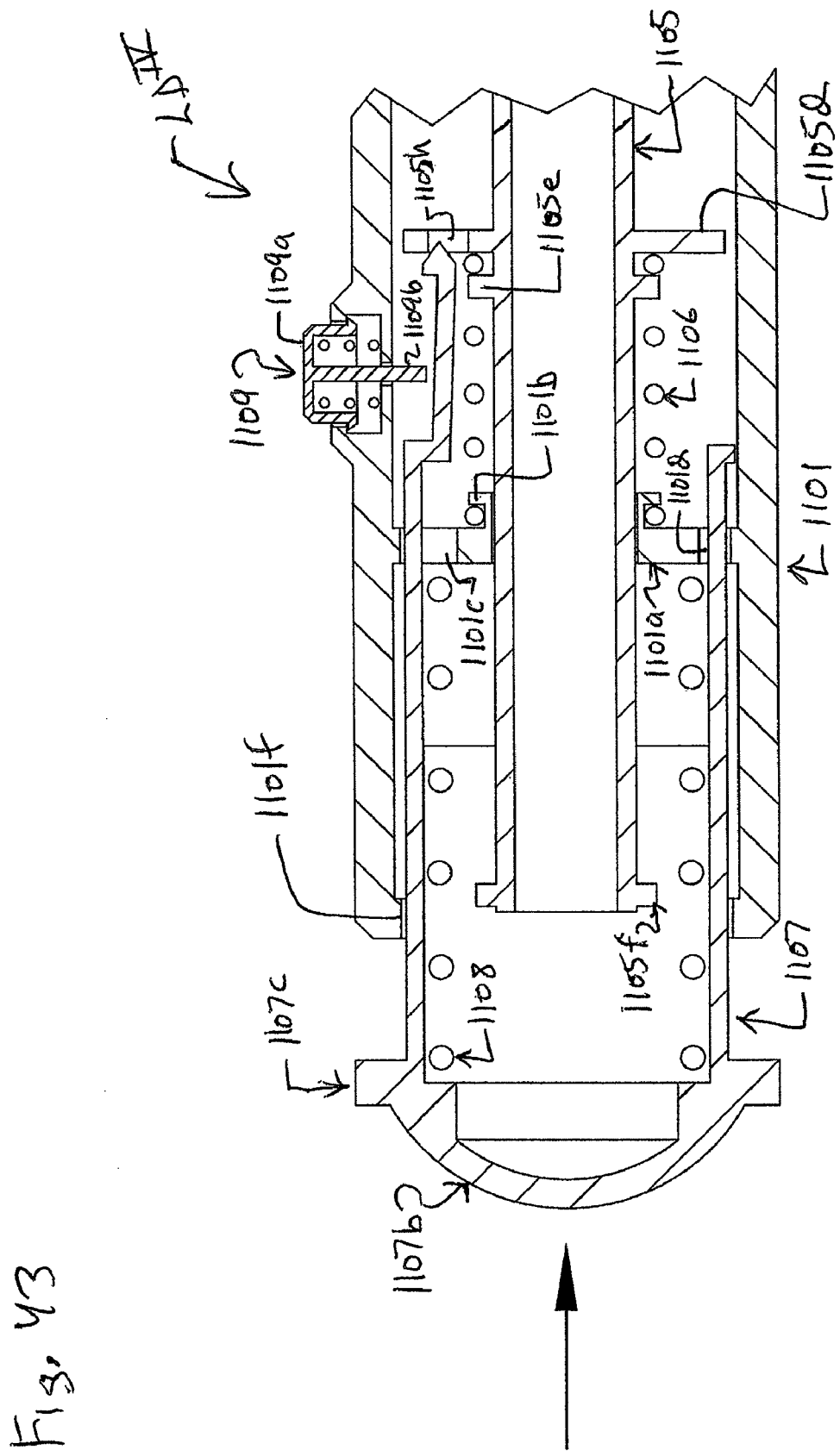
FIG. 43 shows a partial side cross-section view of still another embodiment of the lancet device. This embodiment utilizes a push-button trigger setting and/or cocking system and a trigger system which can be activated by the user to trigger or fire the lancet device after the user depresses the push-button. The front portion of the lancet device is not shown. The push-button is shown partially depressed position and prior to becoming locked with the holding member.
Figure 44:
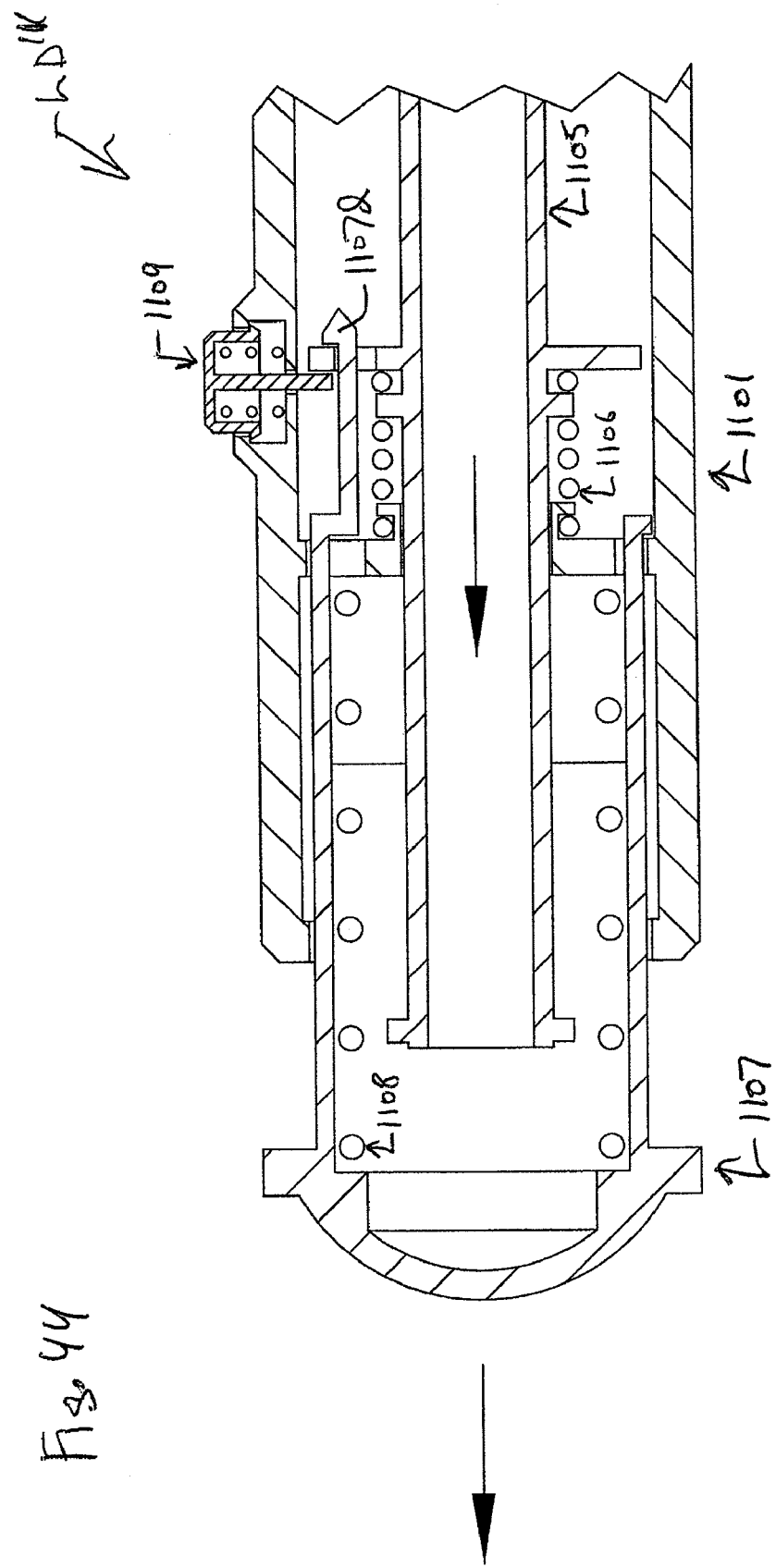
FIG. 44 shows another partial side cross-section view of FIG. 43. The push-button is shown in an axial cocked position and the trigger is shown in an initial non-triggering position.
Figure 45:
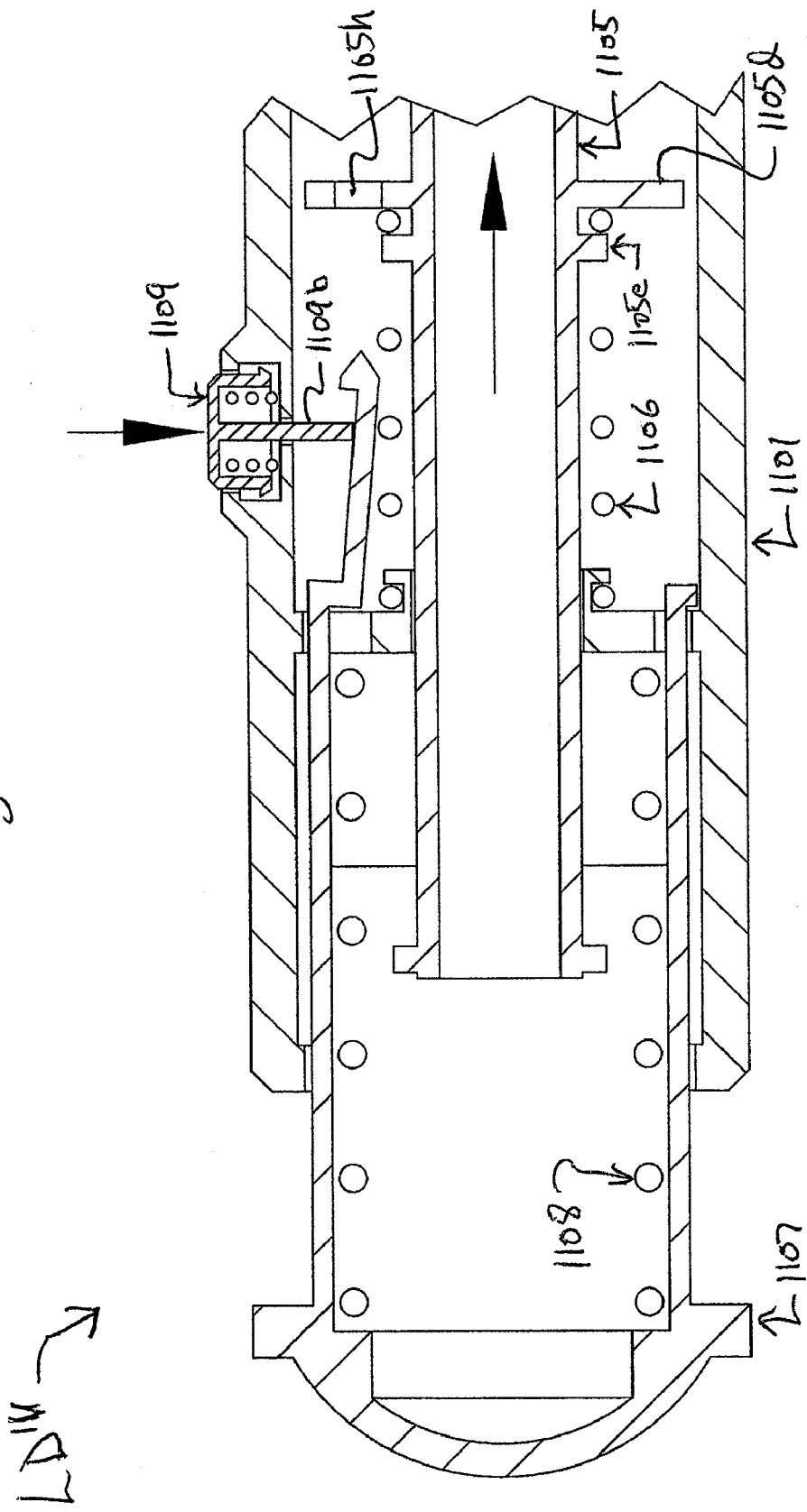
FIG. 45 shows another partial side cross-section view of FIG. 43. The trigger is shown in a depressed or triggering position and the holding member is shown moving towards an extended or puncturing position.
Figure 46:
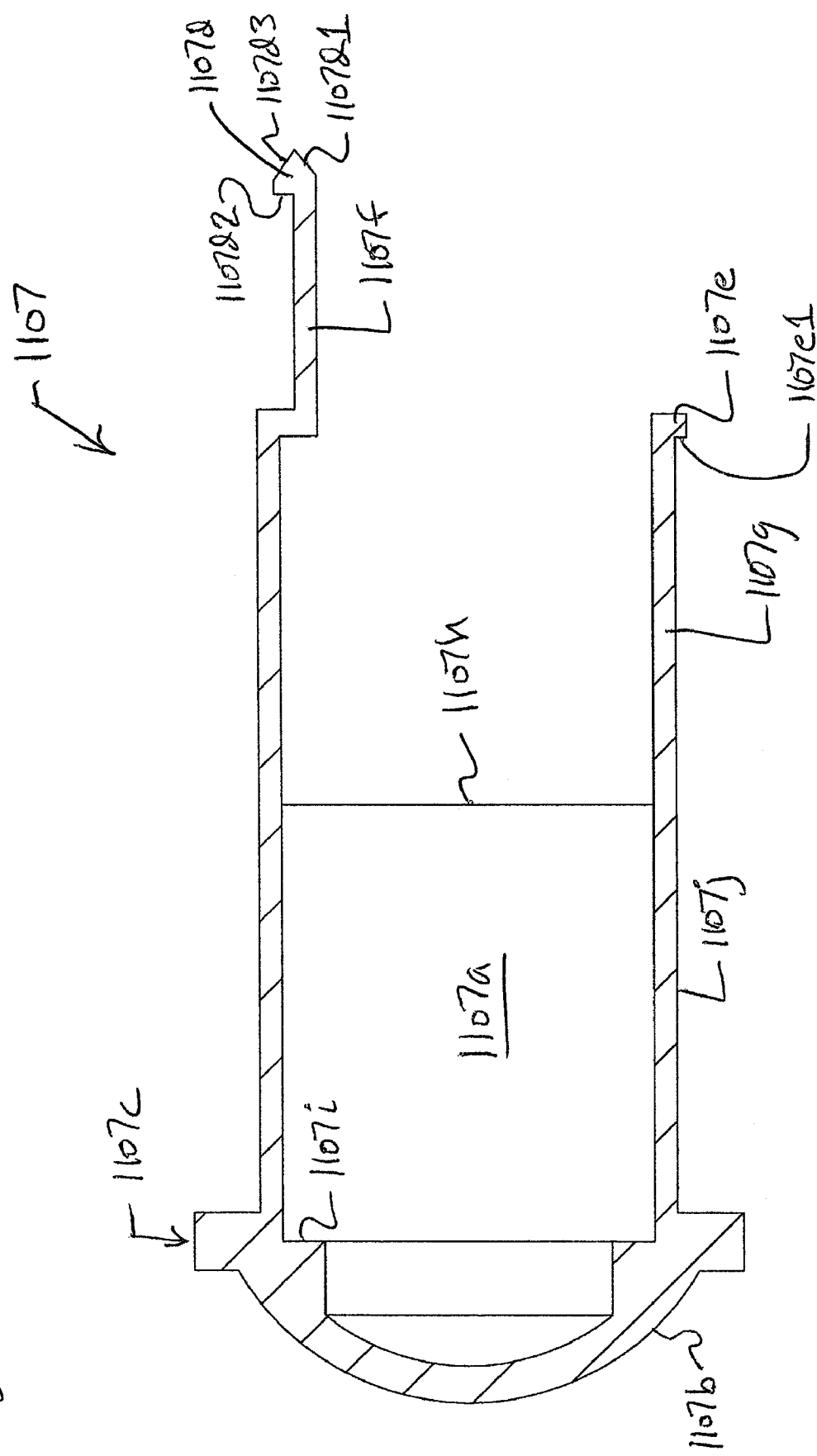
FIG. 46 shows a side cross-section view of the push-button utilized in the embodiment shown in FIGS. 43-45.
Figure 47:
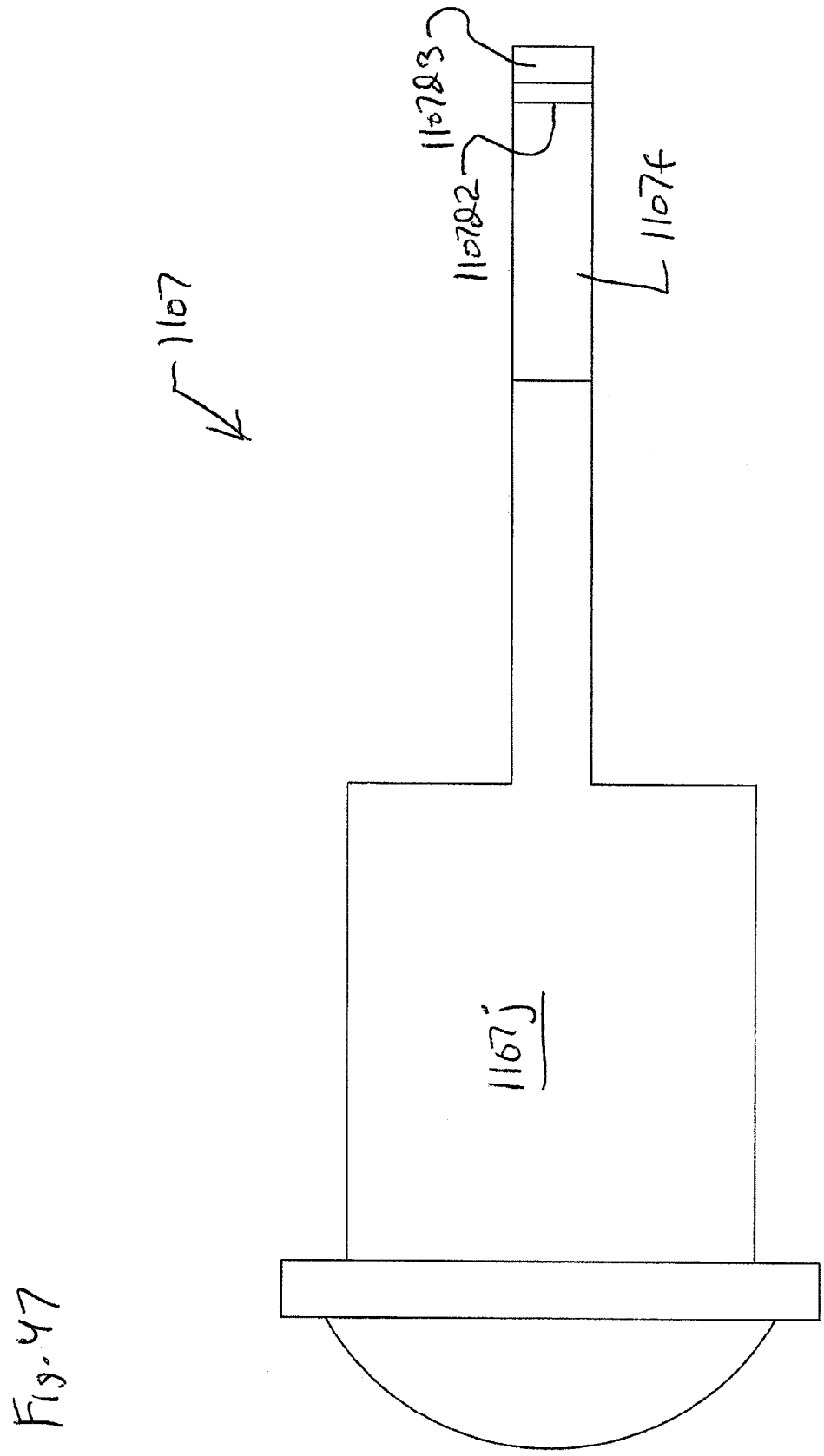
FIG. 47 shows a top view of the push-button shown in FIG. 46.
Figure 48:
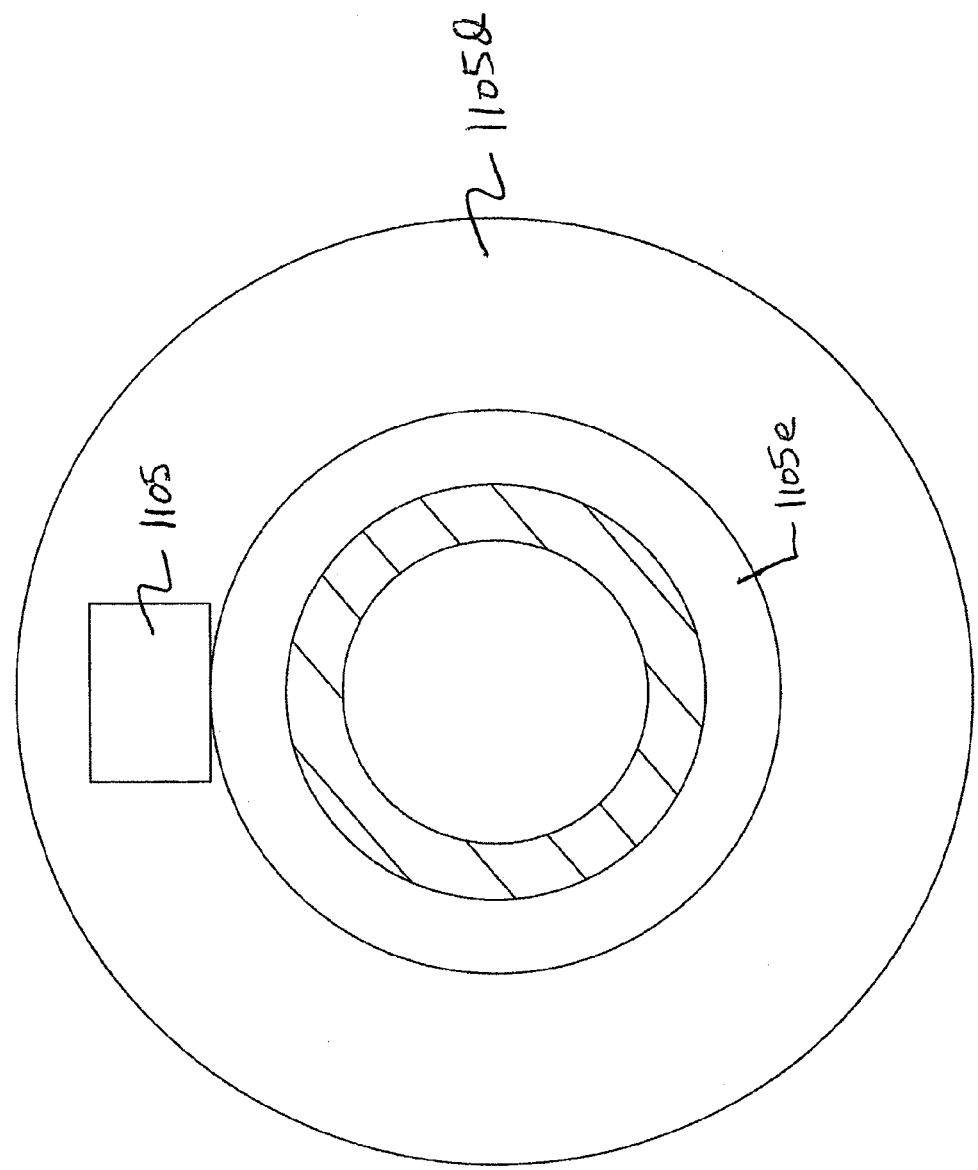
FIG. 48 shows an end cross-section view of the holding member utilized in the embodiment shown in FIGS. 43-45.
Figure 49:
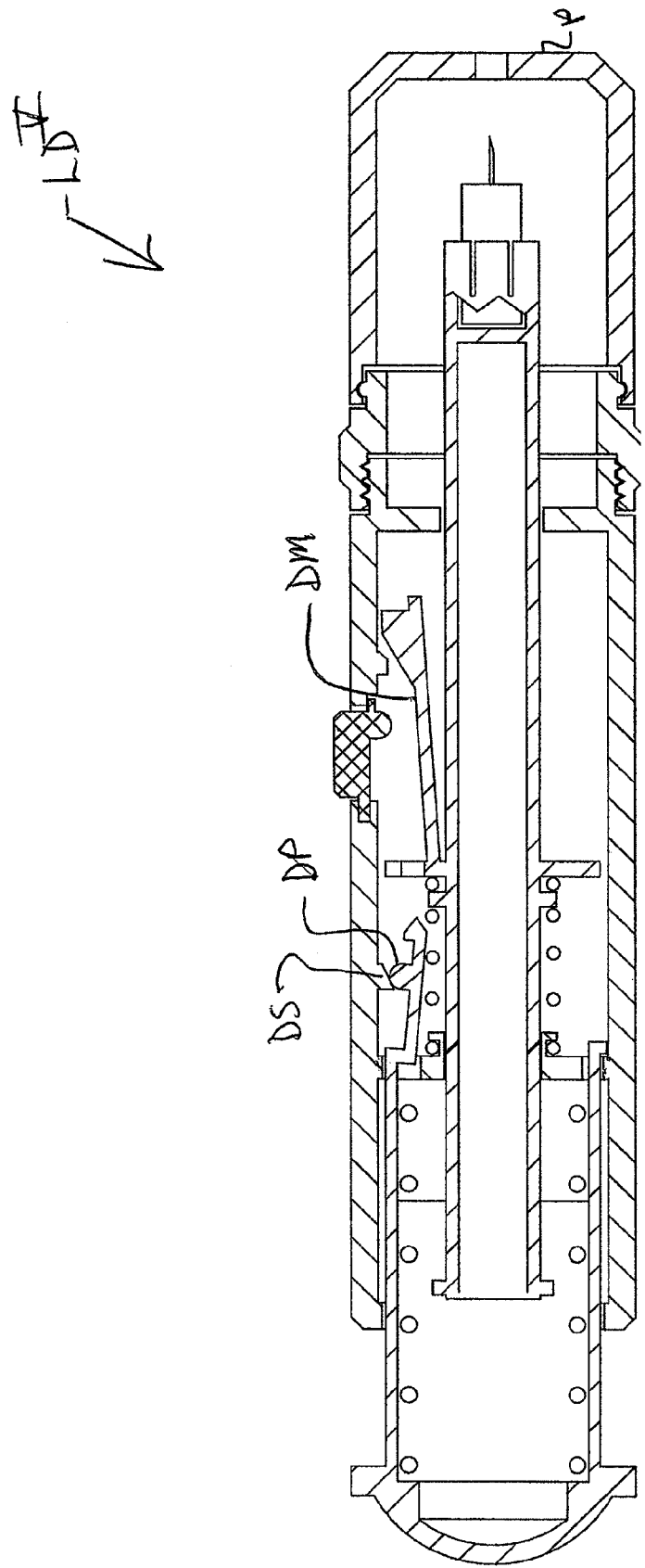
FIG. 49 shows a side cross-section view of still another embodiment of the lancet device. This embodiment utilizes a push-button trigger setting and/or cocking system and a trigger system which can be activated by the user to trigger or fire the lancet device after the user depresses the push-button. The lancet device is shown in an initial un-cocked and/or ready to use position.

FIGS. 46 and 47 show a non-limiting embodiment of the push-button 1107 which is utilized on the lancet device $LD^{IV}$ shown in FIGS. 43-45. The push-button 1107 has a cylindrical outer surface 1107j which is sized to slide within and/or slidably engage with opening 1101f of the body 1101, and has a main open area 1107a which is sized to house and receive therein the spring 1108. An internal shoulder 1107i is arranged within the opening 1107a and is configured to contact one end of the spring 1108. An external shoulder 1107c is configured to contact a rear end of the body 1101. The push-button 1107 also utilizes button portion 1107b which is configured to be engaged by a user. The push-button 1107 also utilizes one deflecting/locking portion 1107f which extends beyond an axial edge 1107h. Deflecting/locking portion 1107f has an engaging/locking portion 1107d arranged at a free end thereof. The engaging/locking portion 1107d includes tapered surfaces 1107d1 and 1107d3 which are configured to slidably engage with (and facilitate insertion into) the opening 1105h of the flange 1105d. Deflecting/locking portion 1107g has an engaging/locking portion 1107e arranged at a free end thereof. The engaging/locking portion 1107e includes a locking shoulder 1107e1 which is configured to engage with wall 1101a and thereby limit rearward movement of the push-button 1107 after the portion 11079 passes through opening 1101d.

The operation of the lance device shown in FIGS. 43-45 will now be described. When a user wishes to use the lancet device $LD^{IV}$, the user will typically pick up the lancet device $LD^{IV}$ and grip in the user's hand. Then, the user will remove the front cover 3 and install a new lancet L. The user will then depress the push-button 1107 with, e.g., the user's thumb. As is shown in FIG. 43, this movement of the push-button 1107 causes tapered end portions 1107d1 and 1107d3 to be guided into opening 1105h of the projection 1105d. The tapered end portion 1107d then moves past the projection 1105d and deflects outwardly to an original or relaxed position. Of course, the movement shown in FIG. 39 will tend to cause the holding member 1105 to move a small amount towards the plane P. The spring 1106, however, ensures that this movement is kept to a minimum. Once the push-button 1107 is fully depressed, the user can release the push-button 1107. This allows the spring 1108 to automatically expand rearwards, and the expansion causes the push-button 1107 to move rearwards whereby the portion 1107d becomes locked to the projection 1105d of the holding member 1105. This, in turn, causes the holding member 1105 to move to the fully retracted position (see FIG. 44) which causes the spring 1106, which will provide the energy required to move the holding member 1105 to the fully extended and/or puncturing position, to be substantially fully compressed. In the position shown in FIG. 44, the lancet device $LD^{IV}$ can be said to be cocked or in the trigger set position and is ready to be fired. Once the user desires to fire the lancet device $LD^{IV}$ (see FIG. 45), the user need only depress the trigger 1109 to cause the member 1107d to move out of engagement with the shoulder/flange/projection 1105d. Then, the spring 1106 automatically causes the holding member 1105 to move towards the plane P as in previous embodiments. The spring 1106 also causes the holding member 1105 to automatically retract axially back within the body 1101 to an original position (similar to that shown in FIG. 1). This occurs because the spring 1106 has one end, i.e., the right end, coupled to, via two generally circumferential shoulders 1105e and 1105d, the holding member 1105 and another end, i.e., the left end, coupled to and/or fixed between two internal generally circumferential shoulders 1101a and 1101b of the body 1101. The spring 1106 can, of course, be connected to these parts in any desired manner. In this way, the lancet needle only momentarily projects past the plane P in the extended position before it is caused to automatically retract back in the lancet device by the spring 1106. As a result, the lancet needle only projects past or beyond the plane P for a very brief time (i.e., a fraction of a second when the lancet device $LD^{IV}$ is triggered) and is otherwise not exposed to a user while the front cover 3 is installed thereon.

Accordingly, a user or other innocent bystanders can be protected from being injured unintentionally by an exposed needle.

FIGS. 49-52 show another non-limiting embodiment of the lancet device. The lancet device LD$^V$ utilizes a push-button and a holding member that is similar to that used in the embodiment shown in FIGS. 43-48 except that the holding member also utilizes a deflecting member and a trigger of the type used in the embodiment shown in FIG. 42. Additionally, the portion 1107ƒ of FIGS. 43-48 utilizes a deflecting projection DP which engages with an internal deflecting support DS of the body. In the position shown in FIG. 49, the deflecting projection DP is engaged with the internal deflecting support DS of the body and is thereby deflected inwardly.

Figure 50:
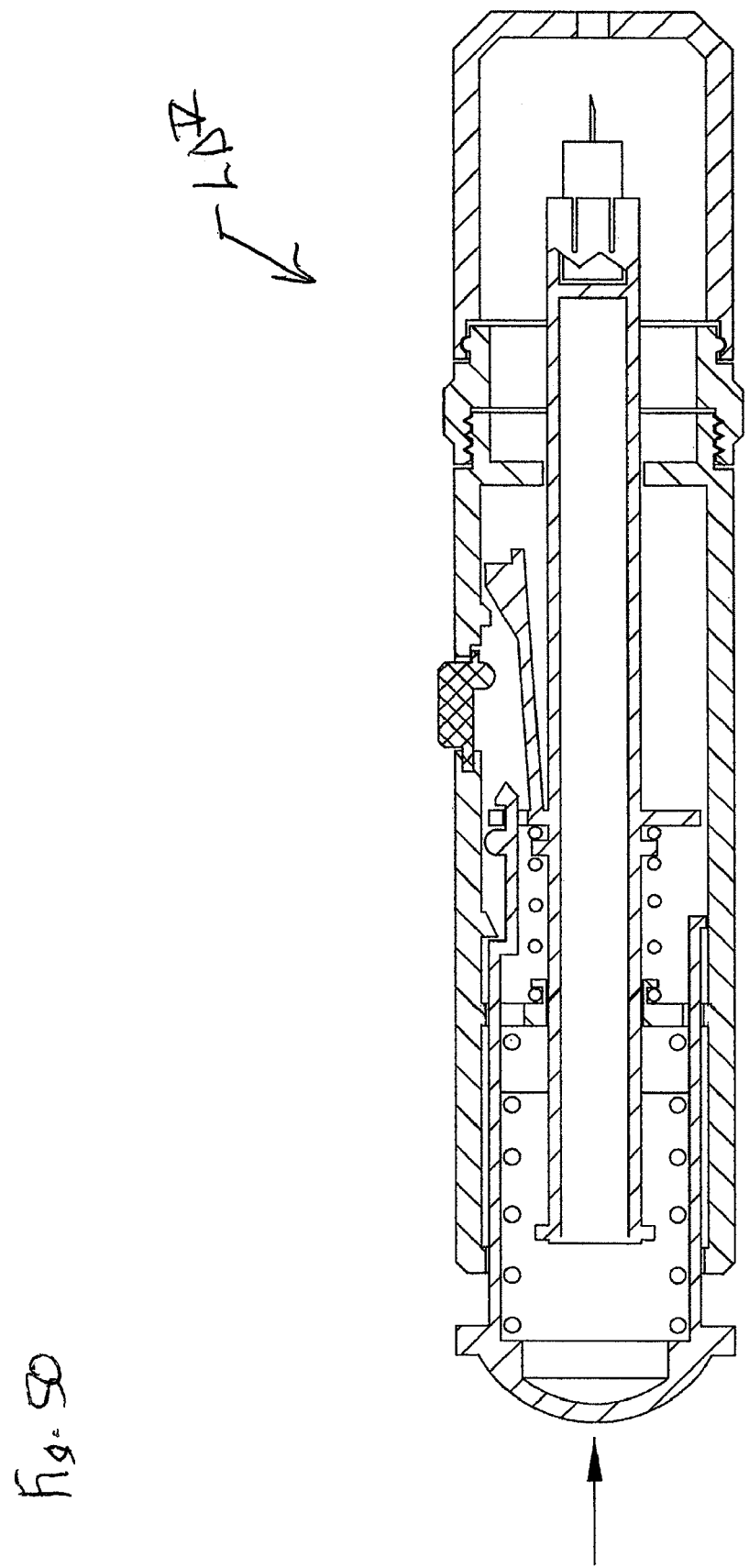
FIG. 50 shows another side cross-section view of FIG. 49. The push-button is shown being depressed and has become locked to the holding member. The lancet device is shown in a pre-cocked and/or pre-trigger set position.
Figure 51:
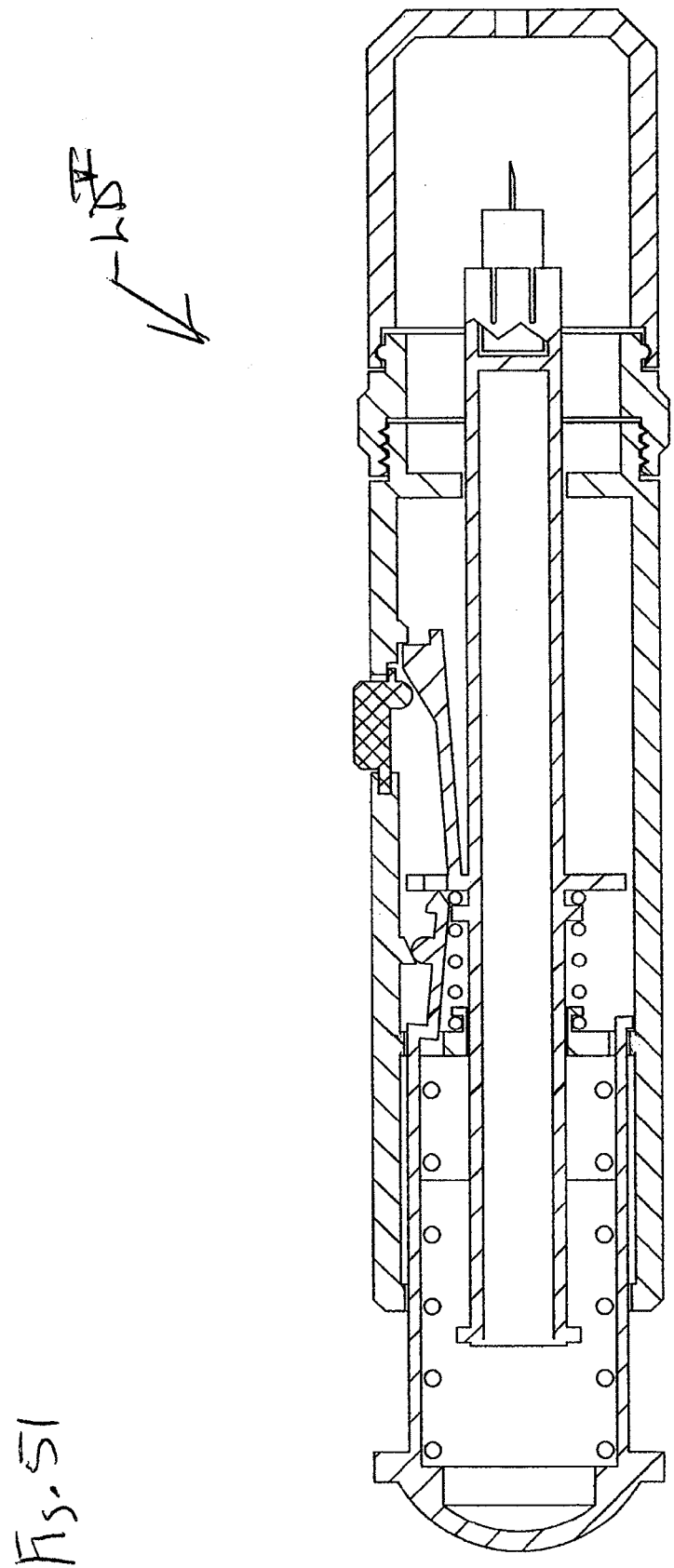
FIG. 51 shows another side cross-section view of FIG. 49. The push-button is shown is a released or extended position which has resulted in the push-button becoming automatically released and/or unlocked from the holding member. The lancet device is shown in a cocked and/or trigger set position.
Figure 52:
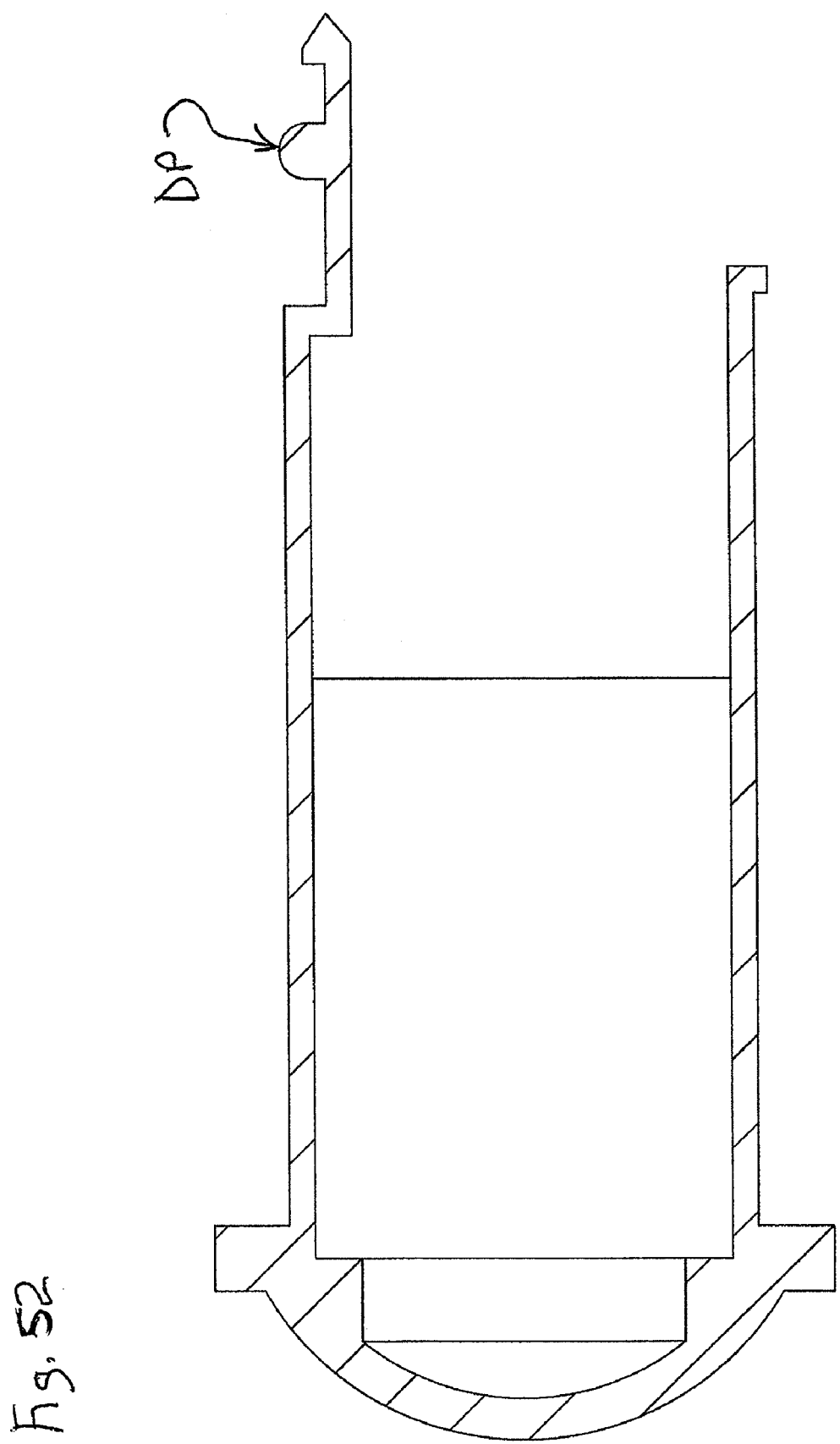
FIG. 52 shows a side cross-section view of the push-button utilized in the embodiment shown in FIGS. 49-51.

The operation of the lance device shown in FIGS. 49-52 will now be described. When a user wishes to use the lancet device LD$^V$, the user will typically pick up the lancet device LD$^V$ in the sate shown in FIG. 49 and grip in the user's hand. Then, the user will remove the front cover and install a new lancet. The user will then depress the push-button with, e.g., the user's thumb. As is shown in FIG. 50, this movement of the push-button causes tapered end portions of the push-button to be guided into an opening of the projection of the holding member just as in the embodiment shown in FIGS. 43-45. The tapered end portion then moves past the projection and deflects outwardly to an original or relaxed position as shown in FIG. 50. Of course, the movement shown in FIG. 50 will tend to cause the holding member to move a small amount towards the plane P. The holding member spring, however, ensures that this movement is kept to a minimum. Once the push-button is fully depressed, the user can release the push-button as in the embodiment shown in FIGS. 43-45. This allows the push-button spring to automatically expand rearwards, and the expansion causes the push-button to move rearwards whereby the locking portion of the push-button becomes locked to the projection of the holding member (see FIG. 51). This, in turn, causes the holding member to move to the fully retracted position which causes the holding member spring, which will provide the energy required to move the holding member to the fully extended and/or puncturing position, to be substantially fully compressed. However, upon reaching this position, the projection DP engages with the support DS and causes the locking member of the push-button to move out of engagement with the shoulder/flange/projection by deflecting inwardly. Then, the holding member spring automatically causes the holding member to move towards the plane P until the deflecting member DM engages with a shoulder of the body (see FIG. 51). The lancet device LD$^V$ is now in a trigger set or cocked position and ready to be triggered for puncturing. Once the user desires to fire the lancet device LD$^V$, the user need only depress the trigger to cause the member DM to move out of engagement with the shoulder of the body. Then, the holding member spring automatically causes the holding member to move towards the plane P as in previous embodiments. The holding member spring also causes the holding member to automatically retract axially back within the body to an original position (see FIG. 49). This occurs because the holding member spring has one end, i.e., the right end, coupled to, via two generally circumferential shoulders of the holding member and another end, i.e., the left end, coupled to and/or fixed between two internal generally circumferential shoulders of the body. The holding member spring can, of course, be connected to these parts in any desired manner. In this way, the lancet needle only momentarily projects past the plane P in the extended position before it is caused to automatically retract back in the lancet device by the holding member spring. As a result, the lancet needle only projects past or beyond the plane P for a very brief time (i.e., a fraction of a second when the lancet device LD$^V$ is triggered) and is otherwise not exposed to a user while the front cover is installed thereon. Accordingly, a user or other innocent bystanders can be protected from being injured unintentionally by an exposed needle.

Figure 53:
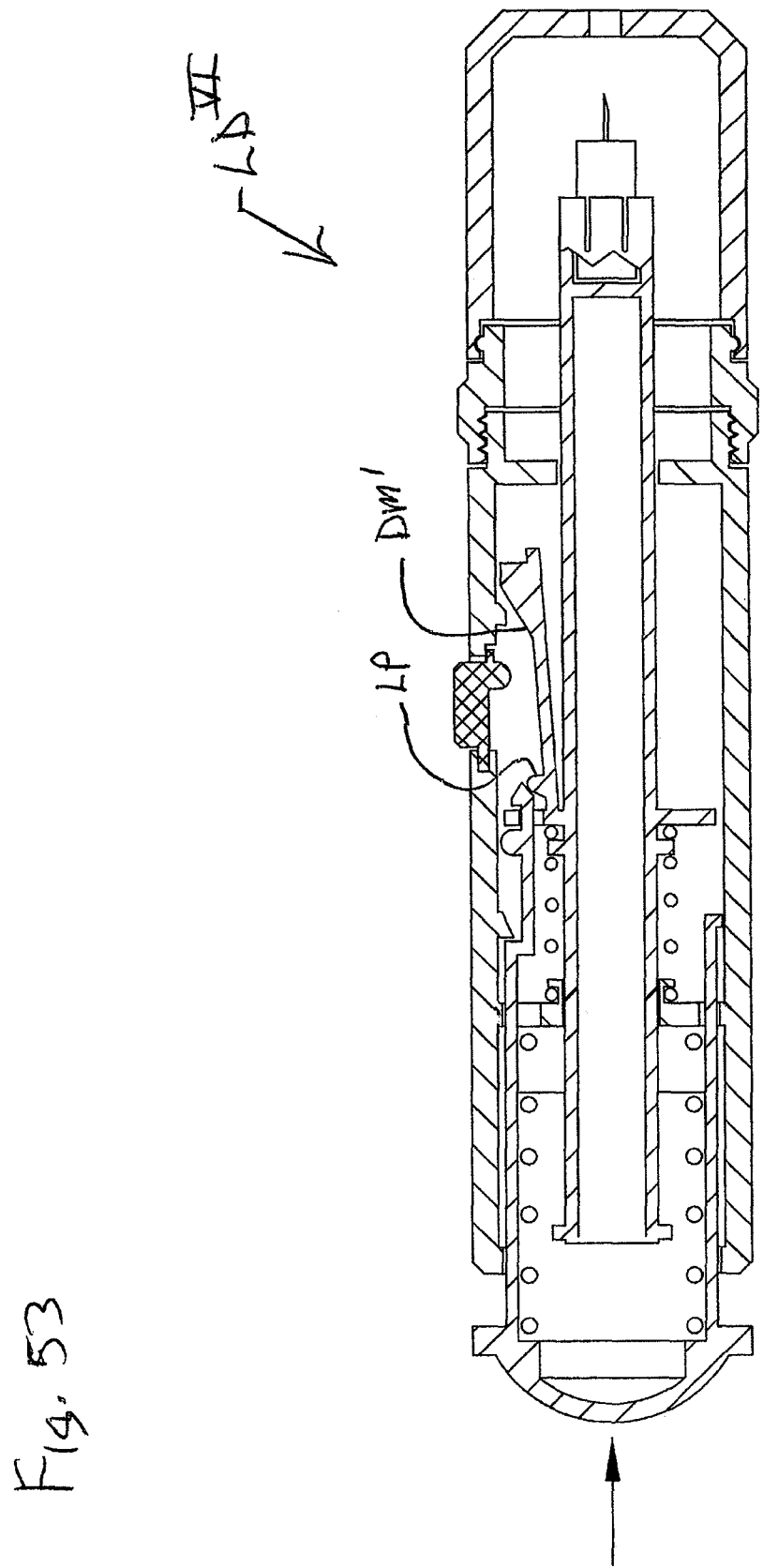
FIG. 53 shows a side cross-section view of still another embodiment of the lancet device. This embodiment utilizes a push-button trigger setting and/or cocking system and a trigger system which can be activated by the user to trigger or fire the lancet device after the user depresses the push-button. The lancet device is shown in an initial un-cocked and/or ready to use position.

FIG. 53 shows another non-limiting embodiment of the lancet device. The lancet device LD$^{VI}$ is substantially similar to the embodiment shown in FIGS. 49-52 except that the deflecting member DM utilizes a locking projection LP to assist in moving the locking portion of the push-button into locking engagement with the flange of the holding member.

Of course, the invention contemplates embodiments wherein the body and front cover have a non-circular shapes similar to that of U.S. Pat. No. 5,464,418 to SCHRAGA, the disclosure of which is hereby expressly incorporated by reference herein it its entirety. The invention also contemplates utilizing one or more of the lancet removal systems disclosed in pending U.S. patent application Ser. No. 11/548,613 (P30701) to SCHRAGA, the disclosure of which is hereby expressly incorporated by reference herein it its entirety.

The various parts, with the exception of the springs, can preferably be made as one-piece structures by e.g., injection molding. In this regard, they are preferably made of a plastic or synthetic resin such as, e.g., ABS plastic. The body and intermediate section can also be made of ABS—Metallic Silver and have a finish designated as SPI-A2. The front cover and push-button may also be made of ABS—Light Blue and have a finish designated as SPI-A2. The trigger may also have be made of ABS—Red and have a finish designated as SPI-A2. The holding member may also have be made of Delrin—Natural and have a finish designated as SPI-C1. Of course, other materials and/or finishes may be utilized, without leaving the scope of the invention. Moreover, each part may even be made of a plurality of sections of parts which are joined together to form the complete parts, without leaving the scope of the invention. Thus, all the parts of the lancet device, with the exception of the springs (which can be made of spring steel) and with the exception of the lancet needle (which can be a conventional metal needle mounted to a conventional plastic lancet L), may be made from plastic materials and can be formed using conventional injection molding techniques or other known manufacturing methods. The front cap and/or body, for example, can be integrally formed with peripheral grooves and/or projections (similar to a coin), and with the indicating marks. However, when practical, other materials and manufacturing processes may also be utilized. Examples of desirable plastics include polypropylene (PP), polyvinyl chloride (PVC), acrylonitrile butadiene styrene (ABS), nylon, linear polyoxymethylene-type acetal resin, e.g., "DELRIN", and polycarbonate (PC), e.g., "LEXAN". The invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A lancet device comprising:
    a body;
    a front cover comprising a skin engaging end that includes a lancet opening through which a lancet needle may extend;
    a holding member movably mounted within the body and comprising a front end and a rear end;
    the front end being configured to receive a lancet having the lancet needle;
    a first spring structured and arranged to move the holding member between at least a retracted position and an extended position;
    a second spring structured and arranged to move the holding member between at least an intermediate position and the retracted position; and
    a push-button arranged on a rear end of the body,
    wherein, when the push-button is depressed, the second spring is compressed by the push-button, and
    wherein, when the push-button is released, the second spring expands and the holding member is caused to move to a trigger-set position via a force generated by the second spring, and
    wherein, when the holding member is caused to move to the trigger-set position by the release of the push-button, the first spring is caused to be compressed.

2. The lancet device of claim 1, wherein at least one of:
    the lancet device has an adjustable depth of penetration arrangement;
    the lancet device is a single-use lancet device; and
    the lancet device is a multiple-use lancet device.

3. The lancet device of claim 1, wherein at least one of:
    the lancet device comprises an adjustable depth of penetration arrangement; and
    the lancet device comprises an intermediate member that is at least one of axially adjustably connected to the body and threadably connected to the body.

4. The lancet device of claim 3, wherein the intermediate member is non-removably connected to the body and wherein the front cover is movably and removably connected to the intermediate member.

5. The lancet device of claim 3, wherein movement of the intermediate member adjusts a depth of penetration of the lancet needle.

6. The lancet device of claim 3, wherein the front cover is non-rotatably mounted to the intermediate member.

7. The lancet device of claim 1, wherein the front cover is devoid of moving parts.

8. The lancet device of claim 1, wherein the front cover comprises a one-piece plastic or synthetic resin member.

9. The lancet device of claim 3, wherein movement of the intermediate member changes an overall length of the lancet device and wherein the intermediate member is spaced from the front cover.

10. The lancet device of claim 1, wherein axial expansion of the second spring causes axial compression of the first spring.

11. The lancet device of claim 1, wherein the second spring is sized to resist greater compression forces than the first spring.

12. The lancet device of claim 1, wherein the second spring is larger in diameter than the first spring.

13. The lancet device of claim 1, wherein the second spring is made from a wire having a larger diameter than a wire of the first spring.

14. The lancet device of claim 1, wherein each of the first and the second springs comprise helical compression springs.

15. The lancet device of claim 1, wherein the first spring has one end coupled to a portion of the body and another end coupled to a portion of the holding member.

16. The lancet device of claim 1, wherein the second spring biases the push-button towards an extended position.

17. The lancet device of claim 1, wherein the lancet device is structured and arranged to allow for replacement of the lancet and for multiple use.

18. The lancet device of claim 1, wherein the lancet is removably connected to the front end of the holding member.

19. The lancet device of claim 1, further comprising an arrangement for moving the holding member to a retracted or trigger-set position.

20. The lancet device of claim 1, wherein the holding member comprises a generally cylindrical cross-section.

21. The lancet device of claim 1, wherein the holding member comprises a generally polygonal cross-section.

22. The lancet device of claim 1, further comprising a locking member structured and arranged to releasably lock with the holding member and thereby retain the holding member in the retracted position.

23. The lancet device of claim 1, further comprising a deflecting member coupled to the holding member, wherein the deflecting member is engagable with a trigger.

24. The lancet device of claim 1, further comprising a trigger movably mounted to the body.

25. The lancet device of claim 1, further comprising a fixed stop surface that is contacted by a movable stop surface when the holding member moves to an extended position.

26. The lancet device of claim 1, wherein the front cover is removably and non-threadably mounted to a front portion of the body and further comprising an intermediate member non-removably mounted to a rear portion of the body.

27. The lancet device of claim 1, further comprising a mechanism for at least temporarily maintaining a depth setting position.

28. The lancet device of claim 1, wherein the holding member comprises an integrally formed deflecting member that engages a surface of the body.

29. The lancet device of claim 1, wherein the front end of the holding member comprises an opening that is configured to removably receive the lancet.

30. The lancet device of claim 1, further comprising at least one deflectable member configured to be deflected by a trigger thereby causing movement of the holding member to the extended position.

31. The lancet device of claim 30, wherein the at least one deflectable member is coupled to the push-button.

32. The lancet device of claim 30, wherein the at least one deflectable member is integrally formed with the push-button.

33. The lancet device of claim 1, further comprising indicia arranged on at least one of an intermediate member and the body.

34. The lancet device of claim 33, wherein the indicia is arranged on an outer circumferential surface of the body.

35. The lancet device of claim 33, wherein the indicia is arranged on an outer circumferential surface of the intermediate member.

36. The lancet device of claim 1, wherein the front cover rotates about an axis that runs through the lancet opening and the holding member without changing an overall length of the lancet device.

37. The lancet device of claim 1, wherein the second spring is disposed between a trigger and a back cap or the push-button.

38. The lancet device of claim 1, wherein the body comprises a two-piece body.

39. The lancet device of claim 1, wherein the body comprises an ergonomic shape.

40. The lancet device of claim 1, wherein the body comprises a plastic material.

41. The lancet device of claim 1, further comprising an intermediate member that comprises at least one of an external high-friction gripping surface and gripping protrusions.

42. The lancet device of claim 1, further comprising threads connecting an intermediate member to the body.

43. A method of puncturing a surface of skin using the lancet device of claim 1, the method comprising:
adjusting a set depth of penetration by rotating the intermediate member to a desired set position;
disposing the skin engaging end against a user's skin; and
compressing the second spring and thereafter allowing the second spring to automatically expand thereby causing compression of the first spring.

44. A method of puncturing a surface of skin using the lancet device of claim 1, the method comprising:
adjusting a set depth of penetration by rotating the intermediate member to a desired set position;
disposing the skin engaging end against a user's skin; and
compressing the second spring while the first spring remains in an unstressed state and thereafter allowing the second spring to expand thereby causing compression of the first spring.

45. A method of puncturing a surface of skin using the lancet device of claim 1, the method comprising:
disposing the skin engaging end against a user's skin; and
compressing the second spring while the first spring remains in an unstressed state and thereafter allowing the second spring to expand thereby automatically causing compression of the first spring.

46. An adjustable depth of penetration lancet device, the lancet device comprising:
a body;
a front cover comprising a skin engaging end that includes a lancet opening through which a lancet needle may extend;
a holding member movably mounted within the body and comprising a front end and a rear end;
the front end being configured to receive a lancet having the lancet needle;
a first spring structured and arranged to move the holding member between at least a retracted position and an extended position;
a second spring structured and arranged to at least one of:
move the holding member between at least an intermediate position and the retracted position; and
cause compression of the first spring;
a push-button member structured and arranged to cause compression of the second spring when the push-button is depressed and to cause compression of the first spring when the push-button is released; and
the push button also being structured and arranged to move the holding member to the retracted position after a portion of the push-button is releasably connected to a portion of the holding member.

47. A lancet device comprising:
a body having a front end and a rear end; a holding member configured to receive a lancet having the lancet needle;
a first spring structured and arranged to move the holding member between at least a retracted position and an extended position; and
a second spring structured and arranged to move the holding member between at least an intermediate position and the retracted position,
wherein expansion of the second spring automatically causes compression of the first spring and movement of the holding member to the retracted position, and
wherein, after the holding member moves to a trigger-set position, the lancet device is automatically triggered,
wherein the first spring is arranged axially closer to the front end of the body than the second spring and is at least one of:
smaller in diameter than the second spring; and
compressible by expansion of the second spring.

48. The lancet device of claim 47, further comprising at least one of:
a push-button member structured and arranged to cause compression of the second spring and to move the holding member to the retracted position; and
a triggering arrangement structured and arranged to releasably engage with the holding member.

49. A lancet device comprising:
a body;
a movable lancet holding member structured and arranged to receive a removable lancet; and
a cocking and triggering system structured and arranged to automatically cock and trigger the lancet device when activated by a user,
wherein the cocking and triggering system includes a push-button arranged on a rear end of the body which, when depressed, compresses one spring and moves to a position so as to allow the push-button to releasably connect to the lancet holding member and, when released, releasably connects to the lancet holding member and moves the lancet holding member towards a trigger-set position and causes compression of another spring, and then automatically disconnects from the lancet holding member.

50. The lancet device of claim 1, wherein, when the holding member is caused to move via the second spring to the trigger-set position by the release of the push-button and rearward movement of the push-button, the first spring is caused to be compressed by an expansion force of the second spring.

51. The lancet device of claim 1, wherein the first spring is arranged to surround a portion of the lancet holding member.

52. The lancet device of claim 1, wherein the first spring and the second spring each have a center axis arranged parallel to an axis of the lancet holding member.

53. The lancet device of claim 1, wherein the first spring and the second spring each have a center axis arranged parallel to one another.

54. The lancet device of claim 1, wherein the first spring and the second spring are axially spaced from one another.

55. The lancet device of claim 1, wherein the lancet device is cocked and trigger by rearward movement of the push-button.

56. The lancet device of claim 1, wherein the lancet device is cocked and trigger by rearward movement of the push-button which is caused by axial expansion of the second spring.

57. The lancet device of claim 1, wherein the lancet device is automatically cocked and trigger by rearward movement of the push-button and axial expansion of the second spring.

58. The lancet device of claim 1, wherein the lancet device is automatically triggered after the push-button is released and moves back away from the body to a pre-determined position.

\* \* \* \* \*